(12) United States Patent
Lonard et al.

(10) Patent No.: US 11,312,676 B2
(45) Date of Patent: Apr. 26, 2022

(54) SMALL MOLECULE STIMULATORS OF STEROID RECEPTOR COACTIVATOR PROTEINS AND THEIR USE IN THE TREATMENT OF CANCER

(71) Applicant: BAYLOR COLLEGE OF MEDICINE, Houston, TX (US)

(72) Inventors: David Michael Lonard, Pearland, TX (US); Lei Wang, Pearland, TX (US); Bert W. O'Malley, Houston, TX (US); Jianming Xu, Bellaire, TX (US); Yongcheng Song, Pearland, TX (US); Xiaonan Li, Sugar Land, TX (US); Timothy Gerald Palzkill, Houston, TX (US)

(73) Assignee: BAYLOR COLLEGE OF MEDICINE, Houston, TX (US)

( * ) Notice: Subject to any disclaimer, the term of this patent is extended or adjusted under 35 U.S.C. 154(b) by 0 days.

(21) Appl. No.: 15/540,386

(22) PCT Filed: Dec. 29, 2015

(86) PCT No.: PCT/US2015/067770
§ 371 (c)(1),
(2) Date: Jun. 28, 2017

(87) PCT Pub. No.: WO2016/109470
PCT Pub. Date: Jul. 7, 2016

(65) Prior Publication Data
US 2018/0265444 A1    Sep. 20, 2018

Related U.S. Application Data

(60) Provisional application No. 62/097,995, filed on Dec. 30, 2014.

(51) Int. Cl.
| | | |
|---|---|---|
| C07C 49/753 | (2006.01) |
| A61K 31/444 | (2006.01) |
| A61K 31/45 | (2006.01) |
| A61K 31/4402 | (2006.01) |
| A61K 31/351 | (2006.01) |
| A61K 31/4433 | (2006.01) |
| A61K 31/122 | (2006.01) |
| A61K 31/4545 | (2006.01) |
| C07D 401/06 | (2006.01) |
| C07D 309/38 | (2006.01) |
| C07D 405/06 | (2006.01) |
| C07D 213/68 | (2006.01) |
| C07D 405/12 | (2006.01) |
| A61P 35/00 | (2006.01) |
| C07C 49/697 | (2006.01) |
| C07D 211/86 | (2006.01) |
| C07D 213/50 | (2006.01) |
| C07D 309/32 | (2006.01) |
| C07D 401/14 | (2006.01) |
| C07D 405/14 | (2006.01) |

(52) U.S. Cl.
CPC .......... *C07C 49/753* (2013.01); *A61K 31/122* (2013.01); *A61K 31/351* (2013.01); *A61K 31/4402* (2013.01); *A61K 31/444* (2013.01); *A61K 31/4433* (2013.01); *A61K 31/45* (2013.01); *A61K 31/4545* (2013.01); *A61P 35/00* (2018.01); *C07C 49/697* (2013.01); *C07D 211/86* (2013.01); *C07D 213/50* (2013.01); *C07D 213/68* (2013.01); *C07D 309/32* (2013.01); *C07D 309/38* (2013.01); *C07D 401/06* (2013.01); *C07D 401/14* (2013.01); *C07D 405/06* (2013.01); *C07D 405/12* (2013.01); *C07D 405/14* (2013.01); *C07C 2601/14* (2017.05)

(58) Field of Classification Search
USPC ....................................................... 514/318
See application file for complete search history.

(56) References Cited

U.S. PATENT DOCUMENTS

| | | | |
|---|---|---|---|
| 6,664,272 B2 | 12/2003 | Snyder et al. | |
| 8,785,490 B2* | 7/2014 | Trent ................... | A61K 31/132 514/354 |
| 2007/0010488 A1* | 1/2007 | Youssef ................. | A61K 31/35 514/63 |
| 2010/0093611 A1 | 4/2010 | Horrigan et al. | |

FOREIGN PATENT DOCUMENTS

| | | |
|---|---|---|
| CN | 102381951 A | 3/2012 |
| CN | 102153508 | 1/2013 |
| CN | 106083704 | 7/2018 |
| EP | 2303328 | 4/2011 |
| EP | 2927208 A1 | 10/2015 |

(Continued)

OTHER PUBLICATIONS

Liu, Yang (Synthesis of 3, 5-dibenzylidene-4-piperidinone analogs and their antitumor activities in vitro, 2010 as cited in the STIC search).*
Abraham et al., "A morphologically conserved nonapoptotic program promotes linker cell death in caenorhabditis elegans", Developmental Cell, vol. 12, pp. 73-86, 2007.
Adams et al., "Discovery of small-molecule enhancers of reactive oxygen species that are nontoxic or cause genotype-selective cell death", ACS Chem Biol, vol. 8, pp. 923-929, 2013.
Adams et al., "Synthesis, cellular evaluation, and mechanism of action of piperlongumine analogs", Proc Natl Acad Sci USA, vol. 109, pp. 15115-15120, 2012.

(Continued)

*Primary Examiner* — Kathrien A Cruz
(74) *Attorney, Agent, or Firm* — Kilpatrick Townsend & Stockton LLP

(57) ABSTRACT

Small molecule stimulators of steroid receptor coactivator (SRC) family proteins are provided, as well as methods for their use in treating or preventing cancer. Also provided are methods for stimulating SRC family proteins in a cell.

7 Claims, 15 Drawing Sheets
Specification includes a Sequence Listing.

(56) References Cited

FOREIGN PATENT DOCUMENTS

| WO | 9518606 | 7/1995 |
|---|---|---|
| WO | 0140188 A1 | 6/2001 |
| WO | 0146110 A2 | 6/2001 |
| WO | 2008144011 A1 | 11/2008 |
| WO | 2008150899 A1 | 12/2008 |
| WO | 2009073050 | 6/2009 |
| WO | 2011029359 A1 | 3/2011 |
| WO | 2012021692 A1 | 2/2012 |
| WO | 2014082581 A1 | 6/2014 |
| WO | 2014111268 | 7/2014 |
| WO | 2019097080 | 5/2019 |

OTHER PUBLICATIONS

Anzick et al., "Aib1, a steroid receptor coactivator amplified in breast and ovarian cancer", Science, vol. 277, pp. 965-968, 1997.
Bautista et al., "In breast cancer, amplification of the steroid receptor coactivator gene AIB1 is correlated with estrogen and progesterone receptor positivity", Clinical cancer research : an official journal of the American Association for Cancer Research vol. 4, 2925-2929, 1998.
Bouras et al., "Overexpression of the steroid receptor coactivator Aib1 in breast cancer correlates with the absence of estrogen and progesterone receptors and positivity for P53 and Her2/Neu", Cancer Research, vol. 61, pp. 903-907, 2001.
Cai et al., "Steroid receptor coactivator-3 expression in lung cancer and its role in the regulation of cancer cell survival and proliferation", Cancer Research, Vo. 70, pp. 6477-6485, 2010.
Chen et al., "Living T9 glioma cells expressing membrane macrophage colony-stimulating factor produce immediate tumor destruction by polymorphonuclear leukocytes and macrophages via a "paraptosis"-induced pathway that promotes systemic immunity against intracranial T9 G", Blood, vol. 100, pp. 1373-1380, 2002.
Chen et al., "Nuclear receptor coactivator Actr is a novel histone acetyltransferase and forms a multimeric activation complex with P/Caf and Cbp/P300", Cell, vol. 90, pp. 569-580, 1997.
Chen et al., "Regulation of transcription by a protein methyltransferase", Science, vol. 284, pp. 2174-2177, 1999.
Chi et al., "Oncogenic ras triggers cell suicide through the activation of a caspase-independent cell death program in human cancer cells", Oncogene, vol. 18, pp. 2281-2290, 1999.
Chin et al., "Essential role for oncogenic Ras in tumour maintenance", Nature, vol. 400, pp. 468-472, 1999.
Clarke , "Developmental cell death: Morphological diversity and multiple mechanisms", Anatomy and Embryology, vol. 181, pp. 195-213, 1990.
De Jong et al., "Tyrosine 207 in Crkl is the Bcr/Abl phosphorylation site", Oncogene, vol. 14, pp. 507-513, 1997.
Dengler et al., "Oncogenic stress induced by acute hyper-activation of Bcr-Abl leads to cell death upon induction of excessive aerobic glycolysis", PloS One, vol. 6, e25139, pp. 1-13, 2011.
Denoyelle et al., "Anti-oncogenic role of the endoplasmic reticulum differentially activated by mutations in the mapk pathway", Nature Cell Biology, vol. 8, pp. 1053-1063, 2006.
Ding et al., "Absence of Bax switched Mg132-induced apoptosis to non-apoptotic cell death that could be suppressed by transcriptional or translational inhibition", Apoptosis: An International Journal on Programmed Cell Death, vol. 12, pp. 2233-2244, 2007.
Enyedi, et al., "Redox state of the endoplasmic reticulum is controlled by Ero1L-alpha and intraluminal calcium", Antioxidants & redox signaling, vol. 13, pp. 721-729 2010.
Epps et al., "Determination of the affinity of drugs toward serum albumin by measurement of the quenching of the intrinsic tryptophan fluorescence of the protein", The Journal of Pharmacy and Pharmacology, vol. 51, pp. 41-48, 1999.
Felsher et al., "Reversible tumorigenesis by Myc in hematopoietic lineages", Molecular Cell, vol. 4, pp. 199-207, 1999.

Fereshteh et al., "The nuclear receptor coactivator amplified in breast cancer-1 is required for Neu (Erbb2/Her2) activation, signaling, and mammary tumorigenesis in mice", Cancer Research, vol. 68, pp. 3697-3706, 2008.
Fleming et al., "Expression Of SRC-1, AIB1, and PEA3 in HERr2 mediated endocrine resistant breast cancer; a predictive role for Src-1", Journal of Clinical Pathology, vol. 57, pp. 1069-1074, 2004.
Foulds et al., "Proteomic analysis of coregulators bound to Eralpha on DNA and nucleosomes reveals coregulator dynamics", Mol Cell, vol. 51, pp. 185-199, 2013.
Glaeser et al., "Gene amplification and expression of the steroid receptor coactivator Src3 (Aib1) in sporadic breast and endometrial carcinomas", Hormone and Metabolic Research, vol. 33, pp. 121-126, 2001.
Gnanapragasam et al., "Expression of Rac 3, a steroid hormone receptor co-activator in prostate cancer", British Journal of Cancer, vol. 85, pp. 1928-1936, 2001.
Grek et al., "Redox metabolism and malignancy", Current Opinion in Pharmacology, vol. 10, pp. 362-368, 2010.
Greuber et al., "Role of ABL family kinases in cancer: From leukaemia to solid tumours", Nature Reviews Cancer, vol. 13, pp. 559-571, 2013.
Han et al., "ER-stress-induced transcriptional regulation increases protein synthesis leading to cell death", Nature cell biology, 15:481-490, 2013.
Henke et al., "Overexpression of the nuclear receptor coactivator AIB1 (SRC-3) during progression of pancreatic adenocarcinoma", Clinical Cancer Research : An Official Journal of the American Association for Cancer Research, vol. 10(18 Pt 1, pp. 6134-6142), 2004.
Hudelist et al., "Expression of sex steroid receptors and their co-factors in normal and malignant breast tissue Aib1 is a carcinoma-specific co-activator", Breast Cancer Research and Treatment, vol. 78, pp. 193-204, 2003.
Huettner et al., "Reversibility of acute B-cell leukaemia induced by Bcr-abl1", Nature Genetics, vol. 24, pp. 57-60, 2000.
Jain et al., "Sustained loss of a neoplastic phenotype by brief inactivation of Myc", Science, vol. 297, pp. 102-104, 2002.
Jambrina et al., "Calcium influx through receptor-operated channel induces mitochondria-triggered paraptotic cell death", The Journal of Biological Chemistry, vol. 278, p. 14134-14145, 2003.
Kar et al., "A novel role for Map1 Lc3 in nonautophagic cytoplasmic vacuolation death of cancer cells", Oncogene, vol. 28, pp. 2556-2568, 2009.
Kershah et al., "Expression of estrogen receptor coregulators in normal and malignant human endometrium", Gynecologic Oncology, vol. 92, pp. 304-313, 2004.
Kinoshita et al., "Recognition of phosphate monoester dianion by an alkoxide-bridged dinuclear zinc(ii) complex", Dalton Transactions, pp. 1189-1193, 2004.
Le et al., "Inhibition of lactate dehydrogenase a induces oxidative stress and inhibits tumor progression", Proceedings of the National Academy of Sciences of the United States of America, vol. 107, pp. 2037-2042, 2010.
Leung et al., "Identification of cyclohexanone derivatives that act as catalytic inhibitors of topoisomerase I: effects on tamoxifen-resistant MCF-7 cancer cells", Invest New Drugs, 30:2103-2112, 2012.
List et al., "Ribozyme targeting demonstrates that the nuclear receptor coactivator aib1 is a rate-limiting factor for estrogen-dependent growth of human Mcf-7 breast cancer cells", J Biol Chem, vol. 276, pp. 23763-23768, 2001.
Lonard et al., "Nuclear receptor coregulators: Judges, juries, and executioners of cellular regulation.", Molecular Cell, vol. 27, No. 5, pp. 691-700, 2007.
Lonard et al., "The 26s proteasome is required for estrogen receptor-alpha and coactivator turnover and for efficient estrogen receptor-alpha transactivation", Molecular Cell. vol. 5, No. 6, pp. 939-948, 2000.
Louet et al., "The coactivator Src-1 is an essential coordinator of hepatic glucose production", Cell Metabolism, vol. 12, pp. 606-618, 2010.

(56) References Cited

OTHER PUBLICATIONS

Meyer et al., "Reflecting on 25 years With Myc", Nature Reviews Cancer, vol. 8, pp. 976-990, 2008.

Mimnaugh et al., "Endoplasmic reticulum vacuolization and valosin-containing protein relocalization result from simultaneous Hsp90 inhibition by geldanamycin and proteasome inhibition by velcade", Molecular Cancer Research: MCR, vol. 4, pp. 667-681, 2006.

Myers et al., "Inverse relationship between Er-beta and Src-1 predicts outcome in endocrine-resistant breast cancer", British Journal of Cancer, vol. 91, pp. 1687-1693, 2004.

Noguchi et al., "ATPase Activity of P97/valosin-containing protein is regulated by oxidative modification of the evolutionally conserved cysteine 522 residue in walker A motif.", The Journal of Biological Chemistry, vol. 280, pp. 41332-41341, 2005.

Oh et al., "Tyrosine phosphorylation of the nuclear receptor coactivator Aib1/src-3 is enhanced by Abl kinase and is required for its activity in cancer cells", Molecular and Cellular Biology, vol. 28, pp. 6580-6593, 2008.

O'Malley, "Development of coactivator-dependent, first-in-class therapies for breast cancer", Available online at: www.dtic.miljcgi-binjGetTRDocAD=ADA614 113, pp. 7-9, Sep. 2014.

PCT/US2015/067770, "International Preliminary Report on Patentability", dated Jul. 13, 2017, 14 pages.

PCT/US2015/067770, "International Search Report and Written Opinion", dated May 24, 2016, 21 pages.

PCT/US2015/067770, "Invitation to Pay Additional Fees and Partial Search Report", dated Mar. 11, 2016, 10 pages.

Pilar et al., "Ultrastructural differences during embryonic cell death in normal and peripherally deprived ciliary ganglia", The Journal of Cell Biology, vol. 68, pp. 339-356, 1976.

Pubchem Bioassay, "4-Ethyl-2,6-bis-pyridin-3-ylmethylene-cyclohexanone" CID 2175947—Compound BioActivity Data, retrieved at http://pubchem.ncbi.nlm.nih.gov/assay/assay.cgi, Aug. 12, 2014, 25 pages.

Pubchem Bioassay, "4Luminescence-based cell-based primary high throughput screening assay to identify inhibitors of the steroid receptor coactivator 2 (SRC2; NCOA2)", retrieved at http://pubchem.ncbi.nlm.nih.gov/assay/assay.cgi?aid=651957, Mar. 27, 2014, 7 pages.

Pubchem Bioassay, "Summary of the probe development efforts to identify inhibitors of the steroid receptor coactivator 1 (SRC1;NCOA1)", retrieved at http://pubchem.ncbi.nlm.nih.gov/bioassay/588362, Nov. 21, 2012, 11 pages.

Pubchem Bioassay, "Summary of the probe development efforts to identify inhibitors of the steroid receptor coactivator2 (SRC2;NCOA2)", retrieved at http://pubchem.ncbi.nlm.nih.gov/bioassay/651960, Feb. 4, 2013, 10 pages.

Pubchem Bioassay, "Summary of the probe development efforts to identify inhibitors of the steroid receptor coactivator 3 (SRC3;NCOA3)", retrieved at http://pubchem.ncbi.nlm.nih.gov/bioassay/588357, Mar. 4, 2013, 11 pages.

Pubchem Bioassay, "Counterscreen for inhibitors of the steroid receptor coactivator 3 (SRC3; NCOA3) Tuminescence-based cell-based high throughput assay to identify inhibitors of the herpes virus virion protein 16 (KVP16)", retrieved at http://pubchem.ncbi.nlm.nih.gov/bioassay/588794, Nov. 16, 2011,17 pages.

Pubchem CID Nos. 4114212 (2,6-bis[(3-methoxyphenyl)methylidene]cyclohexan-1-one; 1741341 ((2E,6E)-2,6-bis[(3-methoxylphenyl)methylidene]cyclohexan-1-one); 1741339 (2E,6Z)-2,6-bis[(3-methoxyphenyl)methylidene]cyclohexan-1-one; 3491436 2,6-bis[(3-methoxyphenyl)methylidene]-4-methylcoclohexan-1-one; 6938059 (2E)-2,6-bis[(3-methoxyphenyl)methylidene]-4-methylcyclohexan-1-one; 2347547 (2E,6E)-2,6-bis[(3-methoxyphenyl)methylidene]-4-methylcyclohexan-1-one; 2347546 (2Z,6E)-2,6-bis[(3-methoxyphenyl)methylidene]-4-methylcoclohexan-1-one, retrieved online from https://pubchem.ncbi.nlm.nih.gov/search/index.html on Mar. 27, 2014.

Pubchem CID Nos. 6518906 (2E,6E)-2,6-bis(pyridine-2-ylmethylidene)cyclohexan-1-one; 3839298 2,6-bis(pyridine-2-ylmethylidene)cyclohexan-1-one; 26788142 (6E)-2,6-bis(pyridine-2-ylmethylidene)cyclohexan-1-one; 39842650 (2E,6Z)-2,6-bis(pyridine-2-ylmethylidene)cyclohexan-1-one; retrieved online from https://pubchem.ncbi.nlm.nih.gov/search/index.html on Mar. 27, 2014.

Pubchem CID Nos. 3491436 2,6-bis[(3-methoxyphenyl)methylidene]-4-methylcyclohexan-1-one; 6938059 (2E)-2,6-bis[(3-methoxyphenyl)methylidene]-4-methylcyclohexan-1-one; 2347547 (2E,6E)-2,6-bis[(3-methoxyphenyl)methylidene]-4-methylcyclohexan-1-one; 2347546 (2Z,6E)-2,6-bis[(3-methoxyphenyl)methylidene]-4-methylcyclohexan-1-one; 4114212 2,6-bis[(3-methoxyphenyl)methylidene]cyclohexan-1-one; 1741341 (2E,6E)-2,6-bis[(3-methoxyphenyl)methylidene]cyclohexan-1-one; 1741339 (2E,6Z)-2,6-bis[(3-methoxyphenyl)methylidene]cyclohexan-1-one; retrieved online from https://pubchem.ncbi.nlm.nih.gov/search/index.html on Mar. 27, 2014.

Pubchem CID Nos. 1587345 (2E,6E)-4-methyl-2,6-bis(pyridine-3-ylmethylidene)cyclohexan-1-one; 1587342 (2Z,6E)-4-methyl-2,6-bis(Pyridin-3-ylmethylidene)cyclohexan-1-one; 706760 4-methyl-2,6-bis(pyridine-3-ylmethylidene)cyclohexan-1-one; 2175947 (2E,6E)-4-ethyl-2,6-bis(pyridine-3-ylmethylidene)cyclohexan-1-one 695638 4-ethyl-2-6-bis(pyridine-3-ylethylidene)cyclohexan-1-one; 2175945 (2Z,6E)-4-ethyl-2,6-bis(pyridine-3-ylmethylidene)cyclohexan-1-one; 2175949 (2Z,6Z)-4-ethyl-2,6-bis(pyridine-3-ylmethylidene)cyclohexan-1-one; 16188433 (2Z,6E)-4-methyl-2,6-bis(pyridine-4-ylmethylidene)cyclohexan-1-one; 3639762 4-methyl-2,6-bis(pyridine-4-ylmethylidene)cyclohexan-1-one; 6010863 (2E,6E)-4-methyl-2,6-bis(pyridine-4-ylmethylidene)cyclohexan-1-one; retrieved online from https://pubchem.ncbi.nlm.nih.gov/search/index.html on Mar. 27, 2014.

Pubchem CID Nos. 60165427 (3E,5E)-3,5-bis(pyridine-2-ylmethylidene)oxan-4-one; 72670476 3,5-bis(pyridine-2-ylmethylidene)oxan-4-one; retrieved online from https://pubchem.ncbi.nlm.nih.gov/search/index.html on Mar. 27, 2014.

Pubchem CID Nos. 13306030 (3E,5E)-3,5-bis[(2-methoxyphenyl)methylidene]-1-methylpiperidin-4-one; 20416720 (3E,5E)-1-ethyl-3,5-bis[(2methoxyphenyl)methylidene]piperidin-4-one; 20416721 (3E,5E)-3,5-bis[(2-methoxyphenyl)methylidene]-1-propylpiperidin-4-one; retrieved online from https://pubchem.ncbi.nlm.nih.gov/search/index.html on Mar. 27, 2014.

Pubchem CID Nos. 6086459 (3E,5E)-3,5-bis[(4-bromophenyl)methylidene]-1-butylpiperidin-4-one; 5502561 (3E,5E)-3,5-bis[(4-bromophenyl)methylidene]-1-methylpiperidin-4-one; 1283565 3,5-bis[(4-bromophynyl)methylidene]-1-methylpiperidin-4-one; 1283573 3,5-bis[(4-bromophenyl)methylidene]-1-ethylpiperidin-4-one; 332657 3,5-bis[(4-bromophenyl)methylidene]-1-butylpiperidin-4-one; 2828284 3,5-bis[(4-bromophenyl)methylidene]-1-propylpiperidin-4-one; 2304590 (3Z,5E)-3,5-bis[(4-bromophenyl)methylidene]-1-propylpiperidin-4-one; 2304592 (3E,5E)-3,5-bis[(4-bromophenyl)methylidene]-1-propylpiperidin-4-one; 2395940 (3Z,5E)-3,5-bis[(4-bromophenyl)methylidene]-1-ethylpiperidin-4-one; 2395943 (3E,5E)-3,5-bis[(4-bromophenyl)methylidene]-1-ethylpiperidin-4-one; retrieved online from https://pubchem.ncbi.nlm.nih.gov/search/index.html on Mar. 27, 2014.

Pubchem CID Nos. 5070709 3,5-bis[(3,4-dichlorophenyl)methylidene]-1-ethylpiperidin-4-one; 2390410 (3Z,5E)-3,5-bis[(3,4-dichlorophenyl)methylidene]-1-ethylpiperidin-4-one; 2390412 (3E,5E)-3,5-bis[(3,4-dichlorophenyl)methylidene]-1-ethylpiperidin-4-one; 6526444 (3E,5E)-3,5-bis[(3,4-dichlorophenyl)methylidene]-1-methylpiperidin-4-one; 4417366 3,5-bis[(3,4-dichlorophenyl)methylidene]-1-methylpiperidin-4-one; retrieved online from https://pubchem.ncbi.nlm.nih.gov/search/index.html on Mar. 27, 2014.

Pubchem CID Nos. 2265240 (3Z,5E)-1-methyl-3,5-bis(pyridine-3-ylmethylidene)piperidin-4-one; 2265242 (3E,5E)-1-methyl-3,5-bis(pyridine-3-ylmethylidene)piperidin-4-one; 702066 1-methyl-3,5-bis(pyridine-3-ylmethylidene)piperidin-4-one; 52446215 (3Z,5E)-1-ethyl-3,5-bis(pyridine-3-ylmethylidene)piperidin-4-one; 52446224 (3Z,5E)-1-propyl-3,5-bis(pyridine-3-ylmethylidene)piperidin-4-one; retrieved online from https://pubchem.ncbi.nlm.nih.gov/search/index.html on Mar. 27, 2014.

Pubchem CID Nos. 5182696 3,5-bis[3,4-dichlorophenyl)methylidene]-1-propan-2-ylpiperidin-4-one; 6535788 (3E,5E)-3,5-bis[(3,4-dichlorophenyl)methylidene]-1-propan-2-ylpiperidin-4-one; retrieved online from https://pubchem.ncbi.nlm.nih.gov/search/index.html on Mar. 27, 2014.

(56) References Cited

OTHER PUBLICATIONS

Qin et al., "The steroid receptor coactivator-1 regulates twist expression and promotes breast cancer metastasis", Cancer Research, vol. 69, pp. 3819-3827, 2009.

Raj et al., "Selective killing of cancer cells by a small molecule targeting the stress response to ROS", Nature, vol. 475, No. 7355, pp. 231-234, 2011.

Ray et al., "Reactive oxygen species (Ros) homeostasis and redox regulation in cellular signaling", Cellular Signaling, vol. 24, pp. 981-990, 2012.

Sakakura et al., "Amplification and over-expression of the AIB1 nuclear receptor co-activator gene in primary gastric cancers", International Journal of Cancer. Journal International du Cancer, vol. 89, No. 3, pp. 217-223, 2000.

Somers-Edgar et al., "Mechanisms for the activity of heterocyclic cyclohexanone curcumin derivatives in estrogen receptor negative human breast cancer cell lines", Investigational New Drugs, 29(1):87-97, 2011.

Sperandio et al., "An alternative, nonapoptotic form of programmed cell death", Proceedings of the National Academy of Sciences of the United States of America, vol. 97, pp. 14376-14381, 2000.

Stashi et al., "Steroid receptor coactivators: servants and masters for control of systems metabolism", Trends in Endocrinology and Metabolism: TEM, vol. 25, No. 7, pp. 337-347, 2014.

Sun et al., "Activation of the cytoplasmic C-abl tyrosine kinase by reactive oxygen species", The Journal of Biological Chemistry, vol. 275, pp. 17237-17240, 2000.

Surechem, (3E,5E)-3,5-bis(pyridine-3-ylmethylidene)oxan-4-one Inchi key: CCSROPREUQUEXY_BGPOSVGRSA_N; retrieved online from https://open.surechem.com/en/chemical?struct on Mar. 27, 2014.

Tardito et al., "The thioxotriazole copper(Ii) complex A0 induces endoplasmic reticulum stress and paraptotic death in human cancer cells", The Journal of Biological Chemistry, vol. 284, pp. 24306-24319, 2009.

Taylor et al., "Integrative genomic profiling of human prostate cancer", Cancer Cell, vol. 18, pp. 11-22, 2010.

Thuerauf et al., "Effects of the isoform-specific characteristics of Atf6 alpha and Atf6 beta on endoplasmic reticulum stress response gene expression and cell viability", The Journal of Biological Chemistry, vol. 282, pp. 22865-22878, 2007.

Thuerauf et al., "Opposing roles for Atf6alpha and Atf6beta in endoplasmic reticulum stress response gene induction", The Journal of Biological Chemistry, vol. 279, pp. 21078-21084, 2004.

Torres-Arzayus et al., "High tumor incidence and activation of the PI3K/AKT pathway in transgenic mice define AIB1 as an oncogene", Cancer Cell, vol. 6, No. 3, pp. 263-274, 2004.

Torres-Arzayus et al., "Targeting the Aib1 oncogene through mammalian target of rapamycin inhibition in the mammary gland", Cancer Research, vol. 66, pp. 11381-11388, 2006.

Ustundag et al., "Proteasome inhibition-induces endoplasmic reticulum dysfunction and cell death of human cholangiocarcinoma cells", World Journal of Gastroenterology: WJG, vol. 13, pp. 851-857, 2007.

Wang et al., "Bufalin is a potent small molecule inhibitor of the steroid receptor coactivators SRC-3 and SRC-1", Cancer Research. Vol. 74, No. 5, pp. 1506-1517, Mar. 1, 2014.

Wang et al., "Characterization of a steroid receptor coactivator small molecule stimulator that overstimulates cancer cells and leads to cell stress and death", Cancer Cell, vol. 28, Iss. 2., pp. 240-252, Aug. 10, 2015.

Wang et al., "Disruption of the Src-1 gene in mice suppresses breast cancer metastasis without affecting primary tumor formation", Proceedings of the National Academy of Sciences of the United States of America, vol. 106, pp. 151-156, 2009.

Wang et al., "Prognostic significance of C-myc and Aib1 amplification in hepatocellular carcinoma. A broad survey using high-throughput tissue microarray", Cancer, 2002, pp. 2346-2352, vol. 95.

Wang et al., "Small molecule inhibition of the steroid receptor coactivators, SRC-3 and SRC-1", Molecular Endocrinology. Vol. 25, No. 12, pp. 2041-2053, Dec. 2011.

Wang et al., "The impact of the unfolded protein response on human disease", The Journal of Cell Biology, vol. 197, pp. 857-867, 2012.

Wu et al., "Selective phosphorylations of the Src-3/aib1 coactivator integrate genomic reponses to multiple cellular signaling pathways", Molecular Cell, vol. 15, pp. 937-949, 2004.

Xie et al., "Correlation of Aib1 overexpression with advanced clinical stage of human colorectal carcinoma", Human Pathology, vol. 36, pp. 777-783, 2005.

Xu et al., "Normal and cancer-related functions of the P160 steroid receptor co-activator (SRC) family", Nature Reviews. Cancer vol. 9, No. 9, pp. 615-630, Sep. 2009.

Yan et al., "Identification of verrucarin a as a potent and selective steroid receptor coactivator-3 small molecule inhibitor", PloS one., vol. 9, No. 4, e95243, pp. 1-9, Apr. 17, 2014.

Yan et al., "Steroid receptor coactivator-3/aib1 promotes cell migration and invasiveness through focal adhesion turnover and matrix metalloproteinase expression", Cancer Research, vol. 68, pp. 5460-5468, 2008.

Yi et al., "SRC-3 coactivator regulates cell resistance to cytotoxic stress via TRAF4-mediated p53 destabilization", Genes & development, 27:274-287, 2013.

Yoon et al., "Simultaneous mitochondrial Ca(2+) overload and proteasomal inhibition are responsible for the induction of paraptosis in malignant breast cancer cells", Cancer Letters, vol. 324, pp. 197-209, 2012.

Yoon et al., "Superoxide anion and proteasomal dysfunction contribute to curcumin-induced paraptosis of malignant breast cancer cells", Free Radical Biology & Medicine, vol. 48, pp. 713-726, 2009.

York et al., "Steroid receptor coactivator (Src) family: Masters of systems biology", J Biol Chem. Vol. 285, No. 50, pp. 38743-38750, Dec. 10, 2010.

Zhao et al., "Elevated expression levels of Ncoa3, Top1, and Tfap2c in breast tumors as predictors of poor prognosis", Cancer, vol. 98, pp. 18-23, 2003.

Jana et al., Curcumin Delays Endometriosis Development by Inhibiting MMP-2 Activity, Indian Journal Biochemistry Biophysics, vol. 49, No. 5, Oct. 2012, pp. 342-348.

Kumar et al., Curcumin-Loaded Lipid Nanocarrier for Improving Bioavailability, Stability and Cytotoxicity Against Malignant Glioma Cells, Drug Delivery, vol. 23, No. 1, May 14, 2014, pp. 214-229.

Thayyullathil et al., ROS-Dependent Prostate Apoptosis Response-4 (Par-4) Up-Regulation and Ceramide Generation are the Prime Signaling Events Associated With Curcumin-Induced Autophagic Cell Death in Human Malignant Glioma, FEBS Open Bio, vol. 4, Aug. 30, 2014, pp. 763-776.

Zhang et al., Curcumin Inhibits Endometriosis Endometrial Cells by Reducing Estradiol Production, Iran J. Reprod. Med., vol. 11, No. 5, May 2013, pp. 415-422.

Huang et al., Design, Synthesis, and Evaluation of NDGA Analogues as Potential Anti- Ischemic Stroke Agents, European Journal of Medicinal Chemistry, Elsevier, vol. 143, Jan. 2018, pp. 1165-1173.

\* cited by examiner

A.

B.

A.

B.

C.

```
                              SEQUENCE LISTING

<160> NUMBER OF SEQ ID NOS: 16

<210> SEQ ID NO 1
<211> LENGTH: 20
<212> TYPE: DNA
<213> ORGANISM: Artificial sequence
<220> FEATURE:
<223> OTHER INFORMATION: Synthetic construct

<400> SEQUENCE: 1
ccagtctccg aggagaaaca                                                   20

<210> SEQ ID NO 2
<211> LENGTH: 20
<212> TYPE: DNA
<213> ORGANISM: Artificial sequence
<220> FEATURE:
<223> OTHER INFORMATION: Synthetic construct

<400> SEQUENCE: 2
aaaaacagct ccgcatcaac                                                   20

<210> SEQ ID NO 3
<211> LENGTH: 21
<212> TYPE: DNA
<213> ORGANISM: Artificial sequence
<220> FEATURE:
<223> OTHER INFORMATION: Synthetic construct

<400> SEQUENCE: 3
caccacagtc cttctgcagt c                                                 21

<210> SEQ ID NO 4
<211> LENGTH: 20
<212> TYPE: DNA
<213> ORGANISM: Artificial sequence
<220> FEATURE:
<223> OTHER INFORMATION: Synthetic construct

<400> SEQUENCE: 4
tcaggctgga ctcgaatagc                                                   20

<210> SEQ ID NO 5
<211> LENGTH: 21
<212> TYPE: DNA
<213> ORGANISM: Artificial sequence
<220> FEATURE:
<223> OTHER INFORMATION: Synthetic construct

<400> SEQUENCE: 5
aaggcactga gcgtatcatg t                                                 21

<210> SEQ ID NO 6
<211> LENGTH: 25
<212> TYPE: DNA
<213> ORGANISM: Artificial sequence
<220> FEATURE:
<223> OTHER INFORMATION: Synthetic construct

<400> SEQUENCE: 6
tgaagataca cttccttctt gaaca                                             25
```

<210> SEQ ID NO 7
<211> LENGTH: 21
<212> TYPE: DNA
<213> ORGANISM: Artificial sequence
<220> FEATURE:
<223> OTHER INFORMATION: Synthetic construct

<400> SEQUENCE: 7
gagctcatca gagatggcag a                                            21

<210> SEQ ID NO 8
<211> LENGTH: 25
<212> TYPE: DNA
<213> ORGANISM: Artificial sequence
<220> FEATURE:
<223> OTHER INFORMATION: Synthetic construct

<400> SEQUENCE: 8
tgaacgaact gtatattcag caatg                                        25

<210> SEQ ID NO 9
<211> LENGTH: 20
<212> TYPE: DNA
<213> ORGANISM: Artificial sequence
<220> FEATURE:
<223> OTHER INFORMATION: Synthetic construct

<400> SEQUENCE: 9
agacccttgt gctcgttgtc                                              20

<210> SEQ ID NO 10
<211> LENGTH: 20
<212> TYPE: DNA
<213> ORGANISM: Artificial sequence
<220> FEATURE:
<223> OTHER INFORMATION: Synthetic construct

<400> SEQUENCE: 10
ttgttgggtg atcagagcag                                              20

<210> SEQ ID NO 11
<211> LENGTH: 19
<212> TYPE: DNA
<213> ORGANISM: Artificial sequence
<220> FEATURE:
<223> OTHER INFORMATION: Synthetic construct

<400> SEQUENCE: 11
gtccttgggg aacatggag                                               19

<210> SEQ ID NO 12
<211> LENGTH: 21
<212> TYPE: DNA
<213> ORGANISM: Artificial sequence
<220> FEATURE:
<223> OTHER INFORMATION: Synthetic construct

<400> SEQUENCE: 12
ttcagagaga caccagcaac a                                            21

<210> SEQ ID NO 13
<211> LENGTH: 21
<212> TYPE: DNA
<213> ORGANISM: Artificial sequence
<220> FEATURE:

```
<223> OTHER INFORMATION: Synthetic construct

<400> SEQUENCE: 13
aacaacatcc caactgtggt c                                              21

<210> SEQ ID NO 14
<211> LENGTH: 25
<212> TYPE: DNA
<213> ORGANISM: Artificial sequence
<220> FEATURE:
<223> OTHER INFORMATION: Synthetic construct

<400> SEQUENCE: 14
tccatattta tgaatggctt catct                                          25

<210> SEQ ID NO 15
<211> LENGTH: 19
<212> TYPE: DNA
<213> ORGANISM: Artificial sequence
<220> FEATURE:
<223> OTHER INFORMATION: Synthetic construct

<400> SEQUENCE: 15
agccacatcg ctcagacac                                                 19

<210> SEQ ID NO 16
<211> LENGTH: 19
<212> TYPE: DNA
<213> ORGANISM: Artificial sequence
<220> FEATURE:
<223> OTHER INFORMATION: Synthetic construct

<400> SEQUENCE: 16
gcccaatacg accaaatcc                                                 19
```

SMALL MOLECULE STIMULATORS OF STEROID RECEPTOR COACTIVATOR PROTEINS AND THEIR USE IN THE TREATMENT OF CANCER

CROSS REFERENCE TO PRIORITY APPLICATION

This application claims priority to U.S. Provisional Application No. 62/097,995, filed Dec. 30, 2014, which is incorporated herein by reference in its entirety.

STATEMENT REGARDING FEDERALLY FUNDED RESEARCH

This invention was made with government support under W81XWH-13-1-0285 awarded by the Department of Defense, and HD076596, awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jan. 11, 2022, is named 090464-1054092 seqlist.txt and is 3,377 bytes in size.

BACKGROUND

Members of the p160 steroid receptor coactivator (SRC) family, SRC-1, SRC-2/TIF2/GRIP1, and SRC-3/AM1/RAC3/ACTR/pCIP, interact with nuclear receptors and other transcription factors to drive target gene expression while also functioning as integrators of upstream cell signaling pathways. Although the proteins share homology with each other, they have distinct and important roles in multiple physiological processes, including growth and development, reproduction, and metabolism. All three proteins also have been found to be broadly involved in different aspects of tumorigenesis. SRC-3 is most well-known for its oncogenic role, whose gene is amplified in 9.5% of breast cancers and whose mRNA has been shown to be overexpressed in different breast cancer cohorts, often at the 50% level or greater. Clinically, SRC-3 overexpression in breast cancer correlates with larger tumor size, higher tumor grade, and poor survival rates. Direct evidence supporting SRC-3 as a bona fide oncogene comes from a MMTV-SRC-3 transgenic mouse model, in which overexpression of SRC-3 was sufficient to cause spontaneous development of malignant mammary tumors. SRC-3 overexpression also has been observed in endometrial, ovarian, prostate, colorectal, gastric, lung, pancreatic, and liver cancers. Additional in vitro and in vivo studies have bolstered the importance of SRC-3 in tumor initiation, progression, metastasis, and drug resistance. SRC-1 also is overexpressed in about 20% breast cancers and is positively correlated with ERBB2 expression, disease recurrence, and poor survival. It has been demonstrated that SRC-1 plays a critical role in cancer cell migration, invasion, and metastasis. Finally, SRC-2 has been proposed as a key oncogene in prostate cancer based on a comprehensive analysis on prostate tumors, cell lines, and xenografts, revealing that SRC-2 gene amplification and mutation specifically arise to levels of 38% in metastatic prostate tumors.

Although tumor formation is a multistage process involving activation of oncogenes and inactivation of tumor suppressors, loss of a specific oncogene can frequently reverse the malignant progression of cancer cells, suggesting that cancer cells rely on the continued activation or overexpression of an oncogene. This "oncogene addiction" theory, combined with the fact that SRC proteins integrate and promote multiple growth factor signaling pathways crucial for cancer cell growth and survival, highlights the potential value of SRC targeting drugs as future anti-cancer agents.

SUMMARY

Steroid receptor coactivator (SRC) stimulators and methods for their use in treating and/or preventing cancer are provided. The methods include administering to a subject a compound as described herein.

A method for treating cancer in a subject includes administering to the subject an effective amount of a compound of the following formula:

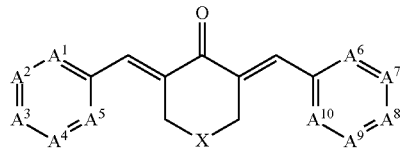

or a pharmaceutically acceptable salt or prodrug thereof. In the compounds for use in this method, $A^1$, $A^2$, $A^3$, $A^4$, $A^5$, $A^6$, $A^7$, $A^8$, $A^9$, and $A^{10}$ are each independently selected from $CR^1$ and N, wherein each $R^1$ is hydrogen, halogen, alkoxy, cyano, trifluoromethyl, or substituted or unsubstituted $C_{1-6}$ alkyl; and X is $CR^2R^3$, O, or $NR^4$, wherein $R^2$, $R^3$, and $R^4$ are each independently selected from the group consisting of hydrogen and substituted or unsubstituted $C_{1-6}$ alkyl. Optionally, the compound is

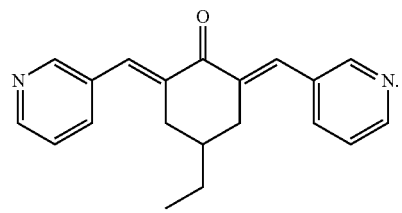 [SMILES: CCC1C/C(=C\c2cccnc2)C(=O)/C(=C/c2cccnc2)C1]

A method for treating cancer in a subject includes administering to the subject an effective amount of a compound of the following formula:

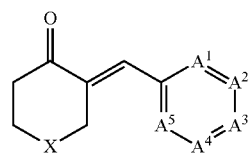

or a pharmaceutically acceptable salt or prodrug thereof. In the compounds for use in this method, $A^1$, $A^2$, $A^3$, $A^4$, and $A^5$ are each independently selected from $CR^1$ and N, wherein each $R^1$ is hydrogen, halogen, alkoxy, cyano, trifluoromethyl, or substituted or unsubstituted $C_{1-6}$ alkyl; and X is CR²R³, O, or NR⁴, wherein R², R³, and R⁴ are each independently selected from the group consisting of hydrogen and substituted or unsubstituted C$_{1-6}$ alkyl. Optionally, the compound is selected from the group consisting of:

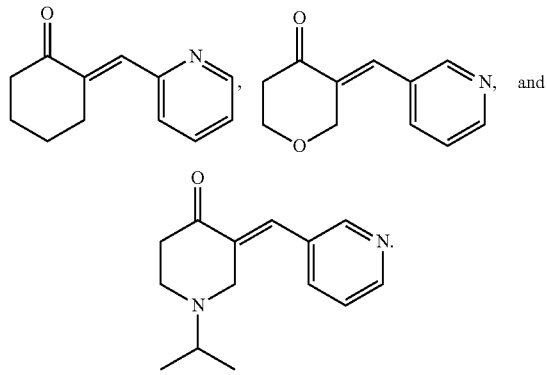

Optionally, the cancer is glioblastoma, such as a glioblastoma multiforme tumor. Optionally, the cancer is a pediatric glioblastoma multiforme tumor. Optionally, the cancer is breast cancer, liver cancer, lung cancer, pancreatic cancer, or prostate cancer.

Also described herein are methods of stimulating a steroid receptor coactivator protein in a cell. A method of stimulating a steroid receptor coactivator protein in a cell includes contacting a cell with an effective amount of a compound of the following formula:

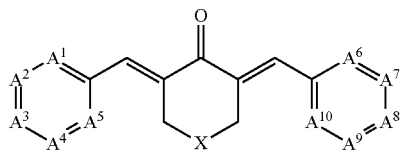

or a pharmaceutically acceptable salt or prodrug thereof. In the compounds for use in this method, A¹, A², A³, A⁴, A⁵, A⁶, A⁷, A⁸, A⁹, and A¹⁰ are each independently selected from CR¹ and N, wherein each R¹ is hydrogen, halogen, alkoxy, cyano, trifluoromethyl, or substituted or unsubstituted C$_{1-6}$ alkyl; and X is CR²R³, O, or NR⁴, wherein R², R³, and R⁴ are each independently selected from the group consisting of hydrogen and substituted or unsubstituted C$_{1-6}$ alkyl. Optionally, the compound is

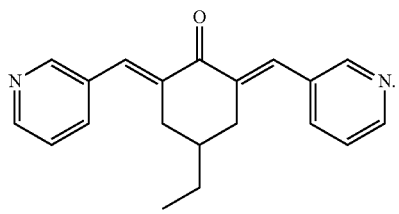 [SMILES: CCC1C/C(=C\c2cccnc2)C(=O)/C(=C/c2cccnc2)C1]

A method of stimulating a steroid receptor coactivator protein in a cell includes contacting a cell with an effective amount of a compound of the following formula:

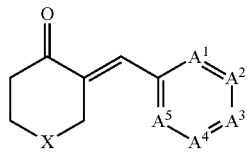

or a pharmaceutically acceptable salt or prodrug thereof. In the compounds for use in this method, A¹, A², A³, A⁴, and A⁵ are each independently selected from CR¹ and N, wherein each R¹ is hydrogen, halogen, alkoxy, cyano, trifluoromethyl, or substituted or unsubstituted C$_{1-6}$ alkyl; and X is CR²R³, O, or NR⁴, wherein R², R³, and R⁴ are each independently selected from the group consisting of hydrogen and substituted or unsubstituted C$_{1-6}$ alkyl. Optionally, the compound is selected from the group consisting of:

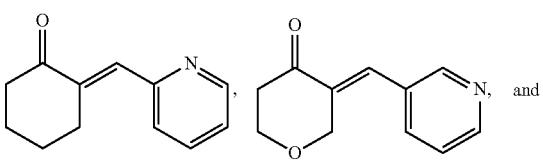

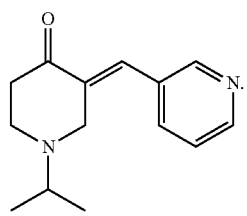

Optionally, the steroid receptor coactivator protein is SRC-1, SRC-2, or SRC-3. Optionally, the method of stimulating a steroid receptor coactivator protein in a cell is performed in vitro or in vivo.

Also described herein are compounds selected from the group consisting of:

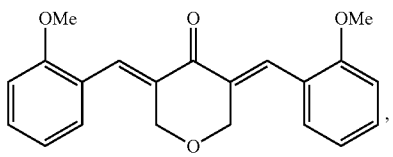

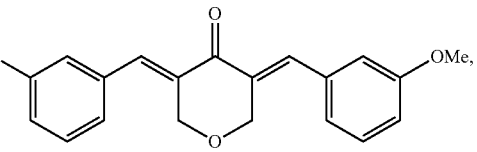

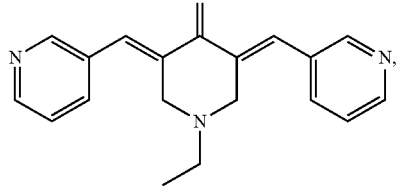

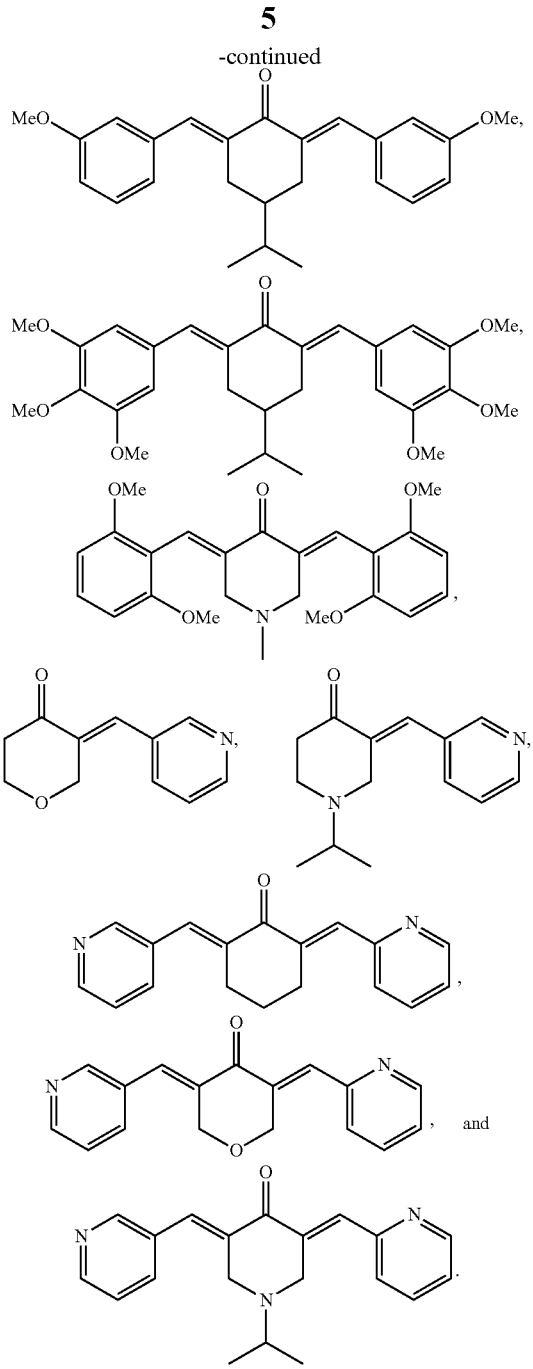

The details of one or more embodiments are set forth in the drawings and the description below. Other features, objects, and advantages will be apparent from the description and drawings, and from the claims.

DETAILED DESCRIPTION

Figure 1:
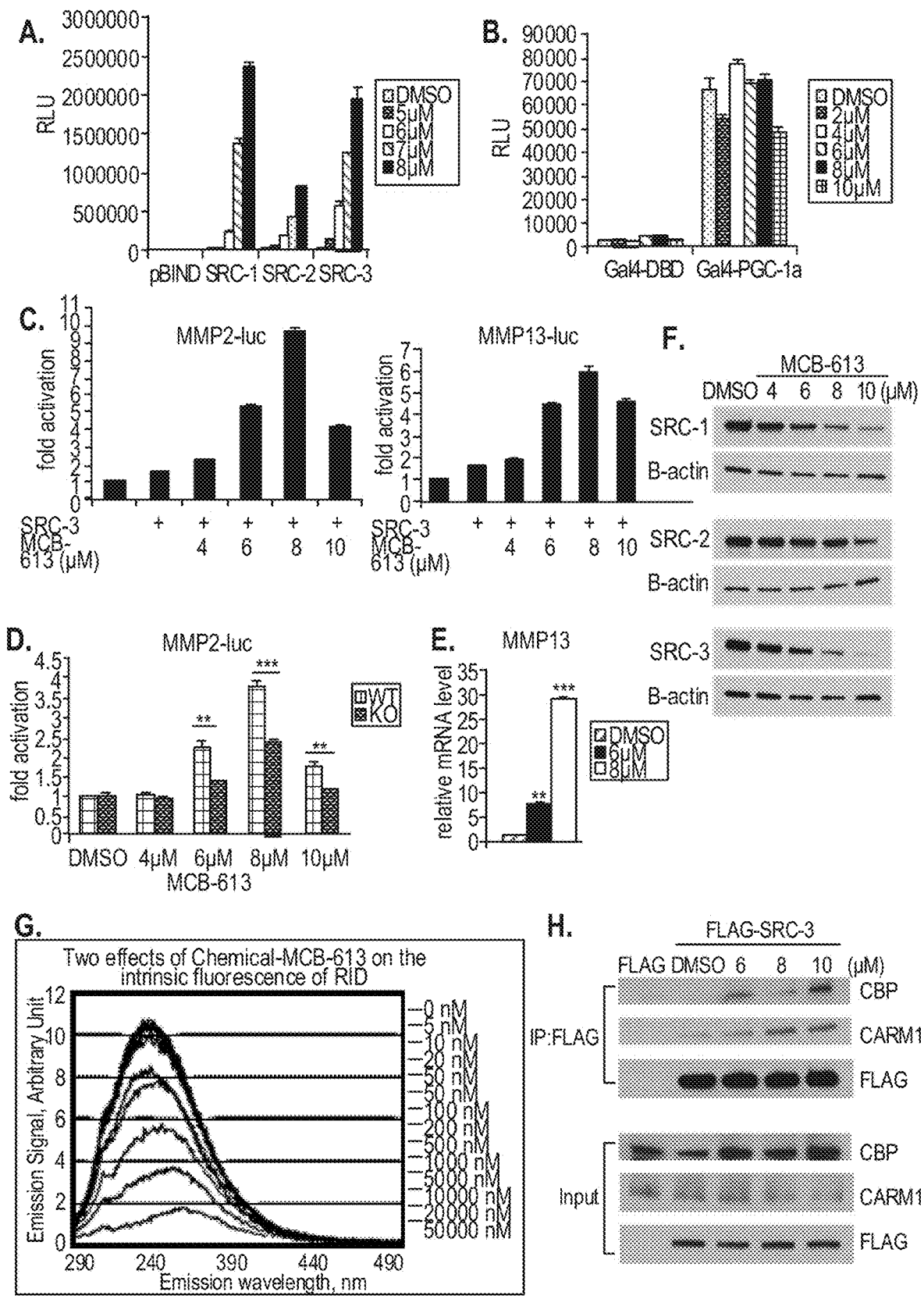
FIG. 1 shows that MCB-613 selectively activates the intrinsic transcriptional activity of SRCs. Panel A shows MCB-613 treatment increases the transcriptional activity of SRC-1, SRC-2 and SRC-3. HeLa cells co-transfected with the pG5-LUC luciferase reporter and pBIND-SRC-1/-2/-3 were treated with MCB-613 (5 μM, 6 μM, 7 μM, or 8 μM) for 24 hours. The bars for each of pBIND, SRC-1, SRC-2, and SRC-3 show the results for treatment with DMSO, 5 μM MCB-613, 6 μM MCB-613, 7 μM MCB-613, and 8 μM MCB-613, from left to right. Panel B shows MCB-613 does not activate PGC-1α. HeLa cells were co-transfected with Gal4-PGC-1α and pG5-LUC and assayed as in A. The bars show the results for treatment with DMSO, 2 μM MCB-613, 4 μM MCB-613, 6 μM MCB-613, 8 μM MCB-613, and 10 μM MCB-613, from left to right. Panel C shows MCB-613 enhances SRC-3's coactivation of transcription from the MMP2 and MMP13 promoters. HeLa cells were co-transfected with an expression vector for SRC-3 and MMP2-luc or MMP13-luc reporter, followed by treatment and luciferase assay as in A. Panel D shows MMP2 promoter activation by MCB-613 is SRC-3-dependent. SRC-3 WT or KO HeLa cells transfected with MMP2-luc were treated with MCB-613 for 24 hours. Panel E shows MCB-613 activates endogenous SRC-3 target gene expression. qRT-PCR of MMP13 is shown for MDA-MB-231 cells treated with MCB-613 for 24 hours. Panel F shows SRC activation by MCB-613 is not due to increased protein levels. HeLa cells treated with MCB-613 for 24 hours were immunoblotted for SRC-1, SRC-2 and SRC-3. Panel G shows MCB-613 directly binds to the receptor interacting domain (RID) of SRC-3. Direct interaction between MCB-613 and SRC-3 was determined by fluorescence spectroscopy. Panel H shows MCB-613 increases interaction between SRC-3 and other coactivators. HeLa cells overexpressing FLAG or FLAG-SRC-3 were subject to MCB-613 treatment for 1 hour before coIP. Data are represented as mean±SEM. P<0.01, *P<0.001.

Described herein are steroid receptor coactivator (SRC) stimulators and methods for their use. Specifically, the small molecules described herein are stimulators of one or more of the SRC family protein members, including SRC-1, SRC-2/TIF2/GRIP1, and SRC-3/AIB1/RAC3/ACTR/pCIP. The compounds and methods described herein are useful for treating cancer, including glioblastoma multiforme tumors. As detailed herein, acute super-activation of SRC coactivators effectively kills cancer cells by inducing aberrant cellular stress. The over-stimulation of the SRC family proteins is an unexpected but effective approach to selectively kill cancer cells whose cellular stress response pathways already are maximally engaged.

I. Compounds

A class of SRC stimulators described herein is represented by Formula I:

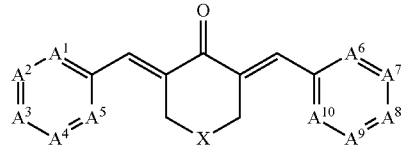

and pharmaceutically acceptable salts or prodrugs thereof.

In Formula I, $A^1$, $A^2$, $A^3$, $A^4$, $A^5$, $A^6$, $A^7$, $A^8$, $A^9$, and $A^{10}$ are each independently selected from $CR^1$ and N. Each $R^1$ group present in Formula I is independently selected from hydrogen, halogen, alkoxy, cyano, trifluoromethyl, and substituted or unsubstituted $C_{1-6}$ alkyl.

Also, in Formula I, X is $CR^2R^3$, O, or $NR^4$. $R^2$, $R^3$, and $R^4$ are each independently selected from the group consisting of hydrogen and substituted or unsubstituted $C_{1-6}$ alkyl.

As used herein, the terms alkyl, alkenyl, and alkynyl include straight- and branched-chain monovalent substituents. Examples include methyl, ethyl, isobutyl, 3-butynyl, and the like. Ranges of these groups useful with the compounds and methods described herein include $C_1$-$C_{20}$ alkyl, $C_2$-$C_{20}$ alkenyl, and $C_2$-$C_{20}$ alkynyl. Additional ranges of these groups useful with the compounds and methods described herein include $C_1$-$C_{12}$ alkyl, $C_2$-$C_{12}$ alkenyl, $C_2$-$C_{12}$ alkynyl, $C_1$-$C_6$ alkyl, $C_2$-$C_6$ alkenyl, $C_2$-$C_6$ alkynyl, $C_1$-$C_4$ alkyl, $C_2$-$C_4$ alkenyl, and $C_2$-$C_4$ alkynyl.

Heteroalkyl, heteroalkenyl, and heteroalkynyl are defined similarly as alkyl, alkenyl, and alkynyl, but can contain O, S, or N heteroatoms or combinations thereof within the backbone. Ranges of these groups useful with the compounds and methods described herein include $C_1$-$C_{20}$ heteroalkyl, $C_2$-$C_{20}$ heteroalkenyl, and $C_2$-$C_{20}$ heteroalkynyl. Additional ranges of these groups useful with the compounds and methods described herein include $C_1$-$C_{12}$ heteroalkyl, $C_2$-$C_{12}$ heteroalkenyl, $C_2$-$C_{12}$ heteroalkynyl, $C_1$-$C_6$ heteroalkyl, $C_2$-$C_6$ heteroalkenyl, $C_2$-$C_6$ heteroalkynyl, heteroalkyl, $C_2$-$C_4$ heteroalkenyl, and $C_2$-$C_4$ heteroalkynyl.

The terms cycloalkyl, cycloalkenyl, and cycloalkynyl include cyclic alkyl groups having a single cyclic ring or multiple condensed rings. Examples include cyclohexyl, cyclopentylethyl, and adamantanyl. Ranges of these groups useful with the compounds and methods described herein include $C_3$-$C_{20}$ cycloalkyl, $C_3$-$C_{20}$ cycloalkenyl, and $C_3$-$C_{20}$ cycloalkynyl. Additional ranges of these groups useful with the compounds and methods described herein include $C_5$-$C_{12}$ cycloalkyl, $C_5$-$C_{12}$ cycloalkenyl, $C_5$-$C_{12}$ cycloalkynyl, $C_5$-$C_6$ cycloalkyl, $C_5$-$C_6$ cycloalkenyl, and $C_5$-$C_6$ cycloalkynyl.

The terms heterocycloalkyl, heterocycloalkenyl, and heterocycloalkynyl are defined similarly as cycloalkyl, cycloalkenyl, and cycloalkynyl, but can contain O, S, or N heteroatoms or combinations thereof within the cyclic backbone. Ranges of these groups useful with the compounds and methods described herein include $C_3$-$C_{20}$ heterocycloalkyl, $C_3$-$C_{20}$ heterocycloalkenyl, and $C_3$-$C_{20}$ heterocycloalkynyl. Additional ranges of these groups useful with the compounds and methods described herein include $C_5$-$C_{12}$ heterocycloalkyl, $C_5$-$C_{12}$ heterocycloalkenyl, $C_5$-$C_{12}$ heterocycloalkynyl, $C_5$-$C_6$ heterocycloalkyl, $C_5$-$C_6$ heterocycloalkenyl, and $C_5$-$C_6$ heterocycloalkynyl.

Aryl molecules include, for example, cyclic hydrocarbons that incorporate one or more planar sets of, typically, six carbon atoms that are connected by delocalized electrons numbering the same as if they consisted of alternating single and double covalent bonds. An example of an aryl molecule is benzene. Heteroaryl molecules include substitutions along their main cyclic chain of atoms such as O, N, or S. When heteroatoms are introduced, a set of five atoms, e.g., four carbon and a heteroatom, can create an aromatic system. Examples of heteroaryl molecules include furan, pyrrole, thiophene, imadazole, oxazole, pyridine, and pyrazine. Aryl and heteroaryl molecules can also include additional fused rings, for example, benzofuran, indole, benzothiophene, naphthalene, anthracene, and quinoline. The aryl and heteroaryl molecules can be attached at any position on the ring, unless otherwise noted.

The term alkoxy as used herein is an alkyl group bound through a single, terminal ether linkage. Likewise, the term aryloxy as used herein is an aryl group bound through a single, terminal ether linkage.

The term hydroxyl as used herein is represented by the formula —OH.

The terms amine or amino as used herein are represented by the formula —$NZ^1Z^2$, where $Z^1$ and $Z^2$ can each be a substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above.

The alkoxy, aryloxy, amino, alkyl, alkenyl, alkynyl, aryl, heteroalkyl, heteroalkenyl, heteroalkynyl, heteroaryl, cycloalkyl, or heterocycloalkyl molecules used herein can be substituted or unsubstituted. As used herein, the term substituted includes the addition of an alkoxy, aryloxy, amino, alkyl, alkenyl, alkynyl, aryl, heteroalkyl, heteroalkenyl, heteroalkynyl, heteroaryl, cycloalkyl, or heterocycloalkyl group to a position attached to the main chain of the alkoxy, aryloxy, amino, alkyl, alkenyl, alkynyl, aryl, heteroalkyl, heteroalkenyl, heteroalkynyl, heteroaryl, cycloalkyl, or heterocycloalkyl, e.g., the replacement of a hydrogen by one of these molecules. Examples of substitution groups include, but are not limited to, hydroxyl, halogen (e.g., F, Br, Cl, or I), and carboxyl groups. Conversely, as used herein, the term unsubstituted indicates the alkoxy, aryloxy, amino, alkyl, alkenyl, alkynyl, aryl, heteroalkyl, heteroalkenyl, heteroalkynyl, heteroaryl, cycloalkyl, or heterocycloalkyl has a full complement of hydrogens, i.e., commensurate with its saturation level, with no substitutions, e.g., linear decane (—$(CH_2)_9$—$CH_3$).

In some examples, Formula I is represented by Structure I-A:

Structure I-A

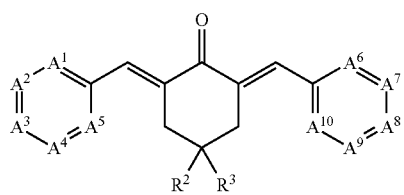

In Structure I-A, $A^1$, $A^2$, $A^3$, $A^4$, $A^5$, $A^6$, $A^7$, $A^8$, $A^9$, $A^{10}$, $R^2$, and $R^3$ are as defined above for Formula I. In some examples of Structure I-A, each of $A^1$, $A^2$, $A^3$, $A^4$, $A^5$, $A^6$, $A^7$, $A^8$, $A^9$, and $A^{10}$ are $CR^1$, where each $R^1$ is independently selected from a group as defined above for Formula I. For example, the compound of Structure I-A can be represented by Structure I-A1:

Structure I-A1

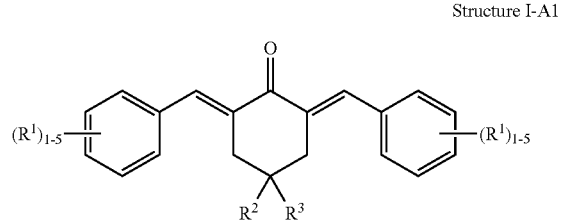

In Structure I-A1, the phenyl rings of the molecule can each independently include from one to five $R^1$ groups. Each of the $R^1$ groups can be independently selected from a group as defined above for Formula I.

In some examples of Structure I-A, one or more of $A^1$, $A^2$, $A^3$, $A^4$, $A^5$, $A^6$, $A^7$, $A^8$, $A^9$, and $A^{10}$ can be N. For example, the compound of Structure I-A can be represented by Structure I-A2, Structure I-A3, or Structure I-A4:

Structure I-A2

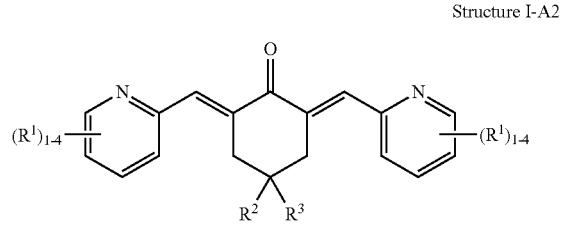

Structure I-A3

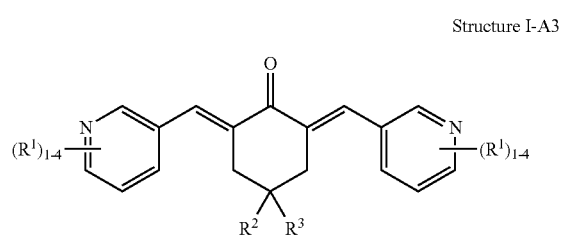

Structure I-A4

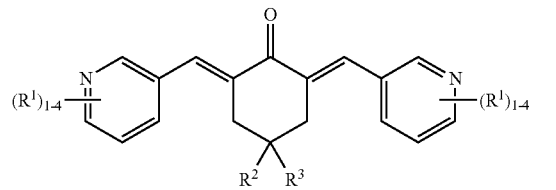

In Structure I-A2, Structure I-A3, and Structure I-A4, the phenyl rings of the molecule can each independently include from one to four $R^1$ groups. Each of the $R^1$ groups can be independently selected from a group as defined above for Formula I.

In some examples, Formula I is represented by Structure I-B:

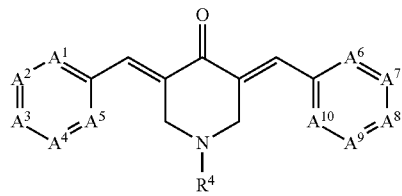
Structure I-B

In Structure I-B, $A^1$, $A^2$, $A^3$, $A^4$, $A^5$, $A^6$, $A^7$, $A^8$, $A^9$, $A^{10}$, and $R^4$ are as defined above for Formula I. In some examples of Structure I-B, each of $A^1$, $A^2$, $A^3$, $A^4$, $A^5$, $A^6$, $A^7$, $A^8$, $A^9$, and $A^{10}$ are $CR^1$, where each $R^1$ is independently selected from a group as defined above for Formula I. For example, the compound of Structure I-B can be represented by Structure I-B1:

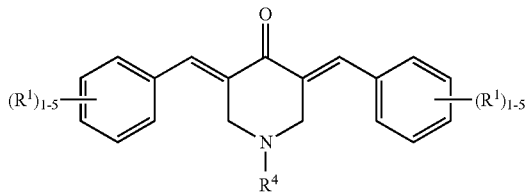
Structure I-B1

In Structure I-B1, the phenyl rings of the molecule can include from one to five $R^1$ groups. Each of the $R^1$ groups can be independently selected from a group as defined above for Formula I.

In some examples of Structure I-B, one or more of $A^1$, $A^2$, $A^3$, $A^4$, $A^5$, $A^6$, $A^7$, $A^8$, $A^9$, and $A^{10}$ can be N. For example, the compound of Structure I-B can be represented by Structure I-B2, Structure I-B3, or Structure I-B4:

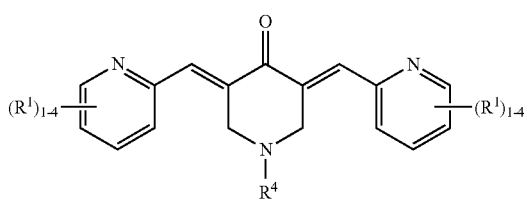
Structure I-B2

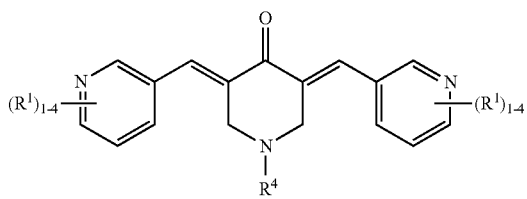
Structure I-B3

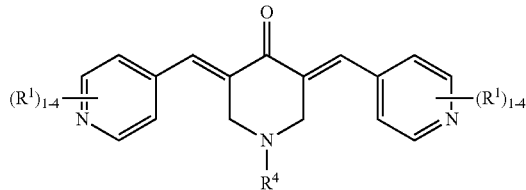
Structure I-B4

In Structure I-B2, Structure I-B3, and Structure I-B4, the phenyl rings of the molecule can each independently include from one to four $R^1$ groups. Each of the $R^1$ groups can be independently selected from a group as defined above for Formula I.

In some examples, Formula I is represented by Structure I-C:

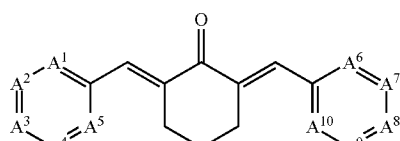
Structure I-C

In Structure I-C, $A^1$, $A^2$, $A^3$, $A^4$, $A^5$, $A^6$, $A^7$, $A^8$, $A^9$, and $A^{10}$ are as defined above for Formula I. In some examples of Structure I-C, each of $A^1$, $A^2$, $A^3$, $A^4$, $A^5$, $A^6$, $A^7$, $A^8$, $A^9$, and $A^{10}$ are $CR^1$, where each $R^1$ is independently selected from a group as defined above for Formula I. For example, the compound of Structure I-C can be represented by Structure I-C1:

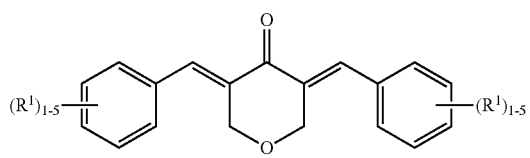
Structure I-C1

In Structure I-C1, the phenyl rings of the molecule can include from one to five $R^1$ groups. Each of the $R^1$ groups can be independently selected from a group as defined above for Formula I.

In some examples of Structure I-C, one or more of $A^1$, $A^2$, $A^3$, $A^4$, $A^5$, $A^6$, $A^7$, $A^8$, $A^9$, and $A^{10}$ can be N. For example, the compound of Structure I-C can be represented by Structure I-C2, Structure I-C3, or Structure I-C4:

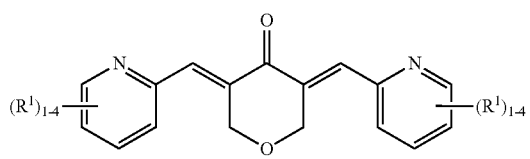
Structure I-C2

Structure I-C3

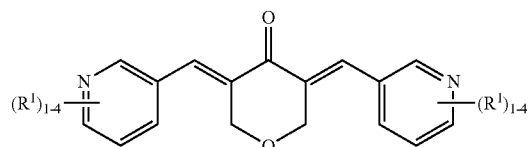

Structure I-C4

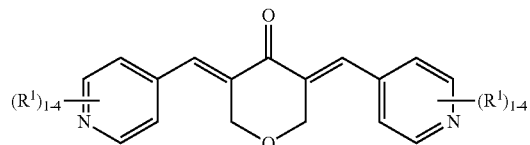

In Structure I-C2, Structure I-C3, and Structure I-C4, the phenyl rings of the molecule can each independently include from one to four $R^1$ groups. Each of the $R^1$ groups can be independently selected from a group as defined above for Formula I.

Examples of Formula I include the following compounds:

SYC-929

(Compound 1-1)

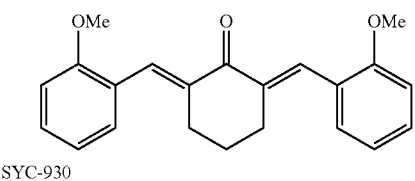

SYC-930

(Compound 1-2)

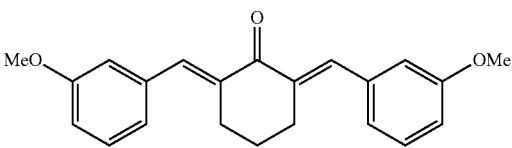

SYC-931

(Compound 1-3)

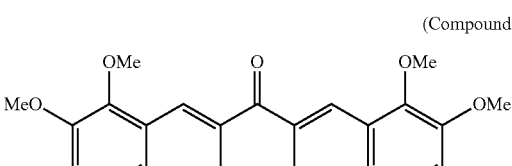

SYC-932

(Compound 1-4)

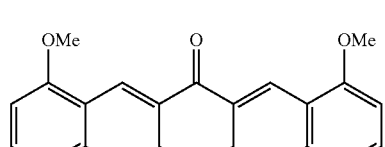

SYC-933

(Compound 1-5)

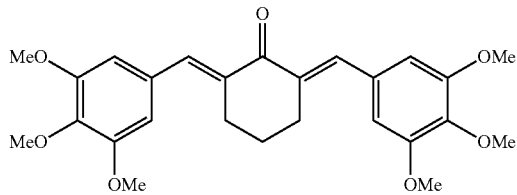

SYC-934

(Compound 1-6)

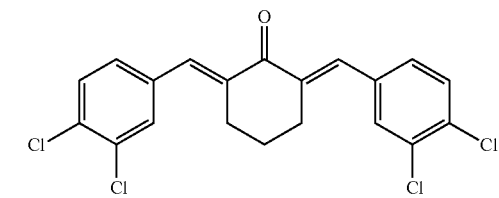

SYC-935

(Compound 1-7)

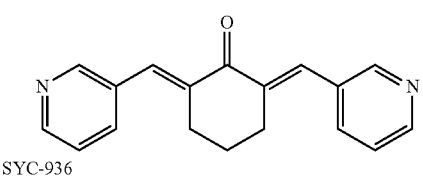

SYC-907

(Compound 1-8)

SYC-936

(Compound 1-9)

SYC-937

(Compound 2-1)

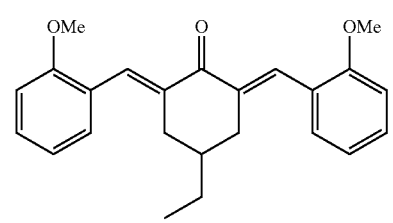

SYC-938
(Compound 2-2)
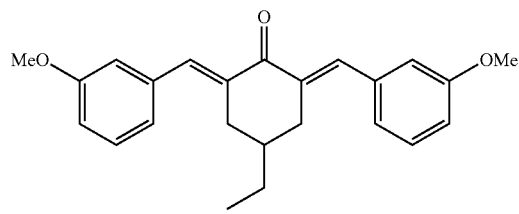
SYC-939
(Compound 2-3)
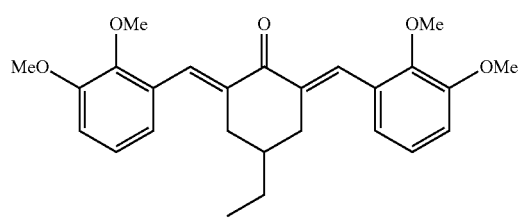
SYC-940
(Compound 2-4)
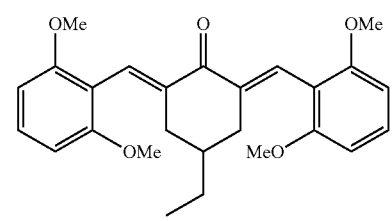
SYC-941
(Compound 2-5)
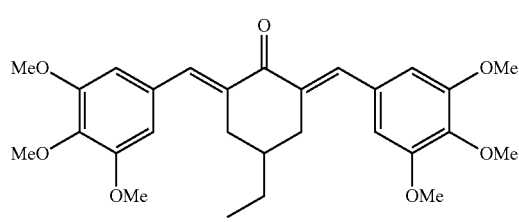
SYC-942
(Compound 2-6)
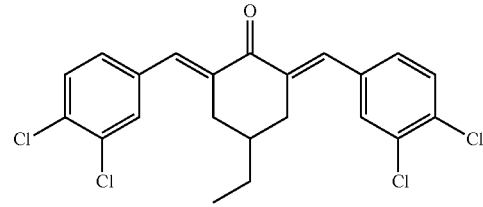
SYC-943
(Compound 2-7)
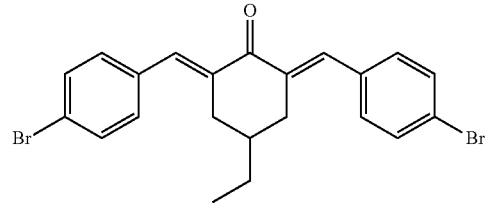
SYC-944 (or MCB-613)
(Compound 2-8)
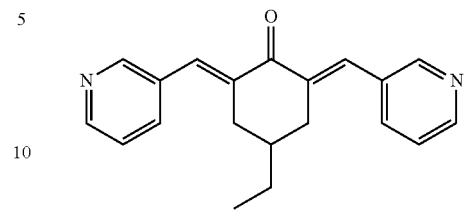
SYC-908
(Compound 2-9)
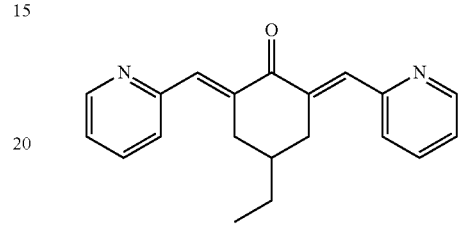
SYC-945
(Compound 3-1)
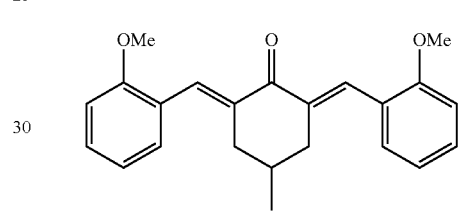
SYC-946
(Compound 3-2)
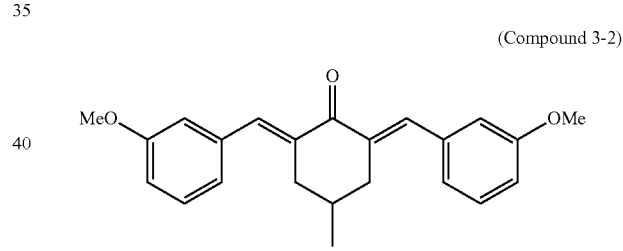
SYC-947
(Compound 3-3)
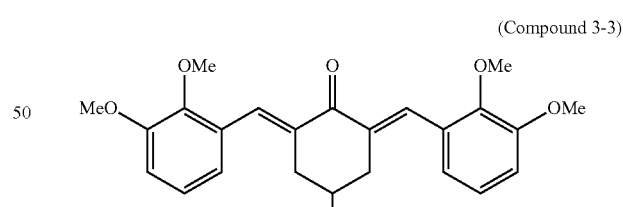
SYC-948
(Compound 3-4)
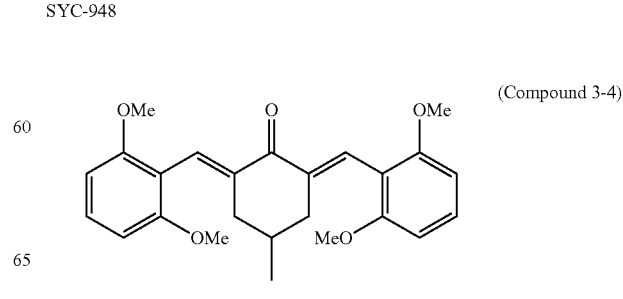

SYC-949
(Compound 3-5)
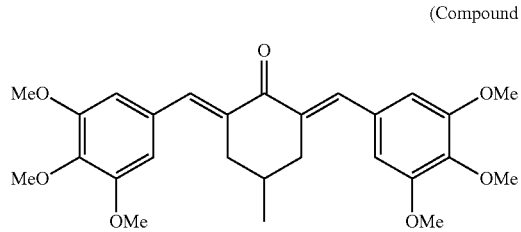
SYC-950
(Compound 3-6)
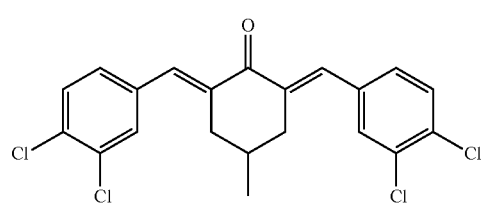
SYC-951
(Compound 3-7)
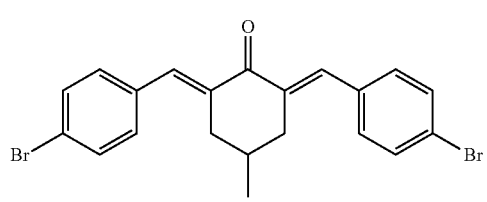
SYC-909
(Compound 3-8)
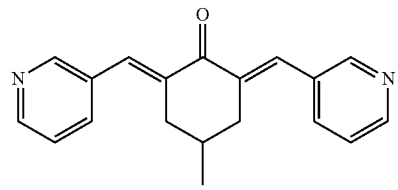
SYC-952
(Compound 3-9)
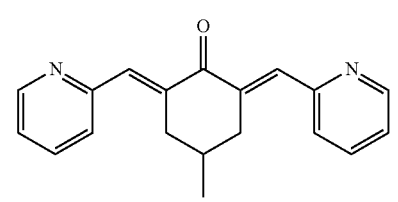
SYC-849
(Compound 4-1)
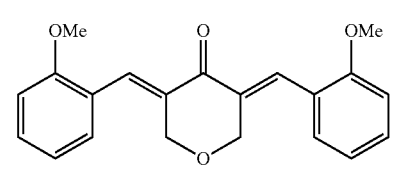
SYC-850
(Compound 4-2)
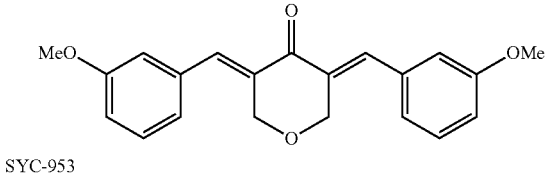
SYC-953
(Compound 4-3)
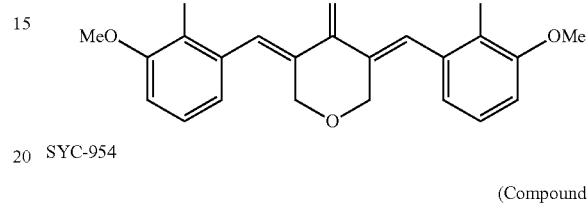
SYC-954
(Compound 4-4)
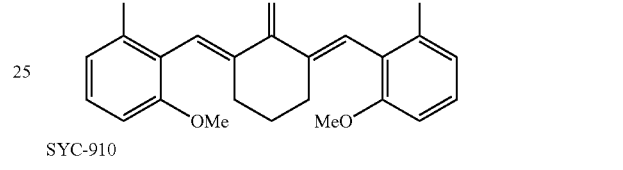
SYC-910
(Compound 4-5)
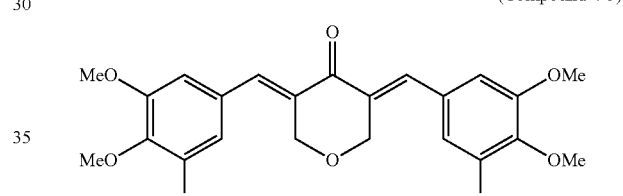
SYC-955
(Compound 4-6)
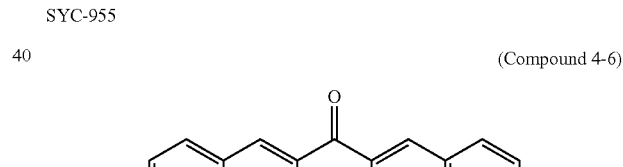
SYC-956
(Compound 4-7)
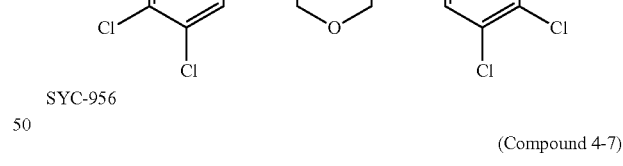
SYC-851
(Compound 4-8)
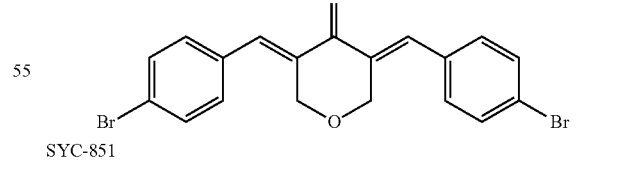

SYC-957
(Compound 4-9)
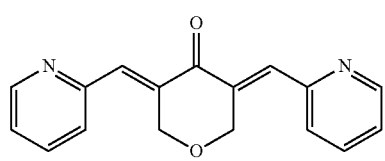
SYC-852
(Compound 5-1)
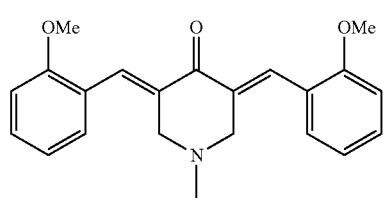
SYC-958
(Compound 5-2)
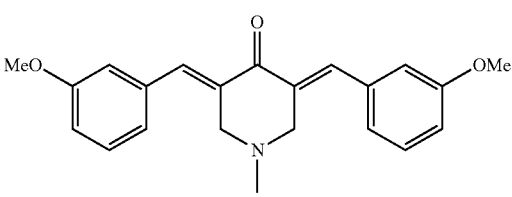
SYC-911
(Compound 5-3)
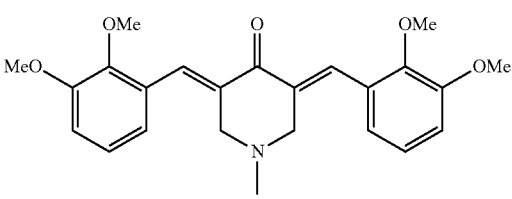
SYC-853
(Compound 5-4)
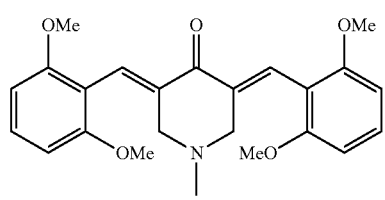
SYC-912
(Compound 5-5)
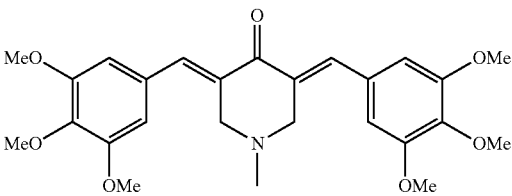
SYC-959
(Compound 5-6)
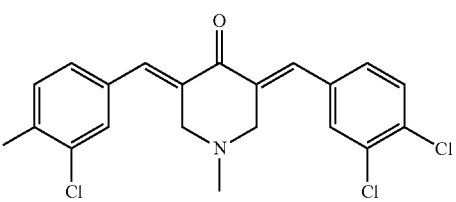
SYC-960
(Compound 5-7)
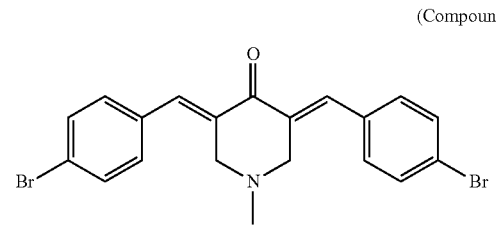
SYC-928
(Compound 5-8)
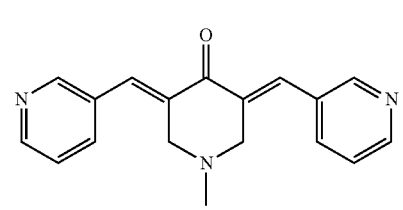
SYC-913
(Compound 5-9)
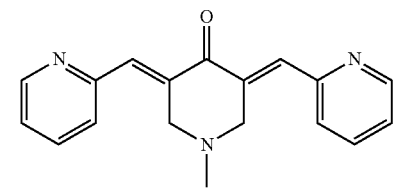
SYC-961
(Compound 6-1)
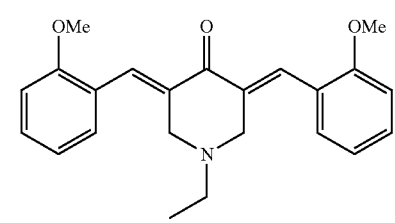
SYC-962
(Compound 6-2)
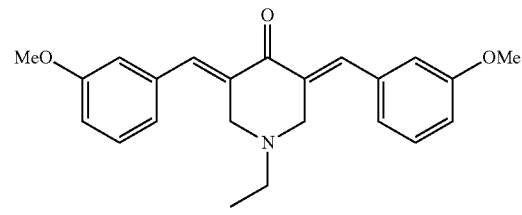

SYC-963
(Compound 6-3)
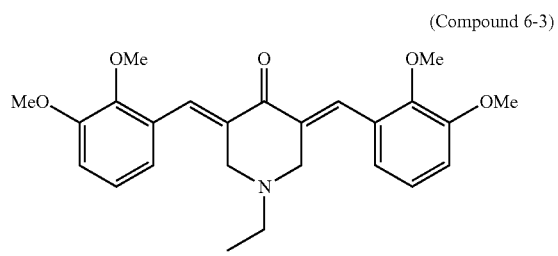
SYC-964
(Compound 6-4)
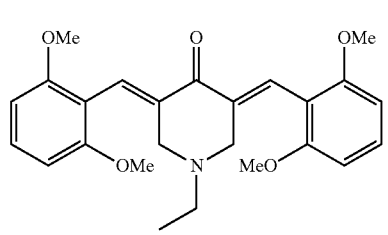
SYC-914
(Compound 6-5)
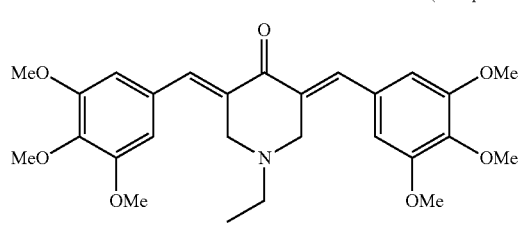
SYC-965
(Compound 6-6)
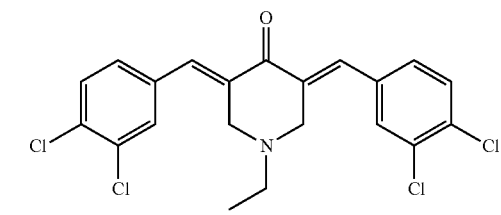
SYC-966
(Compound 6-7)
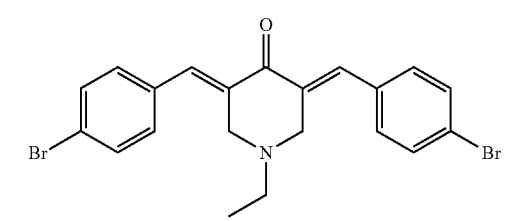
SYC-854
(Compound 6-8)
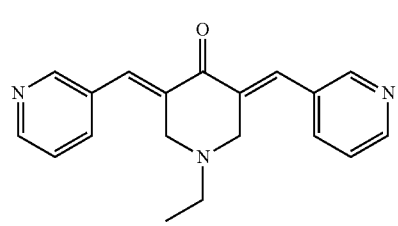
SYC-915
(Compound 6-9)
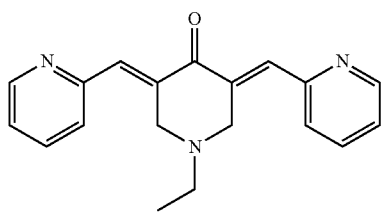
SYC-967
(Compound 7-1)
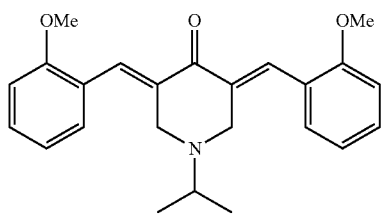
SYC-968
(Compound 7-2)
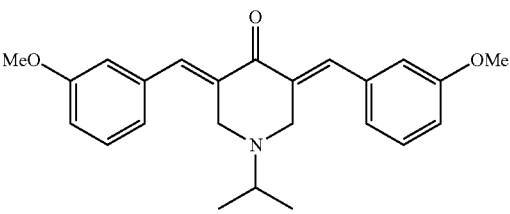
SYC-920
(Compound 7-3)
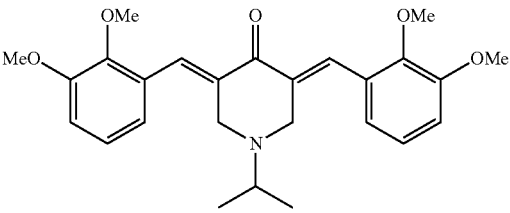
SYC-969
(Compound 7-4)
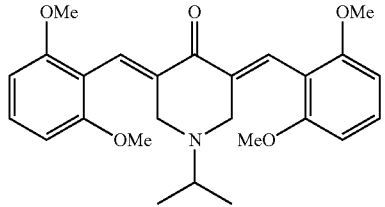
SYC-921
(or Compound 7-5)
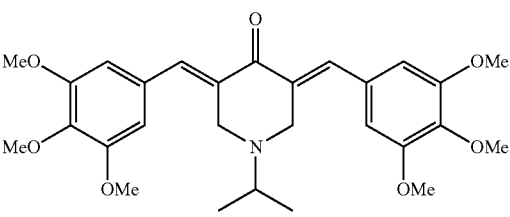

25
-continued
SYC-970
(Compound 7-6)
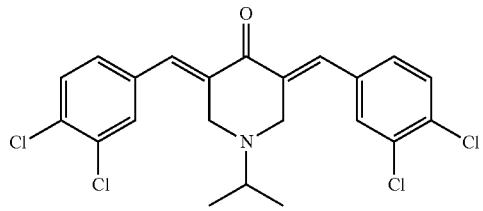
SYC-971
(Compound 7-7)
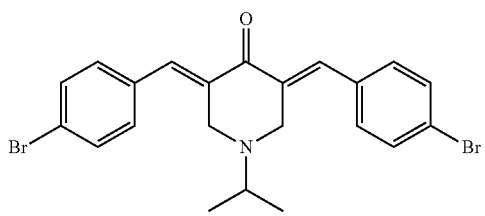
SYC-855
(Compound 7-8)
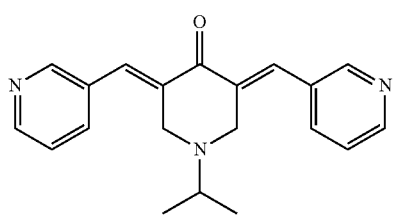
SYC-916
(Compound 7-9)
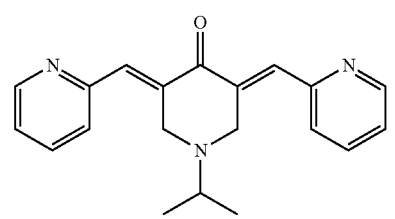
26
-continued
SYC-973
(Compound 8-3)
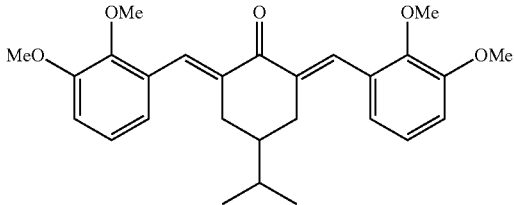
SYC-974
(Compound 8-4)
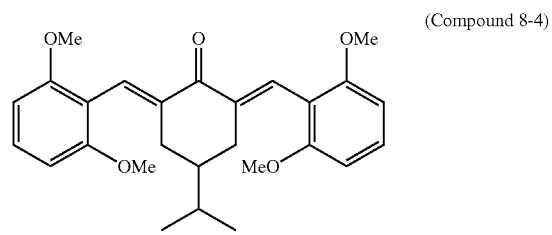
SYC-857
(Compound 8-5)
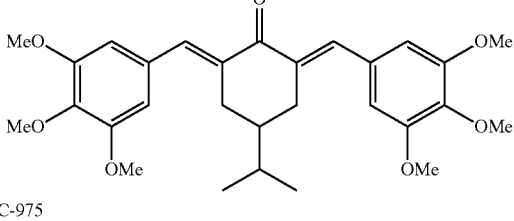
SYC-975
(Compound 8-6)
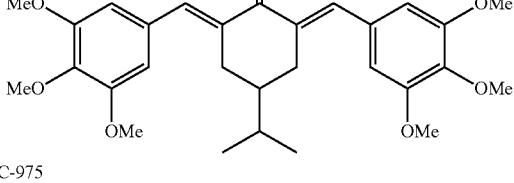
SYC-972
(Compound 8-1)
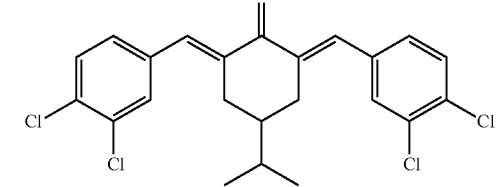
SYC-976
(Compound 8-7)
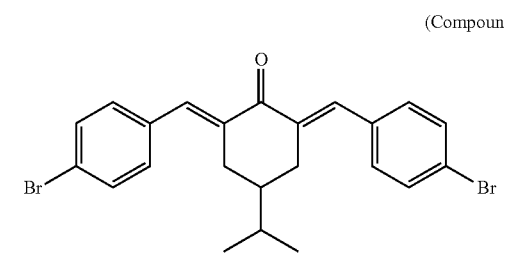
SYC-856
(Compound 8-2)
SYC-977
(Compound 8-8)
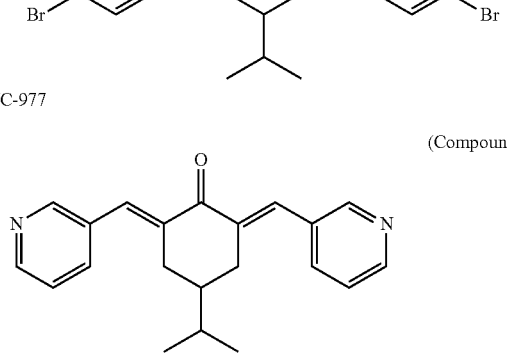

-continued

SYC-919 (Compound 8-9)

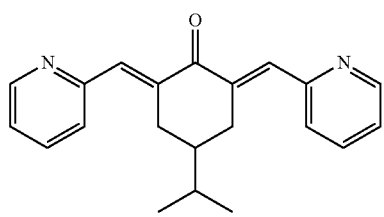

Compound S2

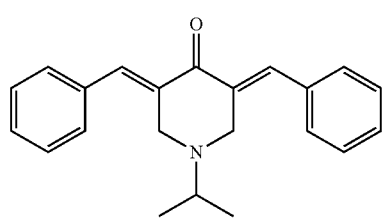

Compound S3

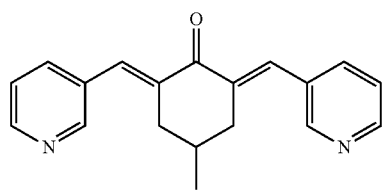

Compound S15

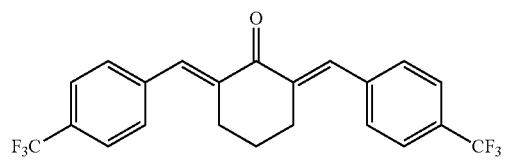

Compound S18

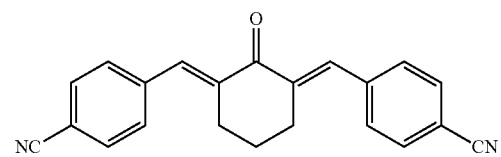

SYC-923 (Compound 1-8-2)

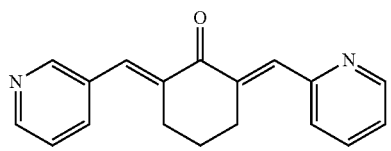

SYC-925 (Compound 4-8-2)

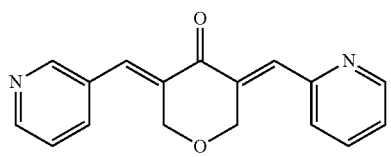

-continued

SYC-927 (Compound 7-8-2)

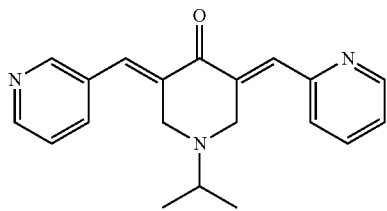

SYC-917 (Compound 7-18)

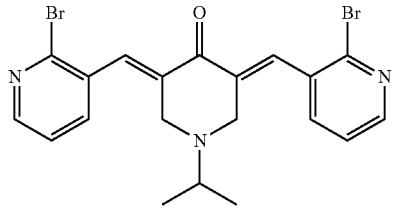

SYC-918 (Compound 7-19)

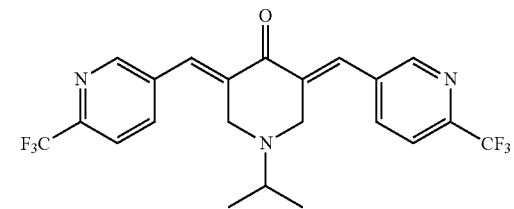

In some embodiments, the compound is SYC-930 (Compound 1-2), SYC-936 (Compound 1-9), SYC-944 (Compound 2-8) (also referred to herein as MCB-613), SYC-946 (Compound 3-2), SYC-909 (Compound 3-8), SYC-952 (Compound 3-9), SYC-849 (Compound 4-1), SYC-850 (Compound 4-2), SYC-851 (Compound 4-8), SYC-957 (Compound 4-9), SYC-852 (Compound 5-1), SYC-853 (Compound 5-4), SYC-960 (Compound 5-7), SYC-965 (Compound 6-6), SYC-966 (Compound 6-7), SYC-854 (Compound 6-8), SYC-970 (Compound 7-6), SYC-855 (Compound 7-8), SYC-856 (Compound 8-2), or SYC-857 (Compound 8-5). In some embodiments, the compound is SYC-923 (Compound 1-8-2), SYC-925 (Compound 4-8-2), SYC-927 (Compound 7-8-2), SYC-917 (Compound 7-18), or SYC-918 (Compound 7-19). In some embodiments, the compound is not SYC-944 (Compound 2-8) (also referred to herein as MCB-613).

A class of SRC stimulators described herein is represented by Formula II:

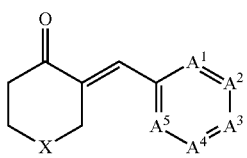

and pharmaceutically acceptable salts or prodrugs thereof.

In Formula II, $A^1$, $A^2$, $A^3$, $A^4$, and $A^5$ are each independently selected from $CR^1$ and N. Each $R^1$ group present in Formula II is independently selected from hydrogen, halogen, alkoxy, cyano, trifluoromethyl, and substituted or unsubstituted $C_{1-6}$ alkyl.

Also, in Formula II, X is $CR^2R^3$, O, or $NR^4$. $R^2$, $R^3$, and $R^4$ are each independently selected from the group consisting of hydrogen and substituted or unsubstituted $C_{1-6}$ alkyl.

Examples of Formula II include the following compounds:

SYC-922

(Compound 1-8-1)

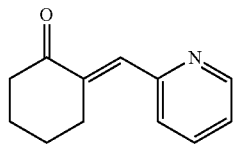

SYC-924

(Compound 4-8-1)

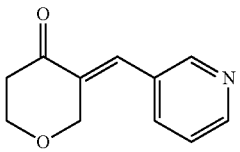

SYC-926

(Compound 7-8-1)

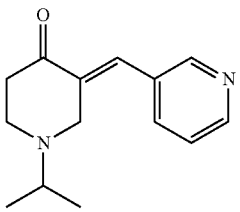

II. Methods of Making the Compounds

The compounds described herein can be prepared in a variety of ways. The compounds can be synthesized using various synthetic methods. At least some of these methods are known in the art of synthetic organic chemistry. The compounds described herein can be prepared from readily available starting materials. Optimum reaction conditions can vary with the particular reactants or solvent used, but such conditions can be determined by one skilled in the art by routine optimization procedures.

Variations on Formulas I and II include the addition, subtraction, or movement of the various constituents as described for each compound. Similarly, when one or more chiral centers are present in a molecule, all possible chiral variants are included. Additionally, compound synthesis can involve the protection and deprotection of various chemical groups. The use of protection and deprotection, and the selection of appropriate protecting groups can be determined by one skilled in the art. The chemistry of protecting groups can be found, for example, in Greene, et al., Protective Groups in Organic Synthesis, 2d. Ed., Wiley & Sons, 1991, which is incorporated herein by reference in its entirety.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high performance liquid chromatography (HPLC) or thin layer chromatography.

Exemplary methods for synthesizing compounds as described herein are provided in Example 1 below.

III. Pharmaceutical Formulations

The compounds described herein or derivatives thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the compound described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers, such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers, such as polyvinylpyrrolidone; amino acids such as glycine, glutamine, asparagine, arginine or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN® (ICI, Inc.; Bridgewater, N.J.), polyethylene glycol (PEG), and PLURONICS™ (BASF; Florham Park, N.J.).

Compositions containing the compound described herein or derivatives thereof suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants, such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier), such as sodium citrate or dicalcium phosphate, or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, may contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or derivatives thereof for rectal administrations are optionally suppositories, which can be prepared by mixing the compounds with suitable non-irritating excipients or carriers, such as cocoa butter, polyethyleneglycol or a suppository wax, which are solid at ordinary temperatures but liquid at body temperature and, therefore, melt in the rectum or vaginal cavity and release the active component.

Dosage forms for topical administration of the compounds described herein or derivatives thereof include ointments, powders, sprays, and inhalants. The compounds described herein or derivatives thereof are admixed under sterile conditions with a physiologically acceptable carrier and any preservatives, buffers, or propellants as may be required. Ophthalmic formulations, ointments, powders, and solutions are also contemplated as being within the scope of the compositions.

The compositions can include one or more of the compounds described herein and a pharmaceutically acceptable carrier. As used herein, the term pharmaceutically acceptable salt refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., J. Pharm. Sci. (1977) 66, 1, which is incorporated herein by reference in its entirety, at least, for compositions taught therein.)

Administration of the compounds and compositions described herein or pharmaceutically acceptable salts thereof can be carried out using therapeutically effective amounts of the compounds and compositions described herein or pharmaceutically acceptable salts thereof as described herein for periods of time effective to treat a disorder. The effective amount of the compounds and compositions described herein or pharmaceutically acceptable salts thereof as described herein may be determined by one of ordinary skill in the art and includes exemplary dosage amounts for a mammal of from about 0.5 to about 200 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.01 to about 50 mg/kg of body weight of active compound per day, about 0.05 to about 25 mg/kg of body weight of active compound per day, about 0.1 to about 25 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, about 5 mg/kg of body weight of active compound per day, about 2.5 mg/kg of body weight of active compound per day, about 1.0 mg/kg of body weight of active compound per day, or about 0.5 mg/kg of body weight of active compound per day, or any range derivable therein. Optionally, the dosage amounts are from about 0.01 mg/kg to about 10 mg/kg of body weight of active compound per day. Optionally, the dosage amount is from about 0.01 mg/kg to about 5 mg/kg. Optionally, the dosage amount is from about 0.01 mg/kg to about 2.5 mg/kg.

Those of skill in the art will understand that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

The precise dose to be employed in the formulation will also depend on the route of administration, and the seriousness of the disease or disorder, and should be decided according to the judgment of the practitioner and each subject's circumstances. Effective doses can be extrapolated from dose-response curves derived from in vitro or animal model test systems. Further, depending on the route of administration, one of skill in the art would know how to determine doses that result in a plasma concentration for a desired level of response in the cells, tissues and/or organs of a subject.

IV. Methods of Use

Provided herein are methods to treat, prevent, or ameliorate a steroid receptor coactivator-related disease in a subject. Optionally, the steroid receptor coactivator-related disease is an SRC-1 related disease. Optionally, the steroid receptor coactivator-related disease is an SRC-2 related disease. Optionally, the steroid receptor coactivator-related disease is an SRC-3 related disease. In some embodiments, the steroid receptor coactivator-related disease is cancer.

The methods include administering to a subject an effective amount of one or more of the compounds or compositions described herein, or a pharmaceutically acceptable salt or prodrug thereof. Effective amount, when used to describe an amount of compound in a method, refers to the amount of a compound that achieves the desired pharmacological effect or other biological effect. The effective amount can be, for example, the concentrations of compounds at which SRC is stimulated in vitro, as provided herein. In some embodiments, the effective amount of the compounds at which SRC is stimulated in vitro can include a concentration of from about 1 µM to about 10 µM (e.g., from about 2 µM to about 8 µM or from about 3 µM to about 6 For example, the effective amount of MCB-613 at which SRC is stimulated in vitro can be from about 4 µM to about 6 µM (e.g., about 5 µM).

Also contemplated is a method that includes administering to the subject an amount of one or more compounds described herein such that an in vivo concentration at a target cell in the subject corresponding to the concentration administered in vitro is achieved.

The compounds and compositions described herein or pharmaceutically acceptable salts thereof are useful for treating cancer in humans, including, without limitation, pediatric and geriatric populations, and in animals, e.g., veterinary applications.

Optionally, the cancer is a cancer that has an increased expression of SRC-1, SRC-2, and/or SRC-3 as compared to non-cancerous cells of the same cell type. Optionally, the cancer is bladder cancer, brain cancer, breast cancer, colorectal cancer (e.g., colon cancer, rectal cancer), cervical cancer, chondrosarcoma, endometrial cancer, gastrointestinal cancer, gastric cancer, genitourinary cancer, head and neck cancer, hepatocellular carcinoma, liver cancer, lung cancer, ovarian cancer, pancreatic cancer, prostate cancer, renal cancer, skin cancer, or testicular cancer. Optionally, the breast cancer is triple negative breast cancer. As used herein, triple negative breast cancer (TNBC) refers to a subtype of breast cancer that lacks detectable protein expression of the estrogen receptor (ER) and progesterone receptor (PR) and the absence of HER2 protein over expression. In other words, TNBC refers to an immunophenotype of breast cancer that is immunologically negative to ER, PR, and HER2.

Optionally, the cancer is glioblastoma. In some examples, the glioblastoma is a glioblastoma multiforme tumor. Optionally, the glioblastoma multiforme tumor is a pediatric glioblastoma multiforme tumor. The methods of treating glioblastoma include administering to the subject a compound as described herein. Optionally, the methods of treating glioblastoma include methods of suppressing the growth of glioblastoma cells in the subject.

The methods of treating or preventing cancer in a subject can further comprise administering to the subject one or more additional agents. The one or more additional agents and the compounds described herein or pharmaceutically acceptable salts or prodrugs thereof can be administered in any order, including concomitant, simultaneous, or sequential administration. Sequential administration can be administration in a temporally spaced order of up to several days apart. The methods can also include more than a single administration of the one or more additional agents and/or the compounds described herein or pharmaceutically acceptable salts or prodrugs thereof. The administration of the one or more additional agents and the compounds described herein or pharmaceutically acceptable salts or prodrugs thereof can be by the same or different routes and concurrently or sequentially.

Additional therapeutic agents include, but are not limited to, chemotherapeutic agents. A chemotherapeutic agent is a compound or composition effective in inhibiting or arresting the growth of an abnormally growing cell. Thus, such an agent may be used therapeutically to treat cancer as well as other diseases marked by abnormal cell growth. Illustrative examples of chemotherapeutic compounds include, but are not limited to, bexarotene, gefitinib, erlotinib, gemcitabine, paclitaxel, docetaxel, topotecan, irinotecan, temozolomide, carmustine, vinorelbine, capecitabine, leucovorin, oxaliplatin, bevacizumab, cetuximab, panitumumab, bortezomib, oblimersen, hexamethylmelamine, ifosfamide, CPT-11, deflunomide, cycloheximide, dicarbazine, asparaginase, mitotant, vinblastine sulfate, carboplatin, colchicine, etoposide, melphalan, 6-mercaptopurine, teniposide, vinblastine, antibiotic derivatives (e.g. anthracyclines such as doxorubicin, liposomal doxorubicin, and diethylstilbestrol doxorubicin, bleomycin, daunorubicin, and dactinomycin); antiestrogens (e.g., tamoxifen); antimetabolites (e.g., fluorouracil (FU), 5-FU, methotrexate, floxuridine, interferon alpha-2B, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cisplatin, vincristine and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chlorambucil, mechlorethamine (nitrogen mustard) and thiotepa); and steroids (e.g., bethamethasone sodium phosphate).

Any of the aforementioned therapeutic agents can be used in any combination with the compositions described herein. Combinations are administered either concomitantly (e.g., as an admixture), separately but simultaneously (e.g., via separate intravenous lines into the same subject), or sequentially (e.g., one of the compounds or agents is given first followed by the second). Thus, the term combination is used to refer to concomitant, simultaneous, or sequential administration of two or more agents.

Optionally, a compound or therapeutic agent as described herein may be administered in combination with a radiation therapy, an immunotherapy, a gene therapy, or a surgery.

The methods and compounds as described herein are useful for both prophylactic and therapeutic treatment. For prophylactic use, a therapeutically effective amount of the compounds and compositions or pharmaceutically acceptable salts thereof as described herein are administered to a subject prior to onset (e.g., before obvious signs of cancer), during early onset (e.g., upon initial signs and symptoms of cancer), or after the development of cancer. Prophylactic administration can occur for several days to years prior to the manifestation of symptoms of cancer. Therapeutic treatment involves administering to a subject a therapeutically effective amount of the compounds and compositions or pharmaceutically acceptable salts thereof as described herein after cancer is diagnosed.

The compounds described herein are also useful in stimulating a steroid receptor coactivator protein in a cell. The methods of stimulating a steroid receptor coactivator protein in a cell includes contacting a cell with an effective amount of one or more of the compounds as described herein. Optionally, the steroid receptor coactivator protein is one or more of SRC-1, SRC-2, or SRC-3. Optionally, the contacting is performed in vivo. Optionally, the contacting is performed in vitro.

The methods herein for prophylactic and therapeutic treatment optionally comprise selecting a subject with or at risk of developing cancer. A skilled artisan can make such a determination using, for example, a variety of prognostic and diagnostic methods, including, for example, a personal or family history of the disease or condition, clinical tests (e.g., imaging, biopsy, genetic tests), and the like. Optionally, the methods herein can be used for preventing relapse of cancer in a subject in remission (e.g., a subject that previously had cancer).

V. Kits

Also provided herein are kits for treating or preventing cancer in a subject. A kit can include any of the compounds or compositions described herein. For example, a kit can include a compound of Formula I, Formula II, or combinations thereof. A kit can further include one or more additional agents, such as one or more chemotherapeutic agents. A kit can include an oral formulation of any of the compounds or compositions described herein. A kit can include an intravenous formulation of any of the compounds or compositions described herein. A kit can additionally include directions for use of the kit (e.g., instructions for treating a subject), a container, a means for administering the compounds or compositions (e.g., a syringe), and/or a carrier.

As used herein the terms treatment, treat, or treating refer to a method of reducing one or more symptoms of a disease or condition. Thus in the disclosed method, treatment can refer to a 10%, 20%, 30%, 40%, 50%, 60%, 70%, 80%, 90%, or 100% reduction in the severity of one or more symptoms of the disease or condition. For example, a method for treating a disease is considered to be a treatment if there is a 10% reduction in one or more symptoms or signs (e.g., size of the tumor or rate of tumor growth) of the disease in a subject as compared to a control. As used herein, control refers to the untreated condition (e.g., the tumor cells not treated with the compounds and compositions described herein). Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refer to an action, for example, administration of a composition or therapeutic agent, that occurs before or at about the same time a subject begins to show one or more symptoms of the disease or disorder, which inhibits or delays onset or severity of one or more symptoms of the disease or disorder.

As used herein, references to decreasing, reducing, or inhibiting include a change of 10%, 20%, 30%, 40%, 50%, 60%, 70%, 80%, 90% or greater as compared to a control level. Such terms can include, but do not necessarily include, complete elimination.

As used herein, subject means both mammals and non-mammals. Mammals include, for example, humans; non-human primates, e.g., apes and monkeys; cattle; horses; sheep; rats; mice; pigs; and goats. Non-mammals include, for example, fish and birds.

Throughout this application, various publications are referenced. The disclosures of these publications in their entireties are hereby incorporated by reference into this application.

The examples below are intended to further illustrate certain aspects of the methods and compositions described herein, and are not intended to limit the scope of the claims.

EXAMPLES

Example 1: Synthesis of Compounds

All reagents were purchased from Alfa Aesar (Ward Hill, Mass.) or Aldrich (Milwaukee, Wis.). Compounds were characterized by ¹H NMR on a Varian 400-MR spectrometer (Palo Alto, Calif.). The purities were monitored by a Shimadzu Prominence HPLC with a Zorbax C18 or C8 column (4.6×250 mm) or ¹H (at 400 MHz) absolute spin-count quantitative NMR analysis with imidazole as an internal standard. The purities of the compounds were found to be >95%.

General method A. Sodium hydroxide solution (400 mg, 10 mmol, 2.5 equiv.) in water/ethanol (V/V=1/1, 8 mL) was added dropwise to a solution of 3,4,5-trimethoxybenzaldehyde (4 mmol, 1 equiv.) and dihydro-2H-pyran-4(3H)-one (2 mmol, 0.5 equiv). The mixture was stirred for 12 hours at room temperature. The precipitate was filtered and washed with water and ethanol to give a white or pale yellow powder, in 70-90% yield.

General method B. A solution of hydrogen chloride in acetic acid (20 mL) was added into cyclohexanone (2 mmol, 0.5 equiv) and 3-pyridinecarboxaldehyde (4 mmol, 1 equiv.) at room temperate. The mixture was stirred at room temperature for 12 hours. The solution was neutralized with aqueous NaHCO₃ (5% w/v). The precipitate was filtered and washed with water and ethanol to give a white or pale yellow powder, in 70-90% yield.

General method C. A mixture of a cyclohexanone (0.5 mmol), benzylamine (0.5 mmol) and anhydrous MgSO₄ (5.0 mmol) in anhydrous CH₂Cl₂ (5 mL) was stirred for 24 hours. 3-Pyridinecarboxaldehyde (0.5 mmol) was added dropwise and the solution was stirred for 12 hours. MgSO₄ was filtered off and the filtrate was concentrated. The concentrated filtrate was purified using column chromatography (silica gel, CH₂Cl₂:MeOH=10:1) to give the mono-adduct as a yellow oil. (58 mg, 62% yield).

Compound SYC-907 was prepared from cyclohexanone and 3-pyridinecarboxaldehyde, following general methods B, as a yellow solid. ¹H NMR (400 MHz, CDCl₃): δ 8.71 (bs, 2H), 8.56 (d, J=4.8 Hz, 2H), 7.76-7.74 (m, 4H), 7.35-7.32 (m, 2H), 2.94-2.91 (m, 4H), 1.84-1.81 (m, 2H).

Compound SYC-908 was prepared from 4-ethylcyclohexanone and 2-pyridinecarboxaldehyde, following general methods B, as a yellow solid. ¹H NMR (400 MHz, CDCl₃): δ 8.71-6.93 (m, 1H), 8.51-8.50 (m, 1H), 7.71-7.68 (m, 4H), 7.47-7.41 (m, 2H), 7.20-7.16 (m, 2H), 3.63-3.59 (m, 2H), 3.09-2.71 (m, 2H), 1.69-1.42 (m, 3H), 0.94-0.72 (m, 3H).

Compound SYC-909 was prepared from 4-methylcyclohexanone and 3-pyridinecarboxaldehyde, following general methods B, as a yellow solid. ¹H NMR (400 MHz, CDCl₃): δ 8.71 (bs, 2H), 8.57 (d, J=4.8 Hz, 2H), 7.75-7.74 (m, 4H), 7.36-7.33 (m, 2H), 3.05 (d, J=16 Hz, 2H), 2.57-2.50 (m, 2H), 1.92-1.91 (m, 1H), 1.09-1.07 (m, 3H).

Compound SYC-910 was prepared from dihydro-2H-pyran-4(3H)-one and 3,4,5-trimethoxybenzaldehyde, following general methods A, as a yellow solid. ¹H NMR (400 MHz, CDCl₃): δ 7.75 (s, 2H), 6.54 (s, 4H), 4.96 (m, 4H), 3.89-3.88 (m, 18H).

Compound SYC-911 was prepared from 1-methylpiperidin-4-one and 2,3-dimethoxybenzaldehyde, following general methods B, as a yellow solid. ¹H NMR (400 MHz, CDCl₃): δ 8.01 (bs, 2H), 7.09-7.05 (m, 2H), 6.94 (d, J=8.4 Hz, 2H), 6.83 (d, J=7.2 Hz, 2H), 3.98-3.80 (m, 12H), 3.63 (bs, 4H), 2.37 (s, 3H).

Compound SYC-912 was prepared from 1-methylpiperidin-4-one and 3,4,5-trimethoxybenzaldehyde, following general methods B, as a yellow solid. ¹H NMR (400 MHz, CDCl₃): δ 7.74 (bs, 2H), 6.62 (s, 4H), 3.89-3.88 (m, 18H), 3.79 (bs, 4H), 2.47 (s, 3H).

Compound SYC-913 was prepared from 1-methylpiperidin-4-one and 2-pyridinecarboxaldehyde, following general methods B, as a yellow solid. ¹H NMR (400 MHz, CDCl₃): δ 8.71 (bs, 2H), 7.72-7.68 (m, 2H), 7.61 (bs, 2H), 7.46 (d, J=8.0 Hz, 2H), 7.21-7.18 (m, 2H), 4.16 (bs, 4H), 2.53 (s, 3H).

Compound SYC-914 was prepared from 1-ethylpiperidin-4-one and 3,4,5-trimethoxybenzaldehyde, following general methods B, as a yellow solid. ¹H NMR (400 MHz, CDCl₃): δ 7.74 (bs, 2H), 6.62 (s, 4H), 3.89-3.86 (m, 22H), 2.62-2.61 (m, 2H), 1.07 (t, J=7.2 Hz, 3H).

Compound SYC-915 was prepared from 1-ethylpiperidin-4-one and 2-pyridinecarboxaldehyde, following general methods B, as a yellow solid. ¹H NMR (400 MHz, CDCl₃): δ 8.71 (bs, 2H), 7.72-7.68 (m, 2H), 7.62 (bs, 2H), 7.46 (d, J=8.0 Hz, 2H), 7.21-7.17 (m, 2H), 4.23 (bs, 4H), 2.71-2.66 (m, 2H), 1.14 (t, J=7.2 Hz, 3H).

Compound SYC-916 was prepared from 1-isopropylpiperidin-4-one and 2-pyridinecarboxaldehyde, following general methods B, as a yellow solid. ¹H NMR (400 MHz, CDCl₃): δ 8.71 (bs, 2H), 7.71-7.67 (m, 2H), 7.60 (bs, 2H), 7.43 (d, J=8.0 Hz, 2H), 7.20-7.17 (m, 2H), 4.28 (bs, 4H), 3.00-2.97 (m, 1H), 1.13-1.12 (m, 6H).

Compound SYC-917 was prepared from 1-isopropylpiperidin-4-one and 2-bromonicotinaldehyde, following general methods B, as a yellow solid. ¹H NMR (400 MHz, CDCl₃): δ 8.34 (bs, 2H), 7.99-7.92 (m, 2H), 7.35-7.29 (m, 4H), 3.64 (bs, 4H), 2.96-2.92 (m, 1H), 1.05-1.02 (m, 6H).

Compound SYC-918 was prepared from 1-isopropylpiperidin-4-one and 6-(trifluoromethyl)nicotinaldehyde, following general methods B, as a yellow solid. ¹H NMR (400 MHz, CDCl₃): δ 8.76 (bs, 2H), 7.87 (d, J=8.4 Hz, 2H), 7.77-7.75 (m, 4H), 3.84 (bs, 4H), 3.00-2.96 (m, 1H), 1.08-1.06 (m, 6H).

Compound SYC-919 was prepared from 4-isopropylcyclohexanone and 2-pyridinecarboxaldehyde, following general methods B, as a yellow solid. ¹H NMR (400 MHz, CDCl₃): δ 8.71 (bs, 2H), 7.72-7.68 (m, 2H), 7.47-7.43 (m, 2H), 7.20-7.16 (m, 2H), 7.20-7.17 (m, 2H), 3.62-3.58 (m, 2H), 2.84-2.77 (m, 2H), 1.70-1.63 (m, 2H), 0.95-0.81 (m, 6H).

Compound SYC-920 was prepared from 1-isopropylpiperidin-4-one and 2,3-dimethoxybenzaldehyde, following general methods B, as a yellow solid. ¹H NMR (400 MHz, CDCl₃): δ 7.99 (bs, 2H), 7.09-7.07 (m, 2H), 6.94-6.92 (m, 2H), 6.85-6.83 (m, 2H), 3.88-3.76 (m, 16H), 2.87-2.84 (m, 1H), 0.98-0.96 (m, 6H).

Compound SYC-921 was prepared from 1-isopropylpiperidin-4-one and 3,4,5-trimethoxybenzaldehyde, following general methods B, as a yellow solid. ¹H NMR (400 MHz, CDCl₃): δ 7.71 (bs, 2H), 6.63 (s, 4H), 3.94-3.82 (m, 22H), 2.92-2.88 (m, 1H), 1.08-1.06 (m, 6H).

Compound SYC-849 was prepared from dihydro-2H-pyran-4(3H)-one and 2-methoxybenzaldehyde, following general methods A, as a yellow solid. ¹H NMR (400 MHz, CDCl₃): δ 8.07 (bs, 2H), 7.36-7.32 (m, 2H), 7.06-7.04 (m, 2H), 6.97-6.91 (m, 4H), 4.79 (bs, 4H), 3.86 (s, 6H).

Compound SYC-850 was prepared from dihydro-2H-pyran-4(3H)-one and 3-methoxybenzaldehyde, following general methods A, as a yellow solid. ¹H NMR (400 MHz, CDCl₃): δ 7.79 (bs, 2H), 7.35-7.31 (m, 2H), 6.94-6.78 (m, 6H), 4.92 (bs, 4H), 3.83-3.81 (m, 6H).

Compound SYC-851 was prepared from dihydro-2H-pyran-4(3H)-one and 3-Pyridinecarboxaldehyde, following general methods B, as a yellow solid. ¹H NMR (400 MHz, CDCl₃): δ 8.61-8.59 (m, 4H), 7.79 (bs, 2H), 7.63-7.61 (m, 2H), 7.39-7.36 (m, 2H), 4.92 (bs, 4H).

Compound SYC-852 was prepared from 1-methylpiperidin-4-one and 2-methoxybenzaldehyde, following general methods B, as a yellow solid. $^1$H NMR (400 MHz, CDCl$_3$): δ 8.07 (bs, 2H), 7.35-7.31 (m, 2H), 7.19-7.17 (m, 2H), 6.98-6.90 (m, 4H), 3.87 (s, 6H), 3.70 (bs, 4H), 2.37 (s, 3H).

Compound SYC-853 was prepared from 1-methylpiperidin-4-one and 2,6-dimethoxybenzaldehyde, following general methods B, as a yellow solid. $^1$H NMR (400 MHz, CDCl$_3$): δ 7.79 (bs, 2H), 7.29-7.27 (m, 2H), 6.56 (d, J=8.4 Hz, 4H), 3.80 (s, 12H), 3.71 (bs, 4H), 2.25 (s, 3H).

Compound SYC-854 was prepared from 1-ethylpiperidin-4-one and 3-pyridinecarboxaldehyde, following general methods B, as a yellow solid. $^1$H NMR (400 MHz, CDCl$_3$): δ 8.67 (bs, 2H), 8.60-8.59 (m, 2H), 7.76 (bs, 2H), 7.71-7.69 (m, 2H), 7.38-7.35 (m, 2H), 3.81 (bs, 4H), 2.64-2.59 (m, 2H), 1.06 (t, J=7.2 Hz, 3H).

Compound SYC-855 was prepared from 1-isopropylpiperidin-4-one and 3-pyridinecarboxaldehyde, following general methods B, as a yellow solid. $^1$H NMR (400 MHz, CDCl$_3$): δ 8.67 (bs, 2H), 8.59-8.58 (m, 2H), 7.72-7.69 (m, 4H), 7.38-7.35 (m, 2H), 3.84 (bs, 4H), 2.97-2.92 (m, 1H), 1.06-1.04 (m, 6H).

Compound SYC-856 was prepared from 4-isopropylcyclohexanone and 3-methoxybenzaldehyde, following general methods A, as a yellow solid. $^1$H NMR (400 MHz, CDCl$_3$): δ 7.75 (bs, 2H), 7.34-7.30 (m, 2H), 7.05 (d, J=7.6 Hz, 2H), 6.98 (bs, 2H), 6.90-6.88 (m, 2H), 3.83 (bs, 6H), 3.08-3.03 (m, 2H), 2.60-2.53 (m, 2H), 1.65-1.51 (m, 2H), 0.90-0.89 (m, 6H).

Compound SYC-857 was prepared from 4-isopropylcyclohexanone and 3,4,5-trimethoxybenzaldehyde, following general methods A, as a yellow solid. $^1$H NMR (400 MHz, CDCl$_3$): δ 7.71 (bs, 2H), 6.71 (bs, 4H), 3.89 (bs, 18H), 3.15-3.10 (m, 2H), 2.59-2.52 (m, 2H), 1.68-1.53 (m, 2H), 0.94-0.93 (m, 6H).

Compound SYC-922 was prepared from cyclohexanone and 3-pyridinecarboxaldehyde, following general methods C, as a yellow solid. $^1$H NMR (400 MHz, CDCl$_3$): δ 8.62 (bs, 1H), 7.69-7.65 (m, 1H), 7.35-7.12 (m, 3H), 3.18-3.15 (m, 2H), 2.55-2.51 (m, 2H), 1.92-1.75 (m, 4H).

Compound SYC-923 was prepared from cyclohexanone and 3-pyridinecarboxaldehyde, following general methods C, as a yellow solid. $^1$H NMR (400 MHz, CDCl$_3$): δ 8.59-8.38 (m, 3H), 7.69-7.50 (m, 3H), 7.39-7.00 (m, 4H), 3.40-3.37 (m, 4H), 1.83-1.80 (m, 2H).

Example 2: MCB-613 Overstimulates Cancer Cells, Leading to Cell Stress and Death The data provided herein demonstrate that MCB-613 can super-stimulate SRCs' transcriptional activity. Further investigation revealed that MCB-613 increases SRCs' interaction with other coactivators and markedly induces ER stress coupled to the generation of reactive oxygen species (ROS) and the activation of the Abl kinase-SRC axis. Since cancer cells overexpress SRCs and rely on them for growth, MCB-613 induces excessive stress selectively in cancer cells.

4-Ethyl-2,6-bis-pyridin-3-ylmethylene-cyclohexanone (MCB-613) is a potent SRC small molecule stimulator, capable of hyper-activating all three SRC proteins, leading to the dramatic exacerbation of the proteostatic and oxidative stress that already exists in cancer cells, and causing selective cancer cell death. These unexpected results show that targeted over-stimulation of the very oncogenes that cancer cells depend upon for accelerated proliferation and survival can be used against them as a novel therapeutic approach.

Experimental Procedures

Chemicals.

MCB-613 (4-Ethyl-2,6-bis-pyridin-3-ylmethylene-cyclohexanone) was obtained from ChemBridge Corporation (San Diego, Calif.). N-Acetyl cysteine, cycloheximide, bufalin, chloroquine and curcumin were from Sigma (St. Louis, Mo.). MG132 and z-VAD-fmk were purchased from EMD Millipore (Billerica, Mass.). 15d-PGJ2 was from Cayman Chemical (Ann Arbor, Mich.). Kinase inhibitor library, AT9283, PHA7393598 and geldanamycin were purchased from SelleckChem (Houston, Tex.). CM-H2DCFDA was from Invitrogen (Carlsbad, Calif.). Phos-tag was purchased from Wako Chemicals (Richmond, Va.).

Fluorescence Spectrometry.

Fluorescence spectrometric measurements were performed on a SLM 48000S fluorescence spectrophotometer (SLM-Aminco, Rochester, N.Y.) and an Agilent Cary Eclipse Fluorescence spectrophotometer (Agilent Technologies, Inc., Santa Clara, Calif.) using the GST fusion proteins of different portions of SRC-3 expressed and purified. A total of 1.5 µM of GST SRC-3 RID, CID or bHLH was placed in a fluorescence cuvette and excited by UV light at a wavelength of 278 nm with a 2 nm bandwidth and the emission spectra were recorded from 290 nm to above 500 nm with a bandwidth of 4 nm. The aliquot size of test compound was maintained below 5% of the total sample volume in order to minimize the effects of dilution.

Human Stress and Toxicity PathwayFinder qPCR Array.

SRC-3 WT and KO HeLa cells were treated with MCB-613 or DMSO for 24 hours. Total RNA was extracted and subjected to reverse transcription using RT$^2$ First Strand Kit (SA Biosciences) followed by the analyses using the Human Stress and Toxicity PathwayFinder qPCR Array (SA Biosciences) according to the manufacturer's instruction.

MCF-7 Xenograft Tumor Model.

Twenty 6-8 week-old athymic nude female mice were obtained from Harlan. Two days before cancer cell injection, one estradiol pellet was embedded under the skin for each mouse and a new pellet was added twice at a one month interval. Following this, 1×10$^6$ MCF-7 cells (504) mixed with equal volume of growth factor reduced matrigel (BD Biosciences) were injected into the fat pad of each of the 2$^{nd}$ pair mammary gland without clearing. The MCB-613 treatment which lasted for seven weeks was started approximately seven weeks after the cell injection when tumor sizes reached above 5 mm in diameter. Ten mice received MCB-613 (20 mg/kg) in saline by i.p. injection, whereas the control group contained 10 mice which received saline only. The compound was injected three times a week. The mice were weighed once a week and tumors were measured twice a week during the treatment period.

Statistics.

Statistical significance was determined by 2-tailed Student's t test. A P value of less than 0.05 was considered statistically significant.

Antibodies.

Antibodies against SRC-1, SRC-3, Calnexin, Abl, phospho-CrKL (Y207), phospho-eIF2alpha (S51), cleaved caspase-3, ubiquitin and spliced Xbp1 were purchased from Cell Signaling (Danvers, Mass.). Antibodies against CARM1 and SRC-2 were obtained from Bethyl Laboratories (Montgomery, Tex.). FLAG antibody was obtained from Sigma. Antibody against phosphor-IRE1alpha (S724) was purchased from Abcam (Cambridge, Mass.). Antibodies against ATF4, GAPDH and CBP were purchased from Santa Cruz Biotechnology (Santa Cruz, Calif.).

Cell Culture.

Cell lines were maintained in DMEM (HeLa, MCF-7, HepG2), RPMI 1640 (H1299), or DMEM/F12 (PC-3) supplemented with 10% fetal calf serum, penicillin and streptomycin (100 U/ml). Primary mouse hepatocytes were isolated and cultured. Mouse embryonic fibroblasts (MEF) were cultured in DMEM. All cells were maintained at 37° C. under 5% $CO_2$.

Plasmids and Transfection.

The constructs expressing the Gal4 responsive luciferase reporter (pG5-luc), Gal4 DBD fusion with SRC-1, SRC-3 and SRC-3 (pBIND-SRC-1/-2/-3), MMP2 or MMP13 promoter driven luciferase reporter (MMP2-luc, MMP13-luc) were prepared. Twenty-four hours before transfection, HeLa cells were plated in 24-well dishes. The indicated expression plasmids were transfected into cells using Lipofectamine 2000 according to the manufacturer's instructions.

Luciferase Assays.

After various compound treatments, cells were lysed in luciferase lysis buffer and assayed for luciferase activity using the ONE-Glo luciferase assay system (Promega, Madison, Wis.). All luciferase activities were normalized to protein concentration determined by Bradford assay (Bio-Rad, Hercules, Calif.).

Western Blot and Immunoprecipitation.

For Western blotting, cells were harvested and lysed in lysis buffer (50 mM Tris, pH 8.0, 150 mM NaCl, 10% glycerol, 0.5% NP40, protease and phosphatase inhibitor) and then centrifuged for 15 min at 14000 rpm at 4° C. After total cellular protein concentration was determined by Bradford analysis (Bio-Rad, Hercules, Calif.), protein lysates were loaded onto and resolved by sodium dodecyl sulfate-polyacrylamide gel electrophoresis (SDS-PAGE) and transferred to PVDF membranes (BioRad) which were blocked and incubated with indicated antibodies. For immunoprecipitation, 10 μg of plasmid encoding FLAG-SRC-3 was transfected into HeLa cells with 90% confluence in one 10 cm plate with lipofectamine 2000 (Invitrogen). Twenty-four hours after transfection, the cells were treated with MCB-613 for one hour and lysed with lysis buffer (25 mM Tris-Cl pH7.5, 150 mM NaCl, 5% glycerol, 1 mM EDTA, 1% Triton X-100, protease and phosphatase inhibitor) at 4° C. After a 30-second sonication, the lysate was cleared by centrifugation at 14000 rpm at 4° C. for 15 minutes and was incubated with anti-Flag-M2 agarose affinity gel (Sigma) for four hours. The agarose gel was washed four times with washing buffer (25 mM Tris pH 8.0, 150 mM NaCl, 1 mM EDTA, 1% Triton X-100) and resuspended with SDS loading buffer for Western blotting.

Cell Viability Assays.

Cells were seeded in 96-well plates and allowed to reach 70% to 80% confluence. After indicated compound treatments, relative numbers of viable cells were measured by MTS assay using the Cell Titer 96 Aqueous One Solution Cell Proliferation Assay (Promega).

Measurement of Reactive Oxygen Species (ROS).

Cells were loaded with 10 μM general ROS indicator CM-H2DCFDA in serum free DMEM for 30 minutes at 37° C. in the dark. After a 5-minute recovery in complete DMEM, cells were treated with indicated concentrations of MCB-613 for 30 minutes, then fixed and examined by fluorescence microscopy.

Quantitative PCR Analysis.

HeLa cell total RNA was extracted using the RNeasy mini Kit (Qiagen, Valencia, Calif.), which was then reverse transcribed into cDNA with the SuperScript VILO cDNA synthesis kit (Invitrogen). Quantitative PCR was performed using a Taqman-based assay using the ABI StepOnePlus real-time PCR system (Biosystems, Foster City, Calif.). Relative quantitation was obtained by normalizing to the internal control GAPDH.

TABLE 1

Primers and corresponding Roche universal probes used in qPCR

| Gene | Primer sequence | Probe |
| --- | --- | --- |
| MMP13 | 5'-ccagtctccgaggagaaaca-3' (SEQ ID NO: 1) and<br>5'-aaaaacagctccgcatcaac-3' (SEQ ID NO: 2) | #73 |
| ATF6B | 5'-caccacagtccttctgcagtc-3' (SEQ ID NO: 3) and<br>5'-tcaggctggactcgaatagc-3' (SEQ ID NO: 4) | #83 |
| DDIT3 | 5'-aaggcactgagcgtatcatgt-3' (SEQ ID NO: 5) and<br>5'-tgaagatacacttccttcttgaaca-3' (SEQ ID NO: 6) | #21 |
| DNAJC3 | 5'-gagctcatcagagatggcaga-3' (SEQ ID NO: 7) and<br>5'-tgaacgaactgtatattcagcaatg-3' (SEQ ID NO: 8) | #21 |
| TNFRSF10B | 5'-agacccttgtgctcgttgtc-3' (SEQ ID NO: 9) and<br>5'-ttgttgggtgatcagagcag-3' (SEQ ID NO: 10) | #18 |
| LDHA | 5'-gtccttggggaacatggag-3' (SEQ ID NO: 11) and<br>5'-ttcagagagacaccagcaaca-3' (SEQ ID NO: 12) | #47 |
| GSR | 5'-aacaacatcccaactgtggtc-3' (SEQ ID NO: 13) and<br>5'-tccatatttatgaatggcttcatct-3' (SEQ ID NO: 14) | #83 |
| GAPDH | 5'-agccacatcgctcagacac-3' (SEQ ID NO: 15) and<br>5'-gcccaatacgaccaaatcc-3' (SEQ ID NO: 16) | #60 |

Results

MCB-613 is a Pan-SRC Stimulator

Figure 7:
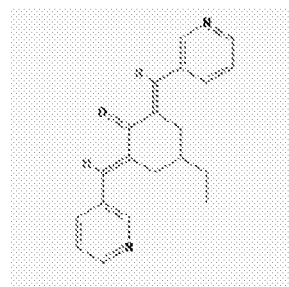
FIG. 7 shows that MCB-613 selectively activates SRCs. Panel A shows the structure of MCB-613. Panel B shows that MCB-613 activates SRC-3 rapidly. HeLa cells were transfected with pG5-LUC and pBIND or pBIND-SRC-3, followed by MCB-613 treatment for 4 hours. Data are represented as mean±SEM. The bars for each of pBIND and SRC-3 show the results for treatment with DMSO, 6 μM MCB-613, 8 μM MCB-613, and 10 μM MCB-613, from left to right. Panel C shows that MCB-613 only minimally activates transcriptional activator VP16. HeLa cells were transfected with Gal4-VP16 and pG5-LUC, followed by MCB-613 treatment for 24 hours. The bars show the results for treatment with DMSO, 6 μM MCB-613, 8 μM MCB-613, and 10 μM MCB-613, from left to right. Data are represented as mean±SEM. *P<0.05, P<0.01, *P<0.001.
Figure 7:
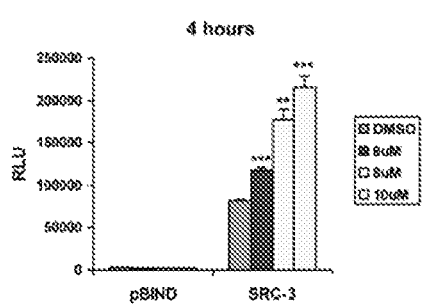
Figure 7:
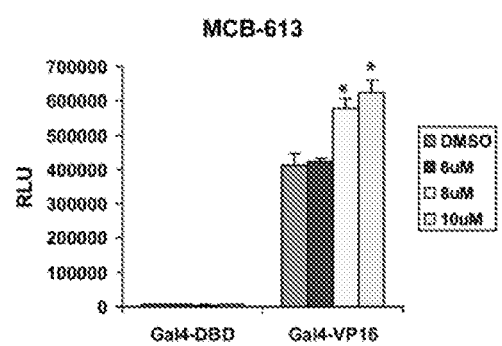

In a series of high throughput screens originally designed to identify SRC small molecule inhibitors, HEK293 cells transfected with a Gal4 responsive luciferase reporter (pG5-luc) and a construct encoding SRC-1, SRC-2 or SRC-3 fused with the DNA binding domain of Gal4 (pBIND-SRC-1, pBIND-SRC-2 or pBIND-SRC-3) were exposed to treatments with 359,484 compounds from a MLPCN chemical library (PubChem AID:588362, AID:652008 and AID:

588354). In addition to inhibitors that were initially sought in these screens, a number of compounds were found to stimulate the activity of SRC-1 and SRC-3. Primary screens indicated that there were 106 and 28 potential SRC-1 and SRC-3 stimulators, respectively, using a 2-fold activation cutoff compared with vehicle controls. Upon further testing and verification of a subset of these top compounds, MCB-613 (FIG. 7A), which exerted the greatest activation of SRC-1 in the primary screen, was later confirmed to be a strong activator of all three SRCs. As shown in FIG. 1A, 24-hour treatment with MCB-613 caused an extremely large and unprecedented (maximum 160-fold) induction in the activity of pBIND-SRC-1/-2/-3 in a dose-dependent manner. This stimulation by MCB-613 was selective for SRCs, failing to stimulate a GAL4-PGC-1α coactivator fusion protein (FIG. 1B) while minimally increasing the activity of a GAL4-VP16 fusion protein only at higher compound concentrations (FIG. 7C). The activation of SRCs by MCB-613 is so strong and rapid that a significant increase in SRC activity was already observed after 4 hours of treatment (FIG. 7B); and it represents the strongest stimulation observed to date under any conditions.

Since SRC-3 is preferentially utilized by AP-1 and PEA3 as a coactivator to drive expression of MMP2 and MMP13, cells were transfected with a MMP2 or MMP13 promoter driven luciferase reporter (MMP2-luc or MMP13-luc) and treated with MCB-613. It was found that SRC-3's coactivation of the MMP2 and MMP13 promoters was greatly enhanced by MCB-613 (FIG. 1C). Performing the same experiment in a SRC-3 KO HeLa cell line, in which both alleles of SRC-3 are knocked out using a zinc finger nuclease, activation of MMP2-luc by MCB-613 was diminished (FIG. 1D), confirming that the MCB-613 effect is at least in part SRC-3-dependent (SRC-1 and SRC-2 remain intact in these cells). Consistent with these findings, endogenous MMP13 expression can be also activated with MCB-613 treatment (FIG. 1E).

In order to characterize the underlying mechanism of MCB-613's activation of SRCs, a goal was identified to determine whether MCB-613 increases SRC activity by elevating the concentrations of SRC proteins in the cell. Instead, it was found that treatment of cells with MCB-613 for 24 hours resulted in decreases in SRC-1, SRC-2 and SRC-3 protein levels (FIG. 1F), indicating that MCB-613 inherently promotes the intrinsic activity of SRCs.

Next, it was assessed whether MCB-613 physically interacts with SRCs. Fluorescence spectroscopy was used to measure the intrinsic fluorescence of different SRC-3 protein domains, expressed as GST fusions in the presence of MCB-613, based on the theory that the direct SRC-3 binding with MCB-613 should quench its intrinsic fluorescence emission. As shown in FIG. 1G, the intrinsic fluorescence of the receptor interacting domain (RID) of SRC-3 was progressively quenched by increasing concentrations of MCB-613 with a half-affecting concentration of 10 μM, and the emission maximum also was shifted from 340 nm to 360 nm, indicating that MCB-613 directly binds to SRC-3 RID. MCB-613 also affected the fluorescence of the basic helix-loop-helix (bHLH) domain with more potency at a concentration of 2 μM, while a higher concentration of at least 20 μM was required to detect fluorescence quenching of the CBP interacting domain (CID). These results show that MCB-613 preferentially binds to the bHLH followed by the RID of SRC-3 and that this binding is selective.

Activated SRC-3 has been shown to recruit other transcriptional coactivators including CBP and CARM1 to form a multi-coactivator complex. To test whether MCB-613 affects the ability of SRC-3 to interact with these coactivator complex members, HeLa cells overexpressing FLAG-SRC-3 were treated with MCB-613 for one hour and subjected to coimmunoprecipitation to assess SRC-3-CBP-CARM1 complex formation. As shown in FIG. 1H, MCB-613 increased SRC-3's interaction with CBP and CARM1 robustly in a dose-dependent manner. Taken together, these results indicate that MCB-613 binds to SRC-3, where it then promotes coactivator complex formation, consistent with induced coactivator transcriptional activity.

MCB-613 Selectively Kills Cancer Cells

Figure 2:
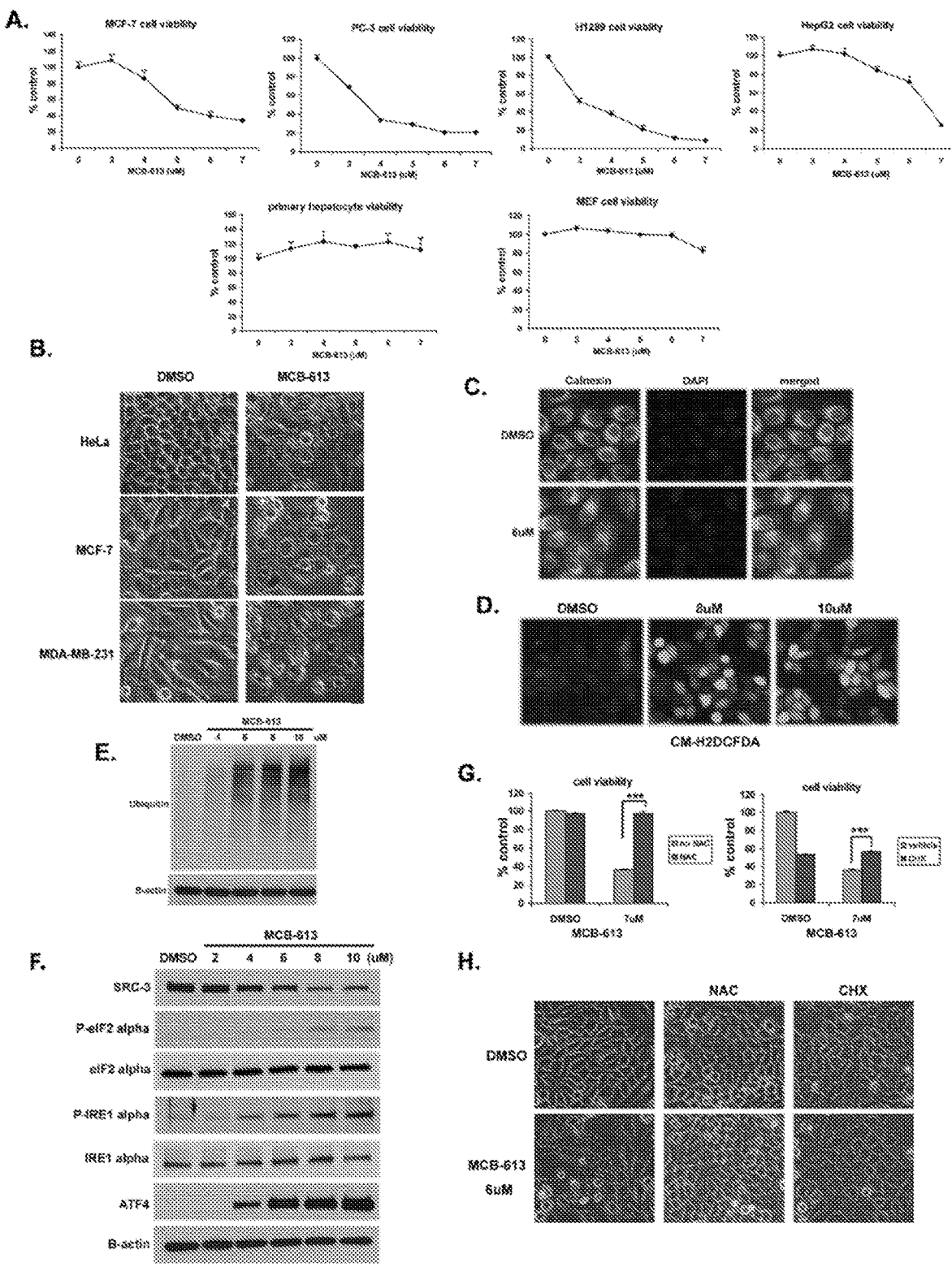
FIG. 2 shows that MCB-613 induces paraptotic-like cell death. Panel A shows MCB-613 selectively kills cancer cells. Viability of MCF-7, PC-3, H1299, HepG2, mouse primary hepatocytes or mouse embryonic fibroblasts treated with MCB-613 for 48 hours was determined by MTS assay. Panel B shows MCB-613 treatment causes extensive cytoplasmic vacuolization in HeLa, MCF-7 or MDA-MB-231 cells. Panel C shows Vacuoles induced by MCB-613 are derived from the endoplasmic reticulum (ER). HeLa cells treated with MCB-613 for 24 hours were immunostained for calnexin. Panel D shows MCB-613 treatment causes a rapid increase in intracellular ROS levels as shown by a general ROS indicator CM-H2DCFDA. Panel E shows MCB-613 treatment leads to proteasome dysfunction. HeLa cells treated with MCB-613 for 5 hours were immunoblotted for ubiquitin. Panel F shows MCB-613 treatment induces UPR markers. HeLa cells were treated with MCB-613 for 4 hours and immunoblotted for the indicated UPR markers. Panel G shows cell death caused by MCB-613 can be rescued by an antioxidant or a protein synthesis inhibitor. HeLa cells were treated with MCB-613 for 24 hours in the presence or absence of N-Acetyl cysteine (NAC) or cycloheximide (CHX). Panel H shows cytoplasmic vacuolization caused by MCB-613 was blocked by antioxidant or protein synthesis inhibitor treatment. Data are represented as mean SD. ***P<0.001.

MCB-613 is cytotoxic. It can efficiently kill a variety of cancer cell lines (FIG. 2A), including MCF-7 (breast), PC-3 (prostate), H1299 (lung) and HepG2 (liver) cells. Although highly toxic to cancer cells, MCB-613 can spare normal cells at these concentrations, as mouse primary hepatocytes and MEF cells are resistant to this compound (FIG. 2A). MCB-613 treatment induced extensive vacuolization in cancer cells (FIG. 2B). To better understand how MCB-613 causes cell death, it was examined if apoptosis or autophagy was activated, especially considering that autophagy is the major cell death mechanism linked to vacuolization. MCB-613 treatment led to the induction of LC3BII and caspase-3 cleavage, markers for autophagy and apoptosis, respectively (FIG. 8A).

Figure 8:
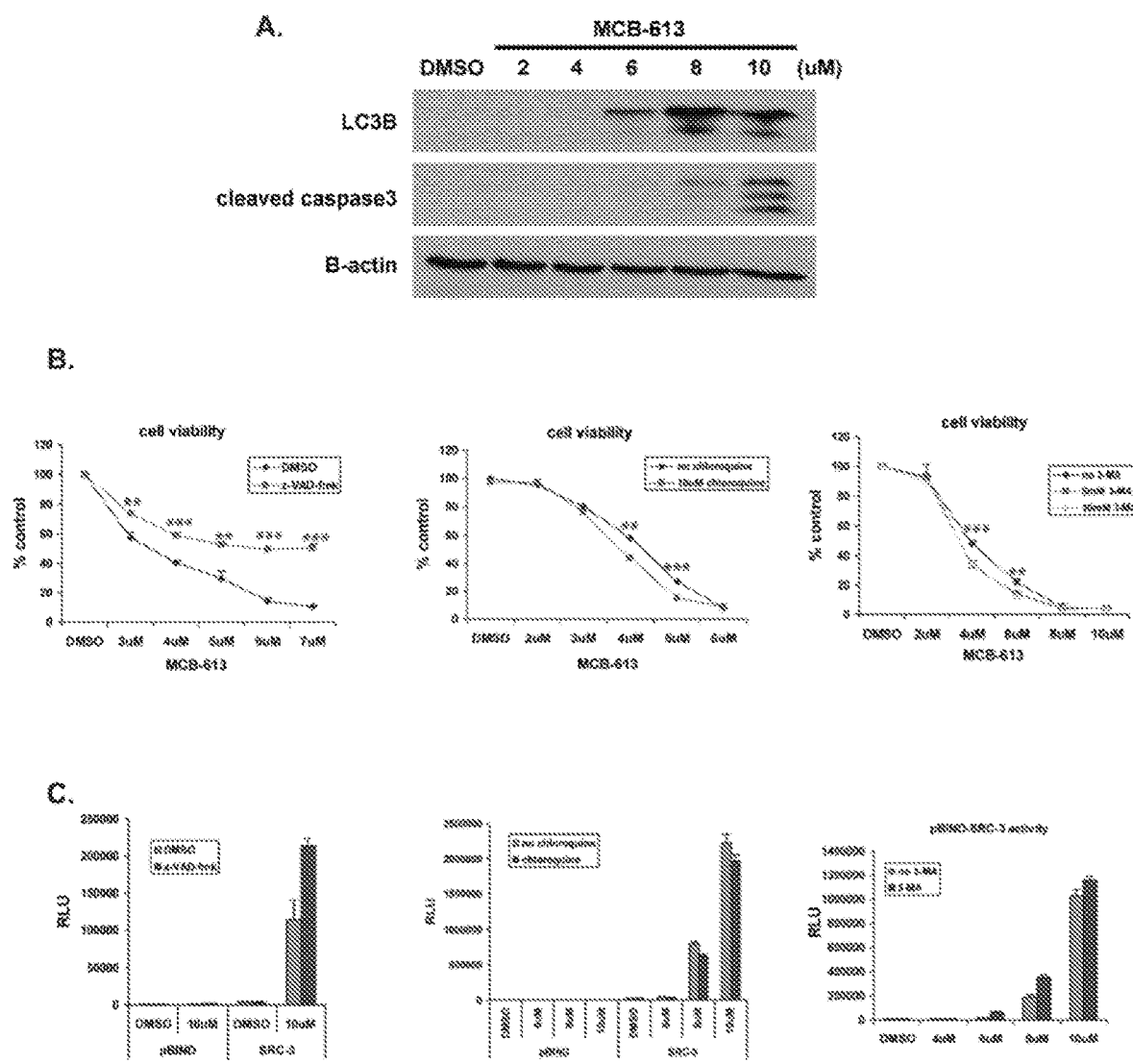
FIG. 8 shows that autophagy and apoptosis induced by MCB-613 is not involved in SRC activation. Panel A shows that MCB-613 also activates apoptosis and autophagy markers. HeLa cells were treated with MCB-613 for 24 hours, followed by western blots for LC3B and cleaved caspase-3. Panel B shows that apoptosis, but not autophagy, contributes to cell death induced by MCB-613. HeLa cells were treated with MCB-613 for 24 hours, in the presence or absence of caspase inhibitor z-VAD-fmk (left panel), autophagy inhibitor chloroquine (middle panel) or 3-MA (right panel). Cell viability was determined by MTS assay. Data are represented as mean±SD. P<0.01, *P<0.001. Panel C shows that activation of SRC-3 by MCB-613 does not involve apoptosis or autophagy. HeLa cells transfected with pBIND or pBIND-SRC-3 were treated with different concentrations of MCB-613 for 24 hours in the presence or absence of z-VAD-fmk, chloroquine or 3-MA. Data are represented as mean±SEM.

However, autophagy inhibitors, such as chloroquine and 3-methyladenine (3-MA), or caspase inhibitor z-VAD-fmk, could not rescue, or only partially rescued, cell death caused by MCB-613 (FIG. 8B). Thus, apoptosis, but not autophagy, partially contributes to cell death. Another mechanism also has to be involved to account for the full effect of MCB-613 on cell viability. In addition, neither apoptosis nor autophagy was directly linked to the activation of SRCs, as z-VAD-fmk, chloroquine or 3-MA did not inhibit the activation of SRCs by MCB-613 (FIG. 8C).

A non-apoptotic form of cell death, paraptosis, is characterized by extensive cytoplasmic vacuolization caused by the dilation of the endoplasmic reticulum (ER) and mitochondria and it does not rely upon hallmarks of apoptosis such as DNA fragmentation and caspase activation. Paraptotic-like cell death has been observed in developmental processes such as embryo development and neuronal degeneration, in several artificial or natural cellular models, and in response to treatment with some anti-cancer agents. Although the molecular details underlying paraptosis are still relatively understudied, there is evidence that the cytoplasmic vacuolization associated with it results from perturbations in ER and proteasome function. In addition to proteasome dysfunction and ER stress, paraptosis requires de novo protein synthesis and is linked to cellular redox homeostasis.

Consistent with the involvement of paraptosis in MCB-613 treated cells, vacuoles in cells treated with MCB-613 stained positive for calnexin (FIG. 2C), an ER-specific marker, indicating that they are derived from ER. Next, by using CM-H2DCFDA, a general ROS indicator, it was found that MCB-613 can induce a rapid and marked increase in intracellular ROS levels (FIG. 2D). MCB-613 also leads to proteasome dysfunction and ER stress, confirmed by the accumulation of polyubiquitinated proteins (FIG. 2E) and the activation of markers for the unfolded protein response (UPR) (FIG. 2F), including the phosphorylation of eIF2α and IRE1α as well as the induction of ATF4 protein expression. Since MCB-613 increases ROS levels and paraptosis requires protein synthesis, it was next examined whether an antioxidant or a protein synthesis inhibitor can block cell death caused by MCB-613. As shown in FIG. 2G, the antioxidant N-Acetyl cysteine (NAC) and the protein synthesis inhibitor cycloheximide (CHX) protected cells from MCB-613 mediated cytotoxicity. Importantly, vacuolization induced by MCB-613 also was blocked by co-treatment with NAC or CHX (FIG. 2H), indicating paraptotic cell death as the primary process underlying the cytotoxic properties of MCB-613.

SRC Hyper-Activation is Critical for Paraptosis Induced by MCB-613.

Figure 3:
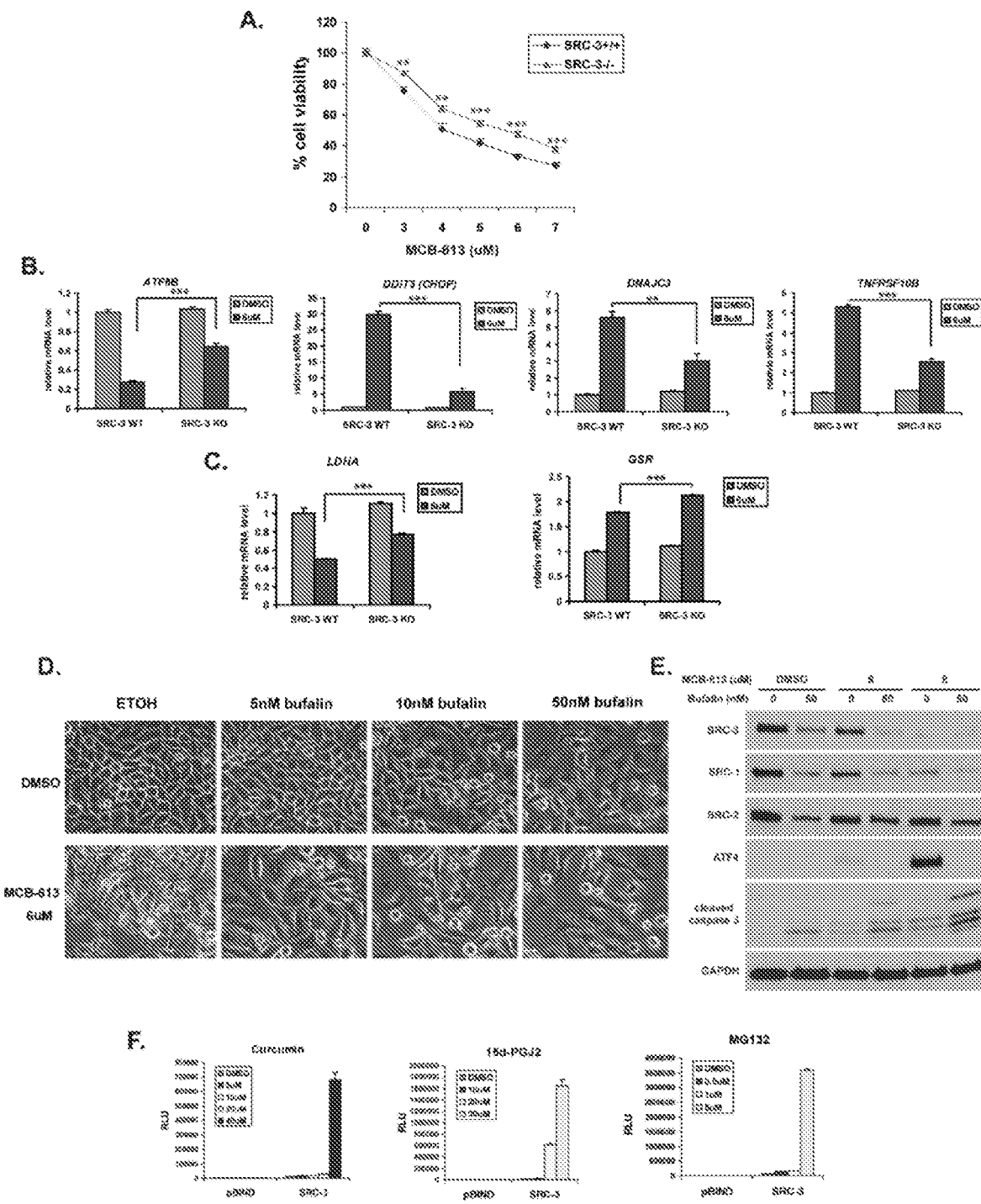
FIG. 3 shows SRC hyper-activation is involved in paraptosis induced by MCB-613. Panel A shows that SRC-3 KO HeLa cells are more resistant to MCB-613-induced cell death compared to WT cells. SRC-3 WT or KO HeLa cells were treated with MCB-613 for 24 hours. Panel B shows that UPR induced by MCB-613 is blunted in SRC-3 KO HeLa cells. SRC-3 WT and KO HeLa cells were treated with MCB-613 for 24 hours, and the indicated UPR targets' mRNAs were determined by qRT-PCR. Panel C shows that SRC-3 KO HeLa cells are more resistant to oxidative stress induced by MCB-613. qRT-PCR analysis of LDHA and GSR from SRC-3 WT and KO HeLa cells treated as in B is shown. Panel D shows that cytoplasmic vacuolization induced by MCB-613 is inhibited with bufalin. HeLa cells were treated with MCB-613 for 24 hours in the presence or absence of bufalin. Panel E shows that bufalin inhibits UPR induced by MCB-613 and increases apoptosis. HeLa cells were treated as in D. Panel F shows that additional agents can activate SRC-3, leading to paraptosis. HeLa cells transfected with pBIND-SRC-3 and pG5-LUC were treated with curcumin, 15-Deoxy-Δ12,14-prostaglandin J2 (15d-PGJ2), or MG132 for 24 hours. For the curcumin plot, the bars show the results for treatment with DMSO, 5 μM curcumin, 10 μM curcumin, 20 μM curcumin, and 40 μM curcumin, from left to right. For the 15d-PGJ2 plot, the bars show the results for treatment with DMSO, 10 μM 15d-PGJ2, 20 μM 15d-PGJ2, and 30 μM 15d-PGJ2, from left to right. For the MG132 plot, the bars show the results for treatment with DMSO, 0.5 μM MG132, 1 μM MG132, and 5 μM MG132, from left to right. Data are represented as mean±SD (MTS assay) or mean±SEM (qRT-PCR and luciferase). P<0.01, *P<0.001.

Since MCB-613 super-activates SRCs and induces paraptotic-like cell death, it was determined whether a causal link between these two events exists. SRC-3 KO HeLa cell viability was found to be less affected by MCB-613 compared with WT cells (FIG. 3A), suggesting that the cell death induced by MCB-613 is at least partially dependent on SRC-3 (SRC-1 and SRC-2 are still present in SRC-3 KO cells). The expression of downstream stress-response genes that are induced by MCB-613 in a SRC-3 dependent manner were then examined using the human Stress and Toxicity PathwayFinder qPCR array on SRC-3 WT or KO HeLa cells treated with MCB-613. The array focuses on genes involved in oxidative stress, hypoxia, DNA damage and UPR. As shown in FIG. 3B, ATF6B, a negative regulator of UPR, and CHOP, DNAJC3 and TNFRSF10B, downstream effectors of UPR, were either significantly downregulated or upregulated upon MCB-613 treatment in WT cells. However, these changes were all blunted in SRC-3 KO cells, again indicating that SRC-3 stimulation partly underlies the stress response pathways activated by MCB-613 treatment.

It was also found that oxidative stress related genes are differentially regulated in MCB-613 treated SRC-3 WT and KO cells (FIG. 3C). Lactate dehydrogenase A (LDHA) is an enzyme that converts L-lactate and $NAD^+$ to pyruvate and NADH in the final step of anaerobic glycolysis, and whose inhibition increases oxidative stress and to interfere with tumor progression. Glutathione reductase (GSR) is a central enzyme responsible for cellular antioxidant defense. MCB-613 treatment resulted in decreased LDHA expression and an increase in GSR expression in WT HeLa cells, consistent with the notion that the cells are attempting to mount a response to the ROS generating effects of MCB-613. Meanwhile, in SRC-3 KO cells treated with MCB-613, there was an attenuated decrease in LDHA expression and a stronger increase in GSR expression compared with WT cells, implying that the KO cells are more resistant to MCB-613 and suffered less oxidative stress due to the absence of SRC-3.

To further demonstrate that SRC activation underlies MCB-613-induced paraptosis, HeLa cells were treated with both MCB-613 and the SRC SMI bufalin, which has been shown to inhibit all three SRCs. If SRCs are responsible for driving MCB-613 induced paraptosis, bufalin co-treatment should abrogate the effects of MCB-613. Vacuolization induced by MCB-613 was effectively inhibited by bufalin (FIG. 3D). In addition, the induction of ER stress, as indicated by the induction of ATF4, was completely reversed by co-treatment with bufalin. Instead, bufalin treatment induced caspase-3 cleavage (FIG. 3E). Along the same lines, small interfering RNA-mediated simultaneous knock down of all three SRCs significantly impaired both the induction of ATF4 and the splicing of Xbp1 (another marker of ER stress) caused by MCB-613 treatment (FIG. 9A), again indicating that MCB-613 hyper-activation of SRCs is responsible for the paraptotic cell death response induced by this compound.

Figure 9:
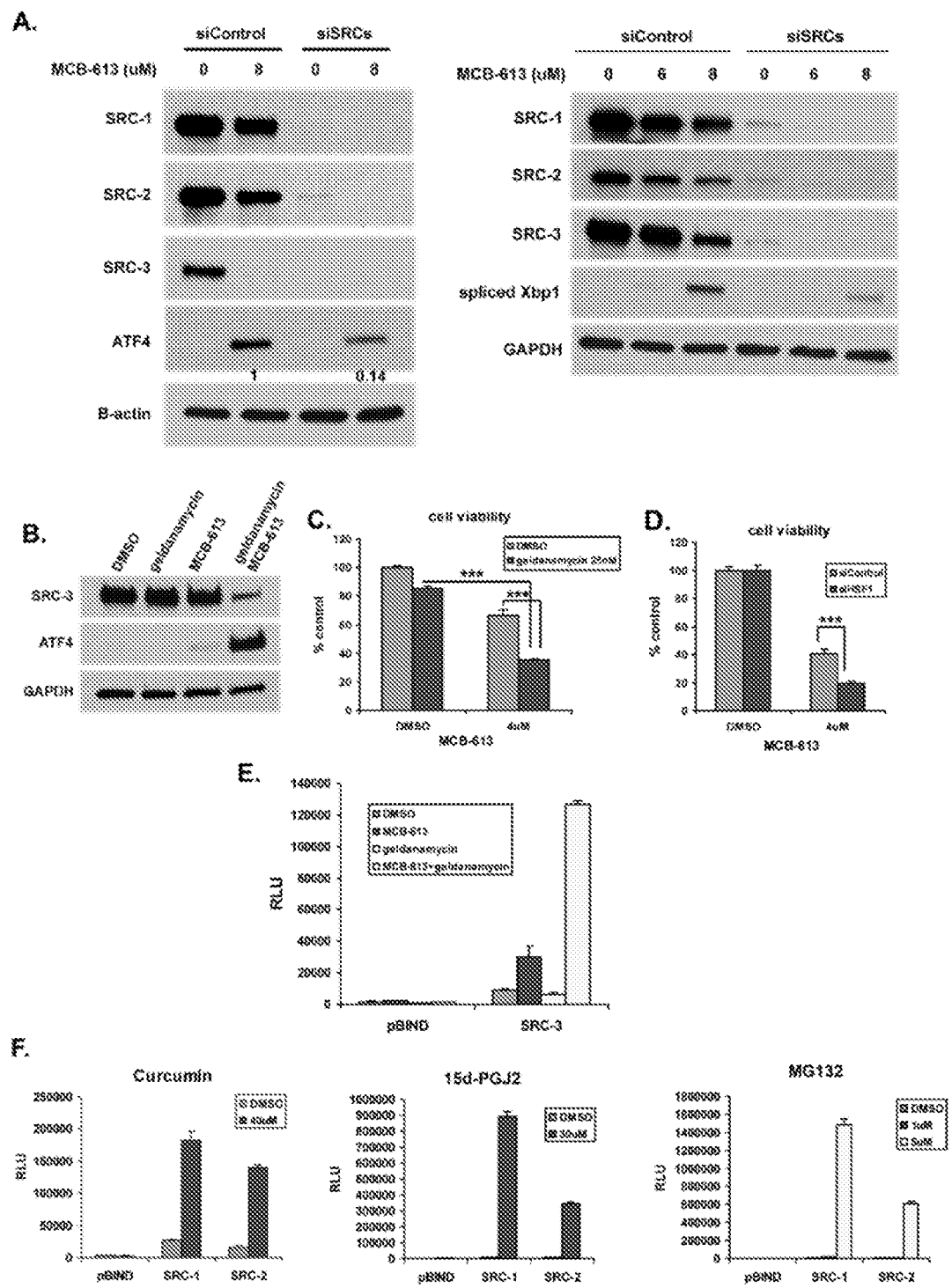
FIG. 9 shows that SRC hyper-activation is critical for paraptosis induced by MCB-613. Panel A shows that ATF4 induction and Xbp1 splicing caused by MCB-613 is diminished when all SRCs are knocked down. HeLa cells in which all three SRCs were simultaneously knocked down by siRNA were treated with MCB-613 for 15 hours (left) and 24 hours (right). Western blot shows protein levels of SRC-1, SRC-2, SRC-3, ATF4 and β-actin in left panel; SRC-1, SRC-2, SRC-3, spliced Xbp1, and GAPDH in right panel. Numbers indicate the relative abundance of respective proteins. Panel B shows that MCB-613 synergizes with geldanamycin to induce ER stress. HeLa cells were treated with 6 uM MCB-613, or 50 nM geldanamycin, or both for 24 hours. Western blot shows protein levels of SRC-3, ATF4 and GAPDH. Panel C shows that MCB-613 and geldanamycin synergize to induce cell death. HeLa cells were treated with MCB-613 in the presence or absence of geldanamycin at the indicated concentration for 48 hours. Data are represented as mean±SD. *P<0.001. Panel D shows that cell death induced by MCB-613 is exacerbated by knocking down HSF1. HeLa cells in which HSF1 was knocked down by siRNA were treated with MCB-613 for 48 hours. Data are represented as mean±SD. *P<0.001. Panel E shows that MCB-613 and geldanamycin synergize to activate SRC-3. HeLa cells transfected with pBIND-SRC-3 and pG5-LUC were treated with 6 uM MCB-613, 50 nM geldanamycin, or both for 24 hours. The bars for each of pBIND and SRC-3 show the results for treatment with DMSO, MCB-613, geldanamycin, and both MCB-613 and geldanamycin, from left to right. Data are represented as mean±SEM. Panel F demonstrates that other agents also activate SRC-1/-2 and lead to paraptosis. HeLa cells were transfected with pBIND-SRC-1 or pBIND-SRC-2 and pG5-LUC, followed by treatment with Curcumin, 15-Deoxy-Δ12,14-Prostaglandin J2 (15d-PGJ2), or MG132 for 24 hours. Data are represented as mean±SEM.

One response the cells engage to counteract ER stress is to induce molecular chaperones, such as heat shock proteins, in order to enhance the folding capacity of ER and alleviate the accumulation of misfolded/unfolded proteins. Indeed, many heat shock proteins were significantly induced by the treatment with MCB-613, showing that the cells are striving to battle the enormous stress imposed by the compound. MCB-613 and geldanamycin, an HSP90 inhibitor, synergized to greatly induce ER stress and cell death, even though suboptimal concentrations were used in the assays (FIGS. 9B and 9C). Consistently, knocking down HSF1 (heat shock factor 1), which encodes the major transcription factor for heat shock proteins, also exacerbated the cell death caused by MCB-613 (FIG. 9D). The synergism between MCB-613 and geldanamycin also applied to the activation of SRC-3 (FIG. 9E), further demonstrating that super activation of SRCs is integral to the effect of MCB-613 on ER stress and cell viability.

More support for the close relationship between SRCs and paraptosis is evidenced by observations that additional agents, including curcumin, 15-deoxy-$\Delta^{12,14}$-prostaglandin J2 (15d-PGJ2) and MG132, robustly enhance the intrinsic transcriptional activities of SRCs (FIG. 3F and FIG. 9F). All these agents have been shown to cause cytoplasmic vacuolization and paraptotic-like cell death, showing that SRC hyper-stimulation is closely coupled to cellular stress pathways connected to paraptosis.

Oxidative Stress Induced by MCB-613 Contributes to SRC Hyper-Activation

Figure 4:
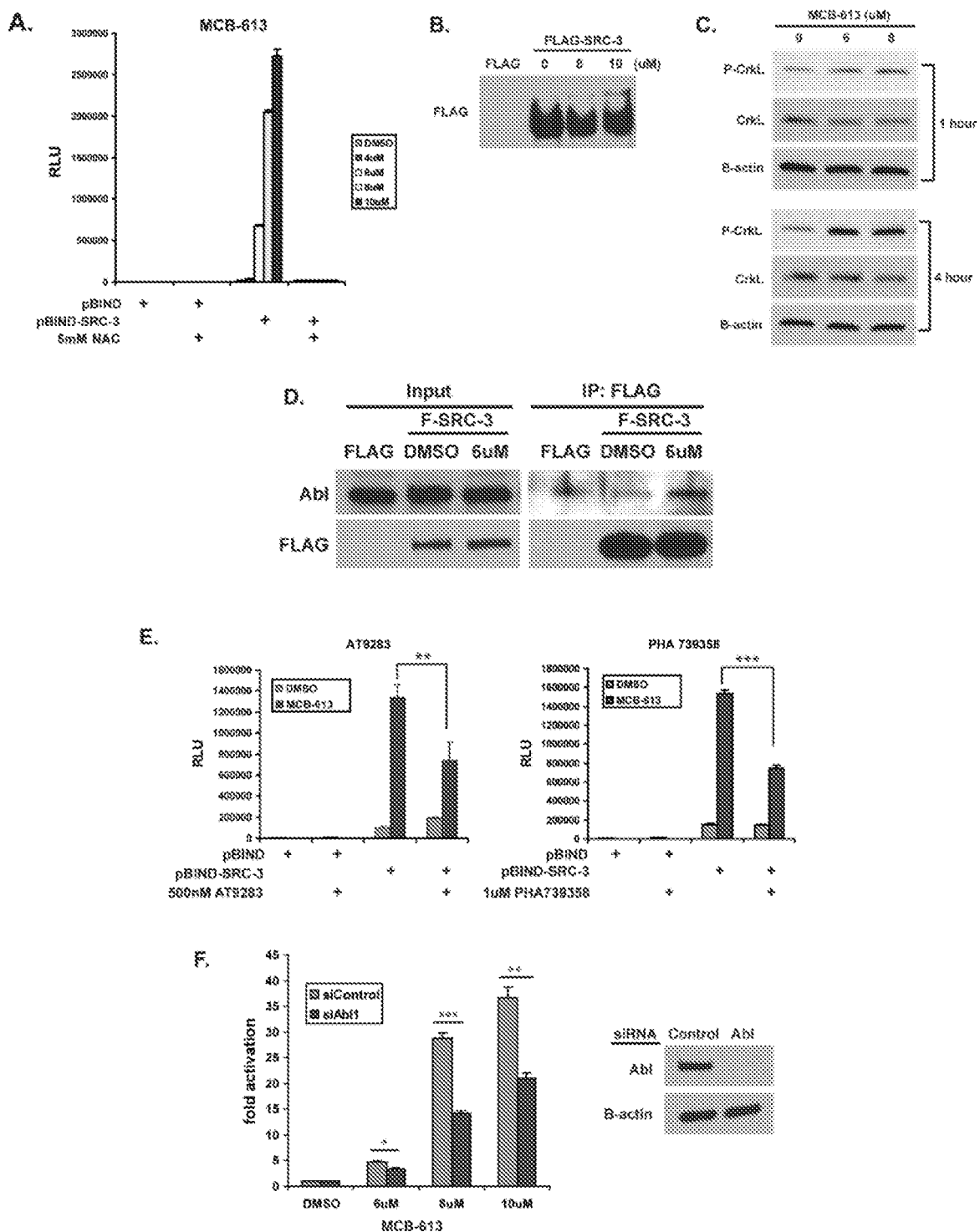
FIG. 4 shows oxidative stress induced by MCB-613 activates SRC-3 via the Abl kinase signaling pathway. Panel A shows that antioxidant treatment prevents SRC-3 activation by MCB-613. HeLa cells transfected with pG5-LUC and pBIND-SRC-3 were treated with MCB-613 for 24 hours in the presence or absence of NAC. The bars show the results for treatment with DMSO, 4 μM MCB-613, 6 μM MCB-613, 8 μM MCB-613, and 10 μM MCB-613, from left to right. Panel B shows that MCB-613 treatment leads to phosphorylation of SRC-3. The immunoprecipitate from FLAG-SRC-3 overexpressing HeLa cells treated with MCB-613 for 1 hour was resolved on a 5% SDS-PAGE gel containing 20 μM Phos-tag. Panel C shows that Abl kinase is activated by MCB-613. Phosphorylated CrkL is shown in HeLa cells treated with MCB-613 for 1 hour or 4 hours. Panel D shows that MCB-613 increases interaction between SRC-3 and Abl. HeLa cells overexpressing FLAG-SRC-3 were treated with MCB-613 for 1 hour followed by coIP with FLAG antibody. Panel E shows that activation of SRC-3 by MCB-613 is inhibited by Abl kinase inhibitors. HeLa cells were transfected as in A and treated with MCB-613 for 24 hours in the presence or absence of AT9283 or PHA 739358. Panel F shows that siRNA mediated knock down of Abl inhibits SRC-3 activation by MCB-613. HeLa cells transfected with control siRNA or siAbl1 were transfected with pBIND-SRC-3 and pG5-LUC, followed by treatment with MCB-613 for 24 hours. Knockdown efficiency of Abl is shown by immunoblot (right panel). Data are represented as mean±SEM. *P<0.05, P<0.01, *P<0.001.
Figure 10:
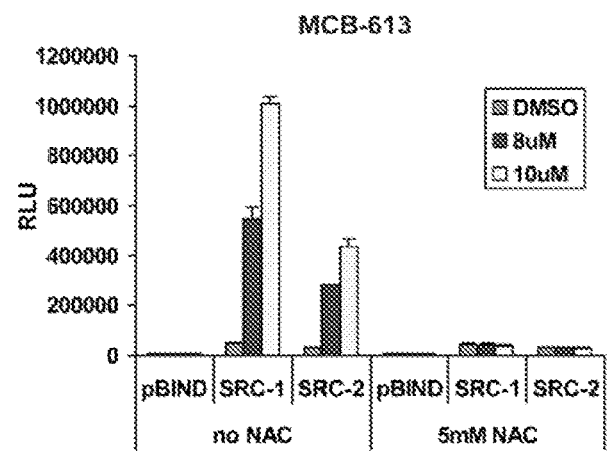
FIG. 10 shows that antioxidant treatment prevents SRC-1 and SRC-2 activation by MCB-613. HeLa cells were transfected as in FIG. 9 and treated with MCB-613 for 24 hours in the presence or absence of NAC. Data are represented as mean±SEM.

The relationship between oxidative stress and the activation of SRCs was next examined. To investigate this question, the effect of co-treatment with the antioxidant N-acetylcysteine (NAC) on MCB-613-induction of SRC intrinsic transcriptional activity was tested. It was found that NAC was able to abrogate the stimulatory effects of MCB-613 on SRC transcriptional activity (FIG. 4A and FIG. 10).

The impact of MCB-613 treatment on SRC-3 phosphorylation was also explored. Using a phos-tag SDS-PAGE system that allows phosphorylated proteins to be characterized by differences in their migration rate, it was found that MCB-613 treatment resulted in a SRC-3 species with reduced mobility in the gel (FIG. 4B) which disappeared after lambda phosphatase treatment, indicative of a phosphorylated form of SRC-3. To investigate which kinase(s) are responsible for MCB-613 induced phosphorylation, a kinase inhibitor library from Selleck Chemicals, which contained a collection of 141 kinase inhibitors, was screened. It was found that a number of Abl kinase inhibitors were able to inhibit the activation of pBIND-SRC-3 by MCB-613 (FIG. 4E).

Abl is a non-receptor tyrosine kinase present in both the cytoplasm and nucleus that has been implicated in a variety of cellular processes such as growth, differentiation and stress response. Not to be bound by theory, Abl is a promising candidate kinase for MCB-613 mediated SRC hyper-stimulation because 1) acute hyper-activation of the oncogenic Bcr-Abl fusion protein induces severe cytoplasmic vacuolization and ER stress; 2) Abl phosphorylates and activates SRC-3; and 3) Abl is activated in response to oxidative stress. It was first tested whether Abl is activated by MCB-613 treatment by assaying CrkL (Y207) phosphorylation as a marker for Abl activation. As shown in FIG. 4C, activation of Abl could be observed as early as one hour after MCB-613 treatment, and reached a high level after four hours of treatment. Subsequent co-immunoprecipitation analyses revealed that MCB-613 increased the interaction between SRC-3 and Abl (FIG. 4D). Two Abl kinase inhibitors, AT9283 and PHA 739358, as well as small interfering RNAs targeting Abl, significantly inhibited the activation of SRC-3 by MCB-613 (FIGS. 4E and 4F), confirming that oxidative stress induced by MCB-613 contributes to SRC activation via the Abl kinase signaling pathway.

MCB-613 Inhibits Tumor Growth In Vivo

Figure 5:
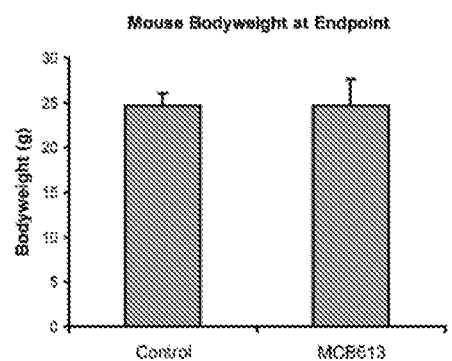
FIG. 5 shows that MCB-613 inhibits tumor growth in a MCF-7 xenograft model. Panel A shows that MCB-613 treatment has no effect on mouse body weight. Mice were treated with vehicle (n=10) or MCB-613 (n=10) for 7 weeks after mammary gland injection of MCF-7 cells. Panel B shows that MCB-613 treatment inhibits tumor growth in vivo. Tumor volume measurements for both groups of mice throughout the treatment are shown. Data are represented as mean±SEM. *P<0.05, **P<0.01.
Figure 5:
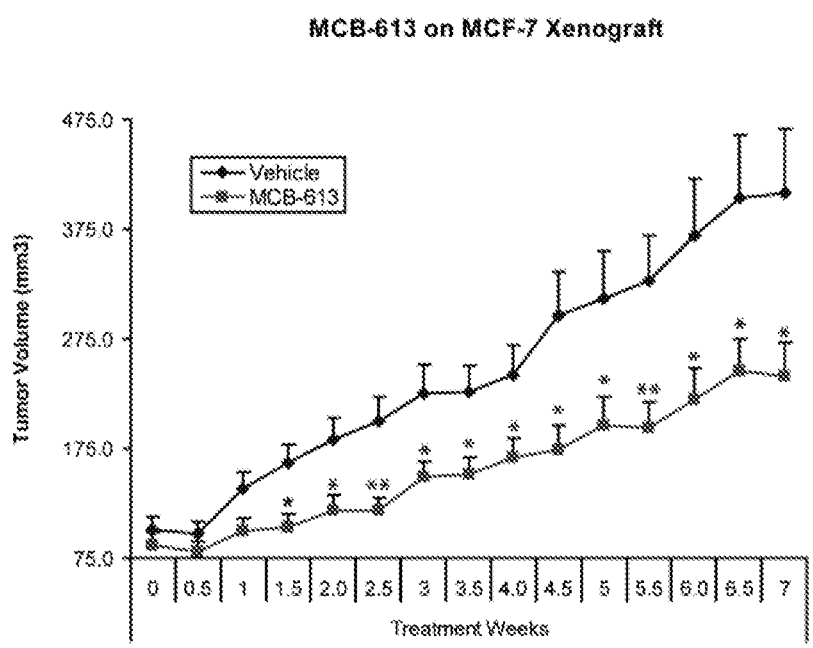

To further evaluate the anti-cancer potential of MCB-613, a MCF-7 breast cancer mouse xenograft model was employed to assess the tumor suppressive effects of MCB-613 in vivo. Tumors were established in athymic nude mice seven weeks after injection of MCF-7 cells into cleared mammary fat pads. An MCB-613 treated group (n=10) received i.p. injection of the compound (20 mg/kg) three times a week, while a control group (n=10) was injected with a saline vehicle. MCB-613 treatment did not lead to obvious animal toxicity as the body weights between control and treated groups were identical (FIG. 5A). However, as shown in FIG. 5B, tumor volumes in the MCB-613 treated group were significantly smaller than controls after one week of treatment and the inhibition of tumor growth by MCB-613 persisted throughout the treatment period.

A Model for SRC Hyper-Activation by MCB-613.

Figure 6:
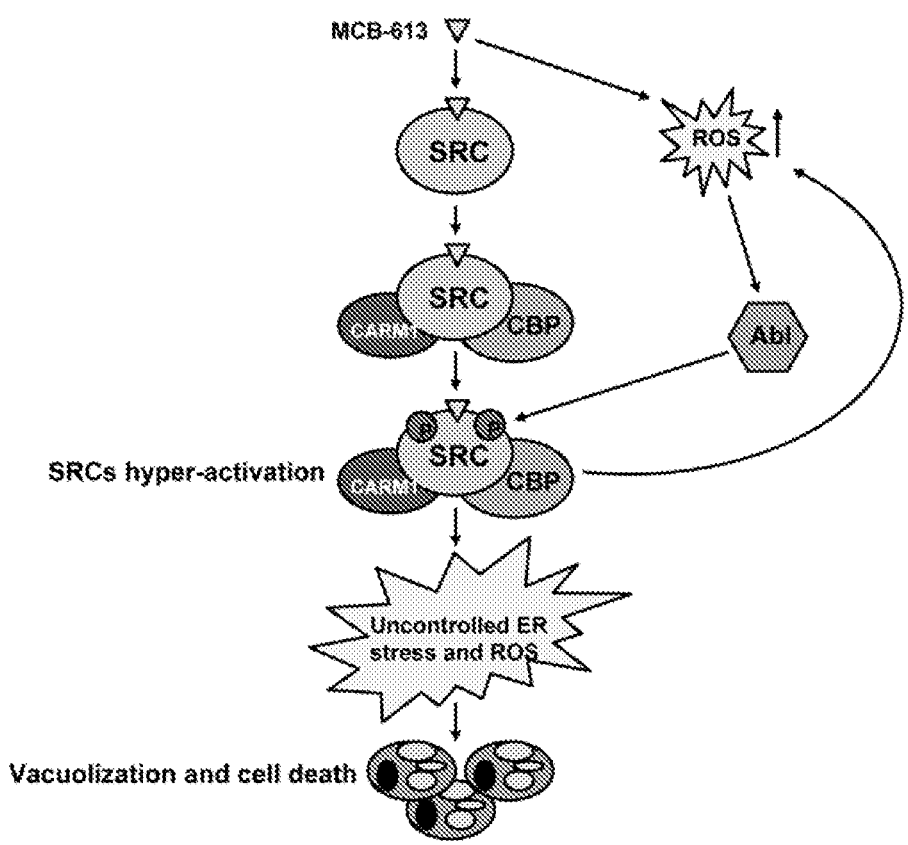
FIG. 6 depicts a model for SRC hyper-activation by MCB-613.

A model for SRC hyper-activation by MCB-613 is depicted in FIG. 6. By directly binding to SRCs, MCB-613 increases the interaction between SRCs and other coactivators such as CBP and CARM1. Meanwhile, the elevated ROS activates Abl kinase which phosphorylates and further hyper-activates SRCs. The deregulation of cellular functions and homeostasis downstream of SRCs hyper-activation strongly induces ER stress and UPR, producing more ROS and forming a positive feedback loop. The resultant excessive ER and oxidative stress overwhelms cancer cells, leading to vacuolization and cell death.

Figure 11:
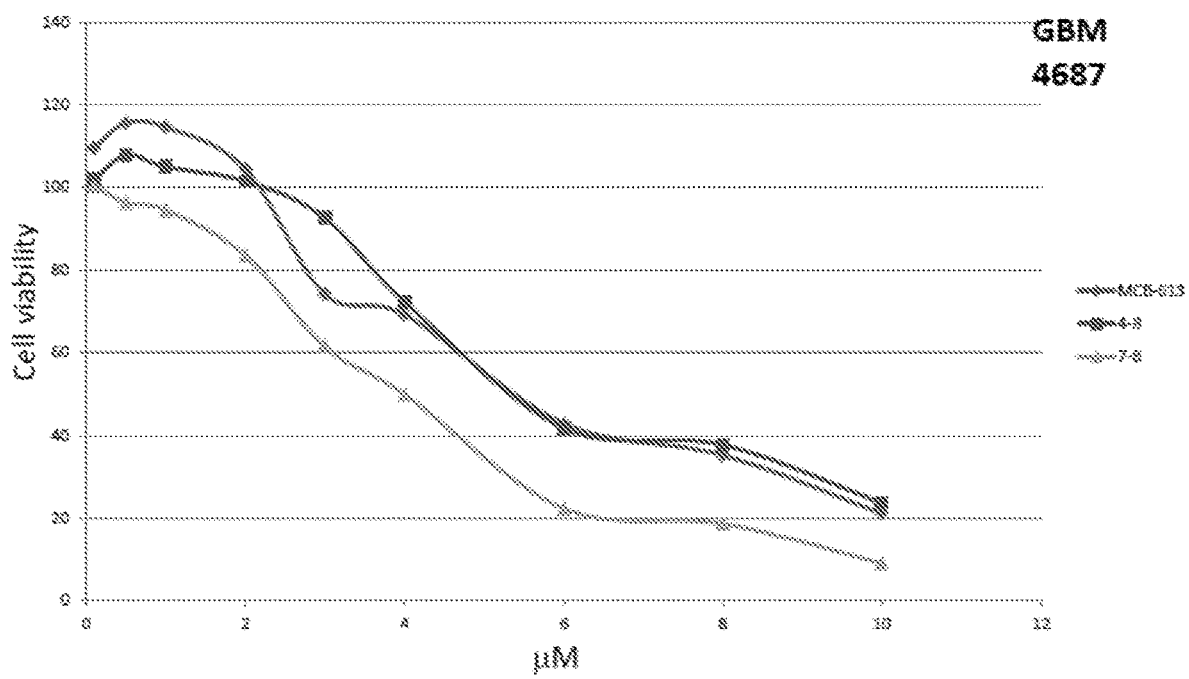
FIG. 11 shows data on the effects of MCB-613, Compound 4-8, and Compound 7-8 on tumor cell viability in cell culture on pediatric glioblastoma cell line 4687.
Figure 12:
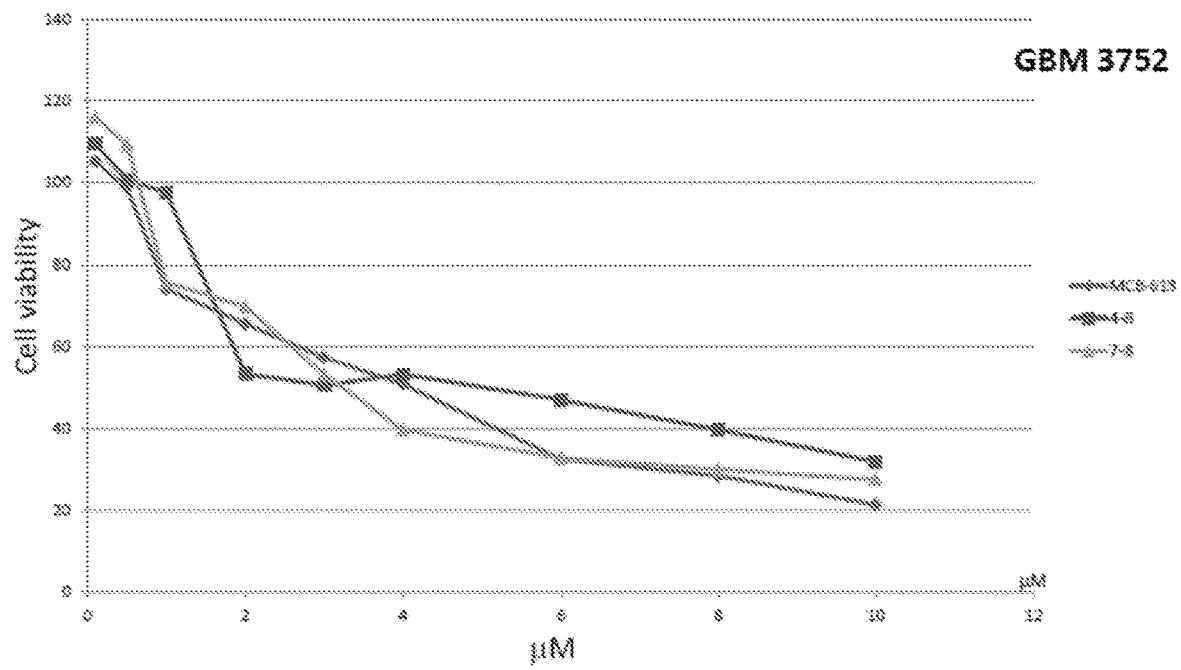
FIG. 12 shows data on the effects of MCB-613, Compound 4-8, and Compound 7-8 on tumor cell viability in cell culture on pediatric glioblastoma cell line 3752.
Figure 13:
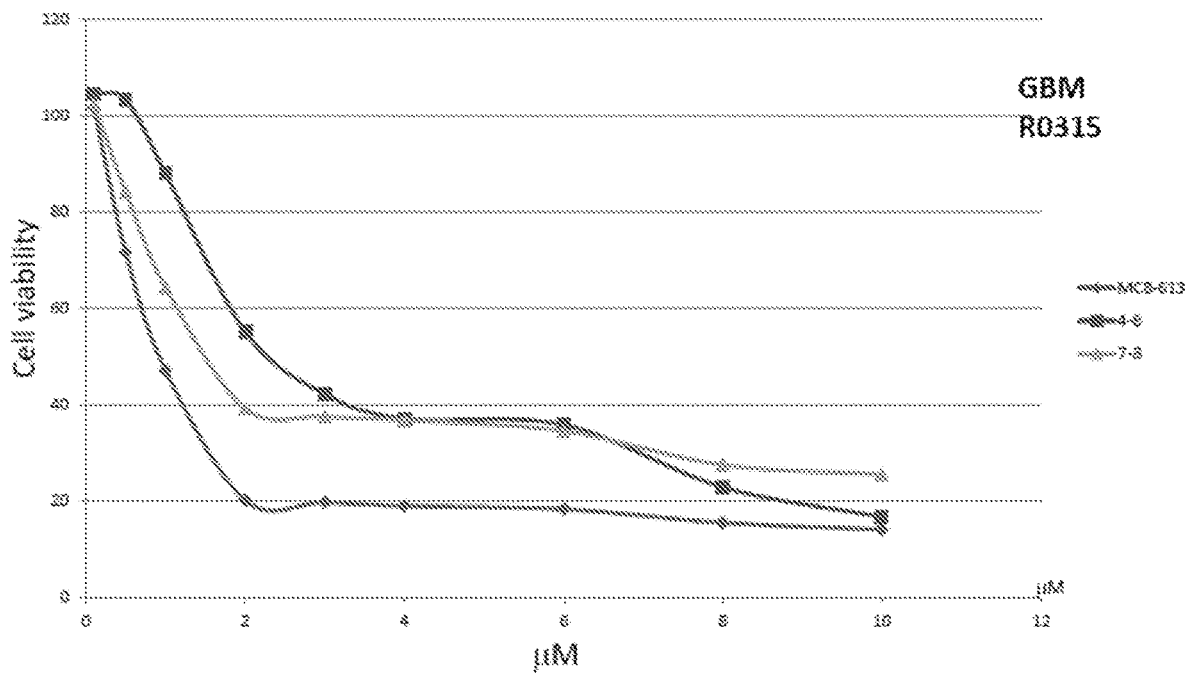
FIG. 13 shows data on the effects of MCB-613, Compound 4-8, and Compound 7-8 on tumor cell viability in cell culture on pediatric glioblastoma cell line R0315.

Example 3: Characterization of MCB-613, SYC-851 (Compound 4-8), and SYC-855 (Compound 7-8) in Pediatric Glioblastoma Multiforme (GBM) Tumor Cells The effects of MCB-613, SYC-851 (Compound 4-8), and SYC-855 (Compound 7-8) on tumor cell viability in cell culture was determined using pediatric glioblastoma multiforme cell lines 4687, 3752, and R0315. Cells were plated as monolayer cultures and treated 24 hours later with 0.5 µM, 2 µM, 3 µM, 4 µM, 6 µM, 8 µM, and 10 µM of the compounds. After 72 hours, cells were harvested and assayed for viability using a CellTiter-Glo assay (Invitrogen). The results for pediatric glioblastoma multiforme cell lines 4687, 3752, and R0315 are shown in FIGS. 11-13, respectively.

Figure 14:
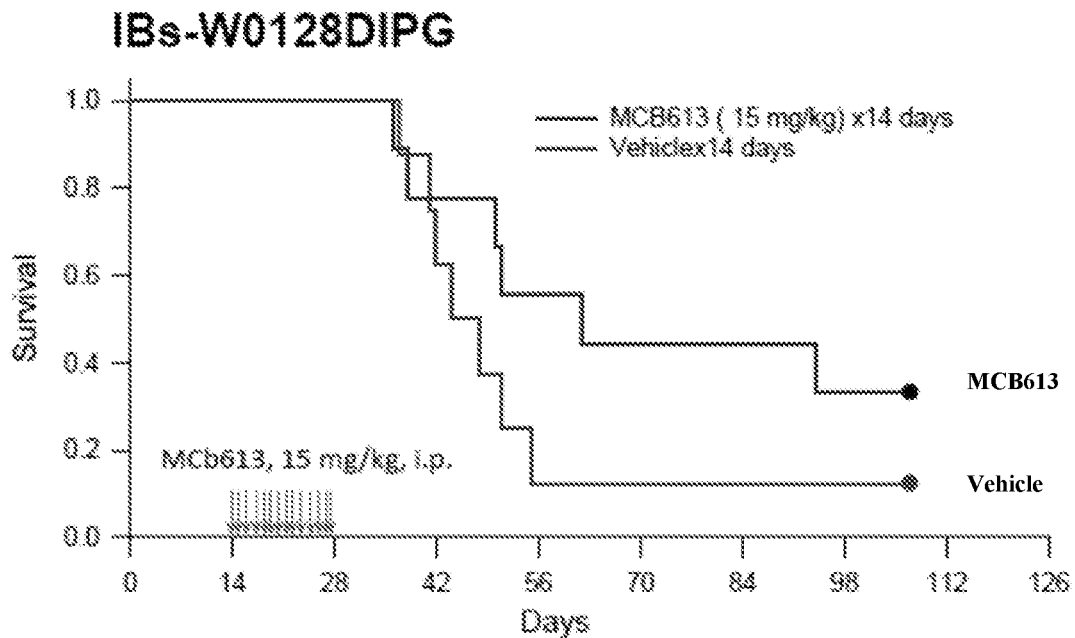
FIG. 14 is a graph showing the effects of MCB-613 on the growth of a human pediatric glioblastoma multiforme tumor growing in a mouse host.

FIG. 14 shows the effect of MCB-613 on the growth of a human pediatric GBM tumor growing in a mouse host. A tumor from a human patient was transferred directly into a mouse host (patient derived xenograft) without culturing on a plastic substrate. Tumor cells (50,000) were injected into mouse brainstems and allowed to proliferate for 14 days. Animals were treated every day with either MCB-613 (test group) or vehicle (control group) for 14 days. The animals were then housed with no further experimental manipulation. Overall survival was recorded from the experimental and control groups. It was demonstrated that MCB-613 extends survival time in a mouse patient derived xenograft GBM model system.

Figure 15A:
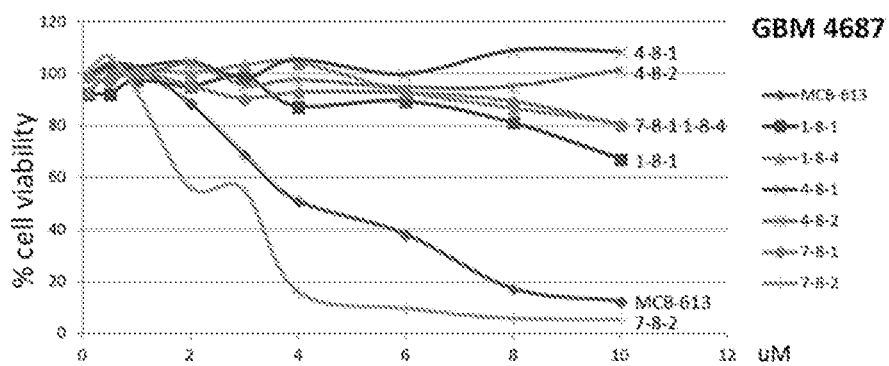
FIG. 15 contains graphs showing the effects of MCB-613, Compound 1-8-1, Compound 1-8-4, Compound 4-8-1, Compound 4-8-2, Compound 7-8-1, and Compound 7-8-2 on tumor cell viability in cell culture using pediatric glioblastoma multiforme cell lines 4687 (FIG. 15A) and R0315 (FIG. 15B).
Figure 15B:
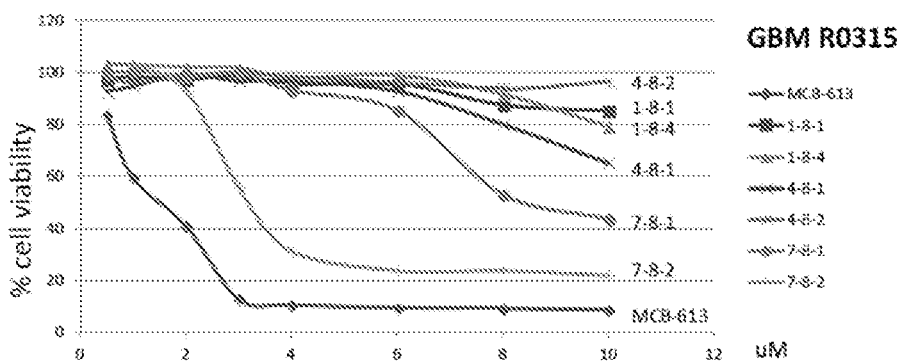

Example 4: Cytotoxicity of Compounds in Glioblastoma Multiforme (GBM) Cell Lines In Vitro The effects of MCB-613, SYC-922 (Compound 1-8-1), SYC-923 (Compound 1-8-2), SYC-924 (Compound 4-8-1), SYC-925 (Compound 4-8-2), SYC-926 (Compound 7-8-1), and SYC-927 (Compound 7-8-2) on tumor cell viability in cell culture were determined using pediatric glioblastoma multiforme cell lines 4687 and R0315. Cells were plated as monolayer cultures and treated 24 hours later with 0.5 µM, 1 µM, 2 µM, 3 µM, 4 µM, 6 µM, 8 µM, and 10 µM of the compounds. After 72 hours, cells were harvested and assayed for viability using a CellTiter-Glo assay (Invitrogen). The results for pediatric glioblastoma multiforme cell lines 4687 and R0315 are shown in FIGS. 15A and 15B, respectively.

Figure 16:
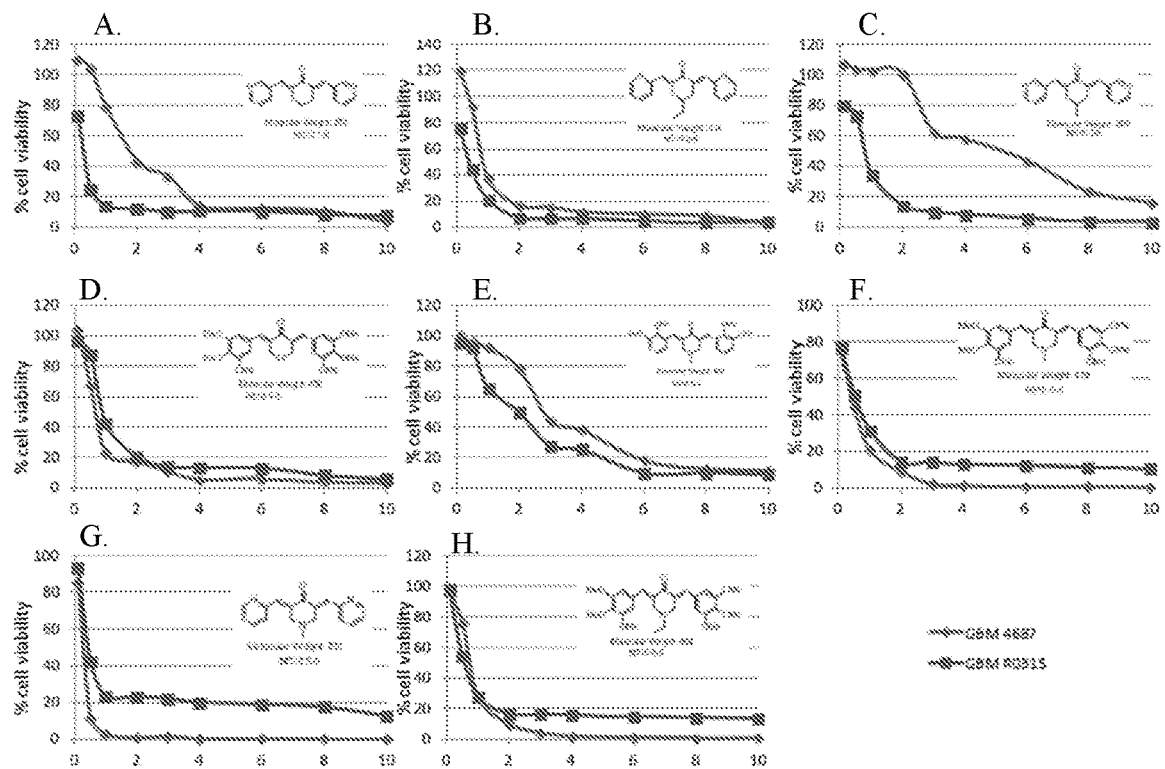
FIG. 16 contains graphs showing the effects of Compound 1-8 (Panel A), Compound 2-9 (Panel B), Compound 3-8 (Panel C), Compound 4-5 (Panel D), Compound 5-3 (Panel E), Compound 5-5 (Panel F), Compound 5-8 (Panel G), and Compound 6-5 (Panel H) on tumor cell viability in cell culture using pediatric glioblastoma multiforme cell lines 4687 and R0315.

The effects of SYC-907 (Compound 1-8), SYC-908 (Compound 2-9), SYC-909 (Compound 3-8), SYC-910 (Compound 4-5), SYC-911 (Compound 5-3), SYC-912 (Compound 5-5), SYC-928 (Compound 5-8), and SYC-914 (Compound 6-5) were determined using pediatric glioblastoma multiforme cell lines 4687 and R0315 according to the procedures described above. The results are shown in FIG. 16.

Figure 17:
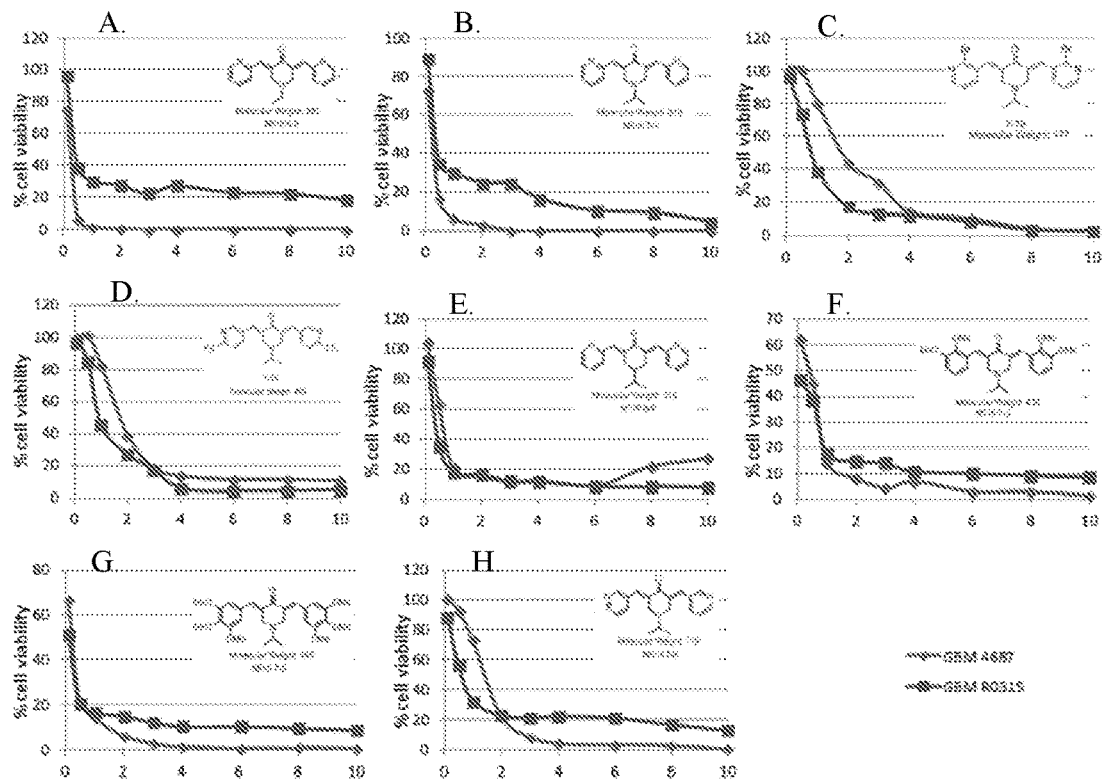
FIG. 17 contains graphs showing the effects of Compound 6-9 (Panel A), Compound 7-9 (Panel B), Compound 7-18 (Panel C), Compound 7-19 (Panel D), Compound 8-9 (Panel E), Compound 7-3 (Panel F), Compound 7-5 (Panel G), and Compound 7-8 (Panel H) on tumor cell viability in cell culture using pediatric glioblastoma multiforme cell lines 4687 and R0315.

The effects of SYC-915 (Compound 6-9), SYC-916 (Compound 7-9), SYC-917 (Compound 7-18), SYC-918 (Compound 7-19), SYC-919 (Compound 8-9), SYC-920 (Compound 7-3), SYC-921 (Compound 7-5), and SYC-855 (Compound 7-8) were determined using pediatric glioblastoma multiforme cell lines 4687 and R0315 according to the procedures described above. The results are shown in FIG. 17.

Figure 18A:
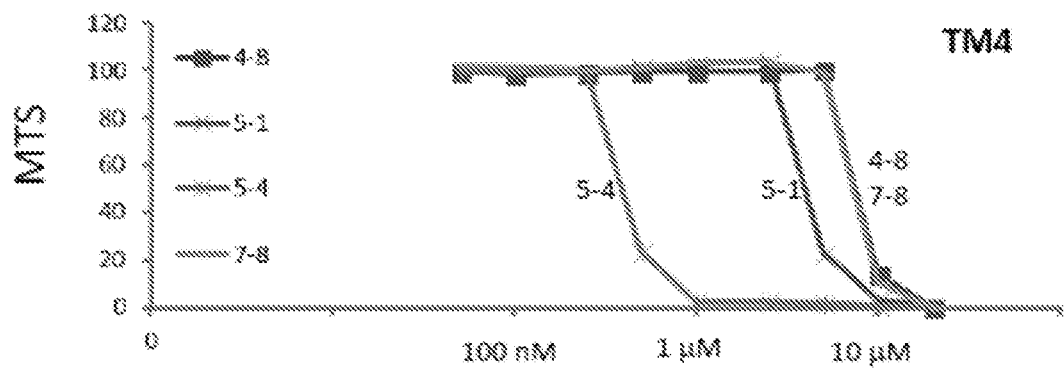
FIG. 18 contains graphs showing the effects of Compound 4-8, Compound 5-1, Compound 5-4, and Compound 7-8 on TM4 Sertoli cells (FIG. 18A) and on pediatric glioblastoma multiforme cell lines R0315 (FIG. 18B) and 4687 (FIG. 18C).
Figure 18B:
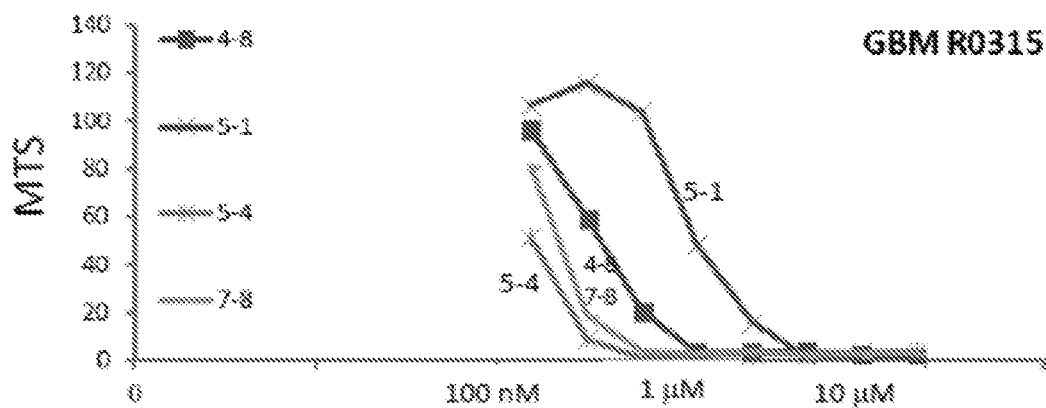
Figure 18C:
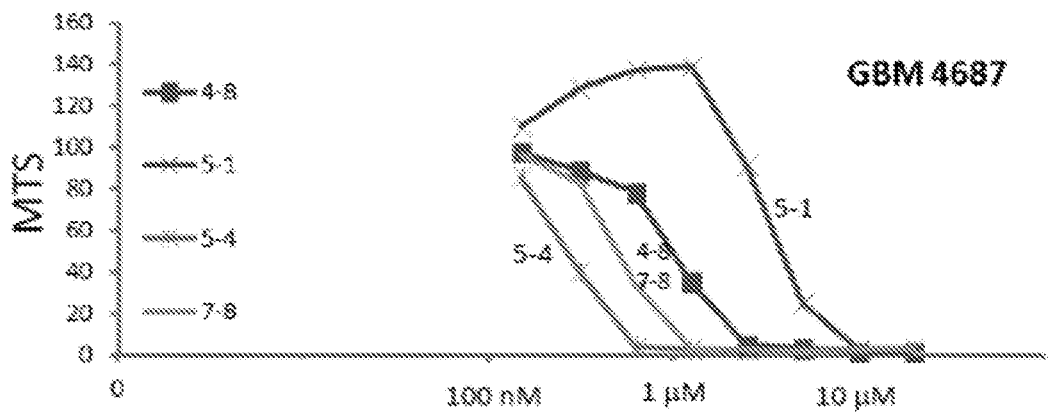

Example 5: Effects of Compounds on TM4 Sertoli and Glioblastoma Multiforme (GBM) Cell Lines The effects of SYC-851 (Compound 4-8), SYC-852 (Compound 5-1), SYC-853 (Compound 5-4), and SYC-855 (Compound 7-8) on TM4 Sertoli cells and on GBM cancer cells were determined. Cells were plated as monolayer cultures and treated 24 hours later with the indicated concentration of compounds. After 72 hours, cells were harvested and assayed for viability using a CellTiter-Glo assay (Invitrogen). The results for TM4 Setoli cells and for pediatric glioblastoma multiforme cell lines R0315 and 4687 and are shown in FIGS. 18A, 18B, and 18C, respectively. SYC-851 (Compound 4-8) and SYC-855 (Compound 7-8) display more toxicity to cancer cells than to non-cancer cells.

Example 6: Effects of Compounds on SRC-3 Intrinsic Transcriptional Activity

Figure 19:
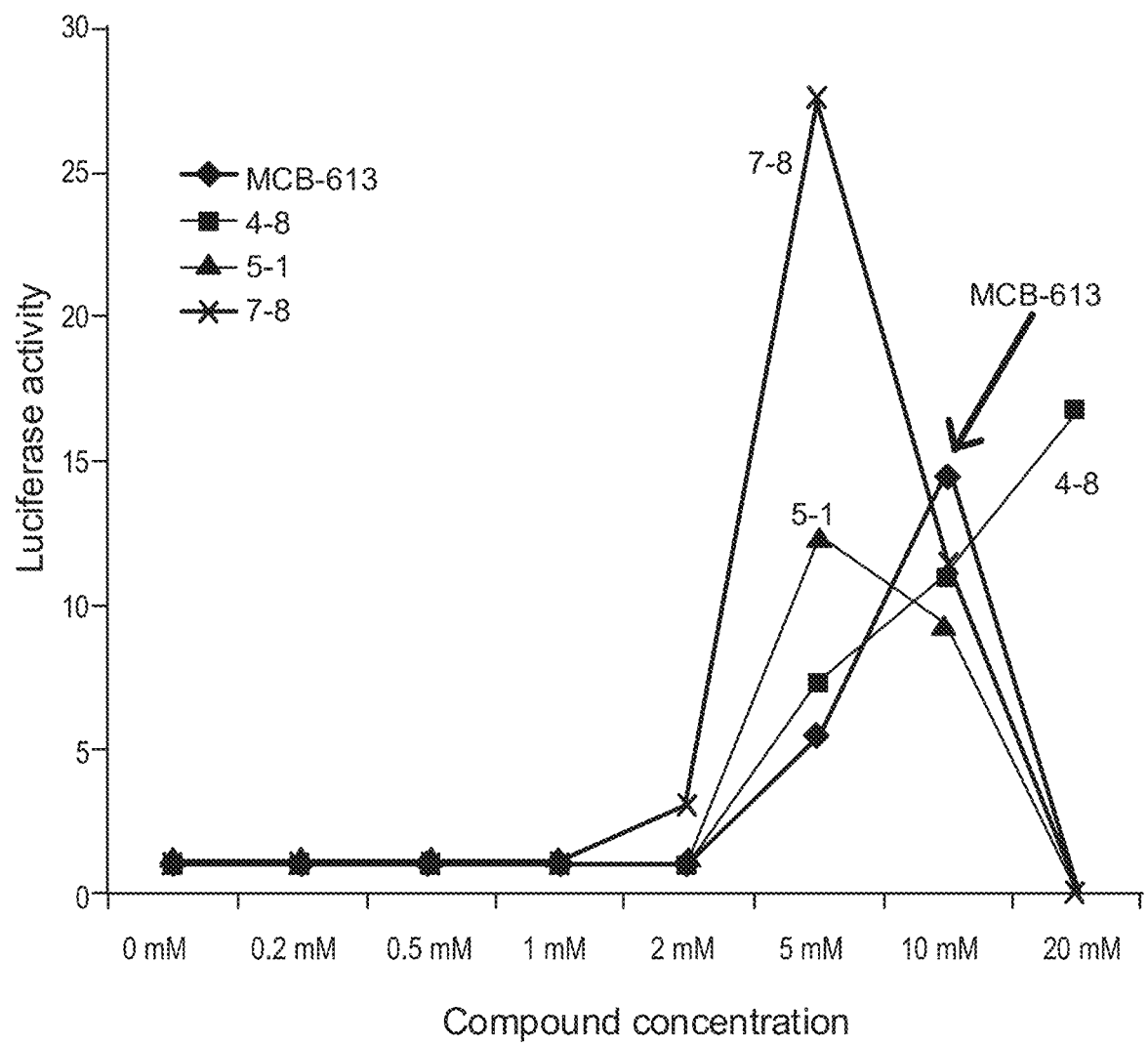
FIG. 19 contains a graph showing the effects of MCB-613, Compound 4-8, Compound 5-1, and Compound 7-8 on SRC-3 instrinsic transcriptional activity using a luciferase assay.

The effects of MCB-613, SYC-851 (Compound 4-8), SYC-852 (Compound 5-1), and SYC-855 (Compound 7-8) on SRC-3 instrinsic transcriptional activity was determined by measuring luciferase activity. HeLa cells were transfected with a Gal4 responsive luciferase reporter (pG5-luc) and a construct encoding SRC-1, SRC-2 or SRC-3 fused with the DNA binding domain of Gal4 (pBIND-SRC-1, pBIND-SRC-2 or pBIND-SRC-3) were treated with the indicated compounds. The results are shown in FIG. 19. SYC-855 (Compound 7-8) demonstrates a high intrinsic transcriptional activity.

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims.

Further, while only certain representative compounds, methods, and aspects of these compounds and methods are specifically described, other compounds and methods are intended to fall within the scope of the appended claims. Thus, a combination of steps, elements, components, or constituents can be explicitly mentioned herein; however, all other combinations of steps, elements, components, and constituents are included, even though not explicitly stated.

What is claimed is:

1. A method for treating cancer in a subject, comprising: administering to the subject an effective amount of a compound of the following formula:

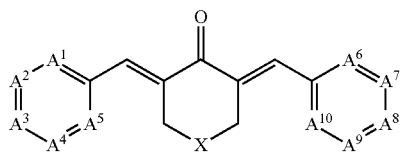

or a pharmaceutically acceptable salt or prodrug thereof, wherein:
$A^1$, $A^2$, $A^6$, and $A^7$ are each independently $CR^1$, wherein each $R^1$ is hydrogen, halogen, alkoxy, cyano, trifluoromethyl, or substituted or unsubstituted $C_{1-6}$ alkyl;
$A^3$, $A^4$, $A^5$, $A^8$, $A^9$, and $A^{10}$ are each CH; and
X is $NR^4$, wherein $R^4$ is substituted or unsubstituted $C_{3-6}$ alkyl
wherein the cancer is selected from the group consisting of breast cancer, liver cancer, lung cancer, prostate cancer, and glioblastoma.

2. The method of claim 1, wherein each $R^1$ is hydrogen or methoxy.

3. The method of claim 1, wherein $A^1$ and $A^6$ are C—$OCH_3$.

4. The method of claim 1, wherein $A^2$ and $A^7$ are C—$OCH_3$.

5. The method of claim 1, wherein $R^4$ is branched alkyl.

6. The method of claim 3, wherein $A^2$ and $A^7$ are CH.

7. The method of claim 4, wherein $A^1$ and $A^6$ are CH.

* * * * *